(12) United States Patent
Vogt et al.

(10) Patent No.: US 9,920,188 B2
(45) Date of Patent: Mar. 20, 2018

(54) PVCP PHANTOMS AND THEIR USE

(71) Applicant: The United States of America, as represented by the Secretary, Department of Health and Human Services, Washington, DC (US)

(72) Inventors: William Vogt, Washington, DC (US); Thomas Joshua Pfefer, Greenbelt, MD (US); Congxian Jia, Silver Spring, MD (US); Keith Wear, Rockville, MD (US); Brian Garra, Adelphi, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 15/341,983

(22) Filed: Nov. 2, 2016

(65) Prior Publication Data

US 2017/0122915 A1    May 4, 2017

Related U.S. Application Data

(60) Provisional application No. 62/249,809, filed on Nov. 2, 2015.

(51) Int. Cl.
*G09B 23/30* (2006.01)
*G09B 23/00* (2006.01)
(Continued)

(52) U.S. Cl.
CPC .................. *C08K 7/20* (2013.01); *A61B 8/00* (2013.01); *C08K 3/22* (2013.01); *C08K 5/11* (2013.01);
(Continued)

(58) Field of Classification Search
CPC ....... C08L 27/06; C08L 2203/00; C08K 3/22; C08K 5/11; C08K 5/12; C08K 7/20;
(Continued)

(56) References Cited

U.S. PATENT DOCUMENTS 5,196,343 A  3/1993  Zerhouni et al.
6,854,976 B1  2/2005  Suhr
(Continued)

OTHER PUBLICATIONS

Bauer et al. "Quantitative photoacoustic imaging: correcting for heterogeneous light fluence distributions using diffuse optical tomography." *Journal of Biomedical Optics* 16, No. 9 (2011): 096016-096016.
(Continued)

*Primary Examiner* — Jennifer Wecker
(74) *Attorney, Agent, or Firm* — Klarquist Sparkman, LLP

(57) ABSTRACT

Novel phantoms are provided herein that can accurately mimic the optical and/or acoustic properties of living tissue. The disclosed phantoms are constructed of one or more polyvinyl chloride plastisol (PVCP) gels comprising a PVC and a binary plasticizer. The phantoms can be used, for example, to calibrate or test an optical and/or acoustic detection system, such as a photoacoustic imaging system or an ultrasound imaging system.

32 Claims, 34 Drawing Sheets
(29 of 34 Drawing Sheet(s) Filed in Color)

(51) Int. Cl.
| | |
|---|---|
| C08K 5/11 | (2006.01) |
| C08K 5/12 | (2006.01) |
| C08L 27/06 | (2006.01) |
| C08K 3/22 | (2006.01) |
| C08K 7/20 | (2006.01) |
| A61B 8/00 | (2006.01) |
| G01N 29/30 | (2006.01) |
| G01N 21/01 | (2006.01) |
| A61B 5/00 | (2006.01) |
| G01N 21/17 | (2006.01) |

(52) U.S. Cl.
CPC ............ *C08K 5/12* (2013.01); *G09B 23/30* (2013.01); *A61B 5/0095* (2013.01); *A61B 8/587* (2013.01); *C08K 2003/2241* (2013.01); *C08K 2201/003* (2013.01); *C08L 2203/00* (2013.01); *G01N 21/1702* (2013.01)

(58) Field of Classification Search
CPC ...... C08K 2003/2241; C08K 2201/003; A61B 8/00; A61B 5/0095; G01N 21/1702; G09B 23/30
See application file for complete search history.

(56) References Cited

U.S. PATENT DOCUMENTS

| | | | |
|---|---|---|---|
| 7,272,766 B2 | 9/2007 | Sakezles et al. | |
| 7,419,376 B2 | 9/2008 | Sarvazyan et al. | |
| 7,738,624 B2 | 6/2010 | Herold et al. | |
| 8,459,095 B2 | 6/2013 | Morris et al. | |
| 8,480,407 B2 | 7/2013 | Campbell et al. | |
| 8,568,147 B2 | 10/2013 | Kuo et al. | |
| 8,678,831 B2 | 3/2014 | Trotta et al. | |
| 8,686,335 B2 | 4/2014 | Schmid et al. | |
| 8,906,268 B2* | 12/2014 | Boutet ............... | A61B 5/0059 252/408.1 |
| 8,932,223 B2 | 1/2015 | Emelianov et al. | |
| 8,958,865 B2 | 2/2015 | Hsu et al. | |
| 2007/0015933 A1* | 1/2007 | Kim ..................... | C07C 69/67 560/90 |
| 2013/0116538 A1 | 5/2013 | Herzog et al. | |
| 2015/0075287 A1 | 3/2015 | Herzog et al. | |
| 2016/0370285 A1* | 12/2016 | Jang .................... | G01N 21/278 |

OTHER PUBLICATIONS

Bohndiek et al. "Development and application of stable phantoms for the evaluation of photoacoustic imaging instruments." *PloS One* 8, No. 9 (2013): e75533.
Chandrasekharan et al. "Non-resonant multiphoton photoacoustic spectroscopy for noninvasive subsurface chemical diagnostics." *Applied Spectroscopy* 58, No. 11 (2004): 1325-1333.
Cook et al. "Tissue-mimicking phantoms for photoacoustic and ultrasonic imaging." *Biomedical Optics Express* 2, No. 11 (2011): 3193-3206.
Elson et al. "Ultrasound-mediated optical tomography: a review of current methods." *Interface Focus* 1, No. 4 (2011): 632-648.
Hillman. "Optical brain imaging in vivo: techniques and applications from animal to man." *Journal of Biomedical Optics* 12, No. 5 (2007): 051402-051402.
Jacques. "Optical properties of biological tissues: a review." *Physics in Medicine and Biology* 58, No. 11 (2013): R37.
James et al. "Integrated photoacoustic, ultrasound and fluorescence platform for diagnostic medical imaging-proof of concept study with a tissue mimicking phantom." *Biomedical Optics Express* 5, No. 7 (2014): 2135-2144.
Karpiouk et al. "Combined ultrasound and photoacoustic imaging to detect and stage deep vein thrombosis: phantom and ex vivo studies." *Journal of Biomedical Optics* 13, No. 5 (2008): 054061-054061.
Ke et al. "Performance characterization of an integrated ultrasound, photoacoustic, and thermoacoustic imaging system." *Journal of Biomedical Optics* 17, No. 5 (2012): 0560101-0560106.
Kharine et al. "Poly (vinyl alcohol) gels for use as tissue phantoms in photoacoustic mammography." *Physics in Medicine and Biology* 48, No. 3 (2003): 357.
Kim et al. "Deeply penetrating in vivo photoacoustic imaging using a clinical ultrasound array system." *Biomedical Optics Express* 1, No. 1 (2010): 278-284.
Langer et al. "Two-photon absorption-induced photoacoustic imaging of Rhodamine B dyed polyethylene spheres using a femtosecond laser." *Optics Express* 21, No. 19 (2013): 22410-22422.
Li et al. "Integrated diffuse optical tomography and photoacoustic tomography: phantom validations." *Biomedical Optics Express* 2, No. 8 (2011): 2348-2353.
Lu et al. "Medical hyperspectral imaging: a review." *Journal of Biomedical Optics* 19, No. 1 (2014): 010901-010901.
Manohar et al. "Photoacoustic mammography laboratory prototype: imaging of breast tissue phantoms." *Journal of Biomedical Optics* 9, No. 6 (2004): 1172-1181.
O'Sullivan et al. "Diffuse optical imaging using spatially and temporally modulated light." *Journal of Biomedical Optics* 17, No. 7 (2012): 0713111-07131114.
Pfefer et al., "Standardization and Phantom-based Performance Evaluation of Biophotonic Devices for Clinical Imaging", *OSA Applied Industrial Optics 2015*, presentation given on Jun. 8, 2015 (no abstract submitted).
Pogue et al. "Review of tissue simulating phantoms for optical spectroscopy, imaging and dosimetry." *Journal of Biomedical Optics* 11, No. 4 (2006): 041102-041102.
Reis et al. "Quality assurance and quality control in mammography: a review of available guidance worldwide." *Insights into Imaging* 4, No. 5 (2013): 539-553.
Spirou et al. "Optical and acoustic properties at 1064 nm of polyvinyl chloride-plastisol for use as a tissue phantom in biomedical optoacoustics." *Physics in Medicine and Biology* 50, No. 14 (2005): N141.
Telenkov et al. "Frequency-domain photoacoustic phased array probe for biomedical imaging applications." *Optics Letters* 36, No. 23 (2011): 4560-4562.
Vogt et al., "Characterization of Tissue-Simulating Polymers for Photoacoustic Vascular Imaging", *Proc SPIE* 9107, 910719, May 22, 2014.
Vogt et al., "Characterization of Tissue-Simulating Polymers for Photoacoustic Vascular Imaging", *Proc SPIE* 9107, 910719, May 9, 2014.
Vogt et al., "Design and Phantom-based Validation of a Bimodal Ultrasound-Photoacoustic Imaging System for Spectral Detection of Optical Biomarkers", *SPIE Photonics West 2015, Proc. SPIE* 9315, submitted Feb. 27, 2015.
Vogt et al., "Design and Phantom-based Validation of a Bimodal Ultrasound-Photoacoustic Imaging System for Spectral Detection of Optical Biomarkers", *SPIE Photonics West 2015*, Feb. 8, 2015.
Vogt et al., "Photoacoustic Tomography for Deep in vivo Imaging of Optical Biomarkers: System Design and Validation", *FDA Science Forum 2015*, abstract submitted Feb. 20, 2015.
Vogt et al., "Photoacoustic Tomography System for In Vivo Detection of Endogenous and Exogenous Biomarkers", *FDA MCMi Regulatory Science Symposium*, Jun. 2-3, 2014.
Vogt et al., "Quantitative Assessment of Photoacoustic Tomography Systems Integrating Clinical Ultrasound Transducers Using Novel Tissue-Simulating Phantoms", *SPIE Photonics West 2015, Proc SPIE* 9323, submitted Jan. 28, 2015.
Vogt et al., "Quantitative Assessment of Photoacoustic Tomography Systems Integrating Clinical Ultrasound Transducers Using Novel Tissue-Simulating Phantoms", *SPIE Photonics West 2015*, Feb. 7, 2015.
Wang et al. "Photoacoustic tomography: in vivo imaging from organelles to organs." *Science* 335, No. 6075 (2012): 1458-1462.
Wang et al. "Ultrasound-mediated biophotonic imaging: a review of acousto-optical tomography and photo-acoustic tomography." *Disease Markers* 19, No. 2-3 (2004): 123-138.

(56) References Cited

OTHER PUBLICATIONS

Wang. "Prospects of photoacoustic tomography." *Medical Physics* 35, No. 12 (2008): 5758-5767.
Xia et al. "Design and evaluation of a laboratory prototype system for 3D photoacoustic full breast tomography." *Biomedical Optics Express* 4, No. 11 (2013): 2555-2569.
Xia et al. "Poly (vinyl alcohol) gels as photoacoustic breast phantoms revisited." *Journal of Biomedical Optics* 16, No. 7 (2011): 075002-075002.
Yakovlev et al. "Stimulated Raman photoacoustic imaging." *Proceedings of the National Academy of Sciences* 107, No. 47 (2010): 20335-20339.
Yao et al. "Photoacoustic tomography: fundamentals, advances and prospects." *Contrast Media & Molecular Imaging* 6, No. 5 (2011): 332-345.
Zhang et al. "Backward-mode multiwavelength photoacoustic scanner using a planar Fabry-Perot polymer film ultrasound sensor for high-resolution three-dimensional imaging of biological tissues." *Applied Optics* 47, No. 4 (2008): 561-577.

\* cited by examiner

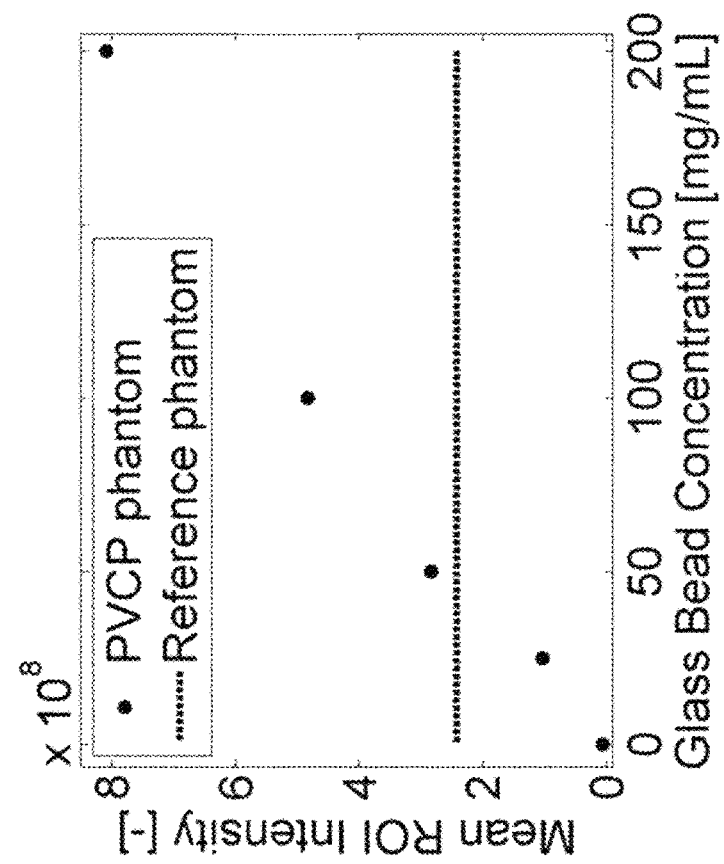
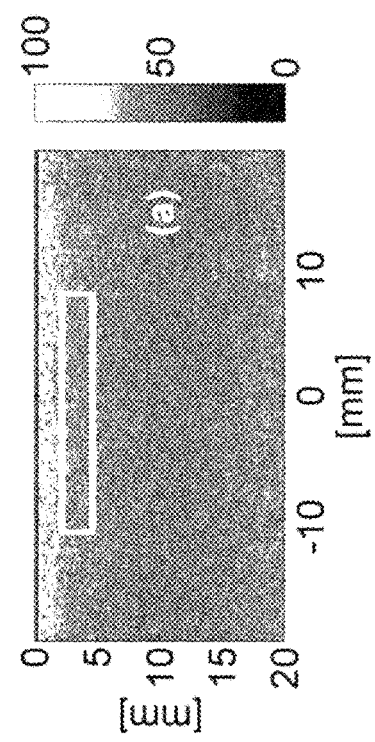
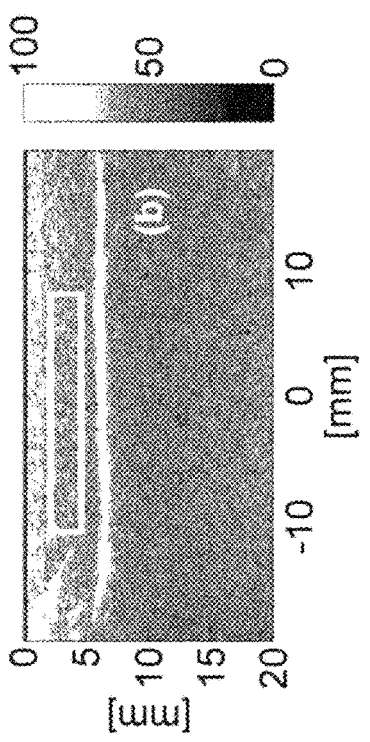

FIG. 13A
Phantom 1 with wires
FIG. 13B
Phantom 2 with tubes
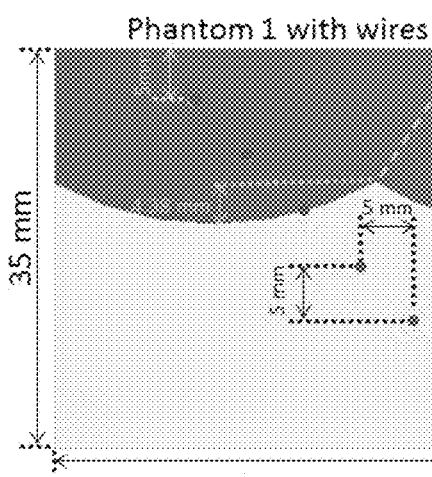
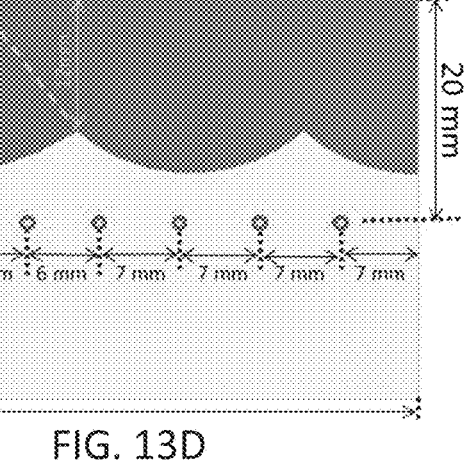
FIG. 13C
FIG. 13D
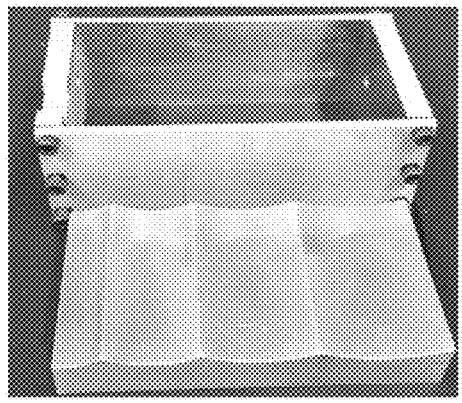
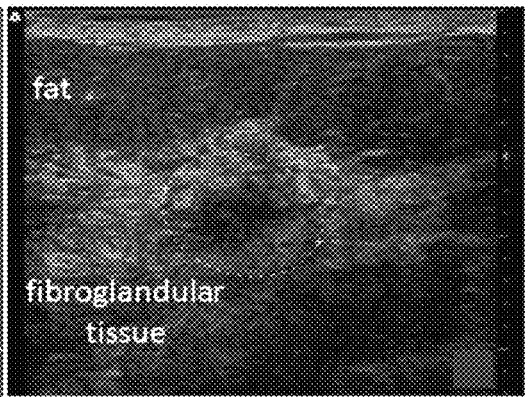

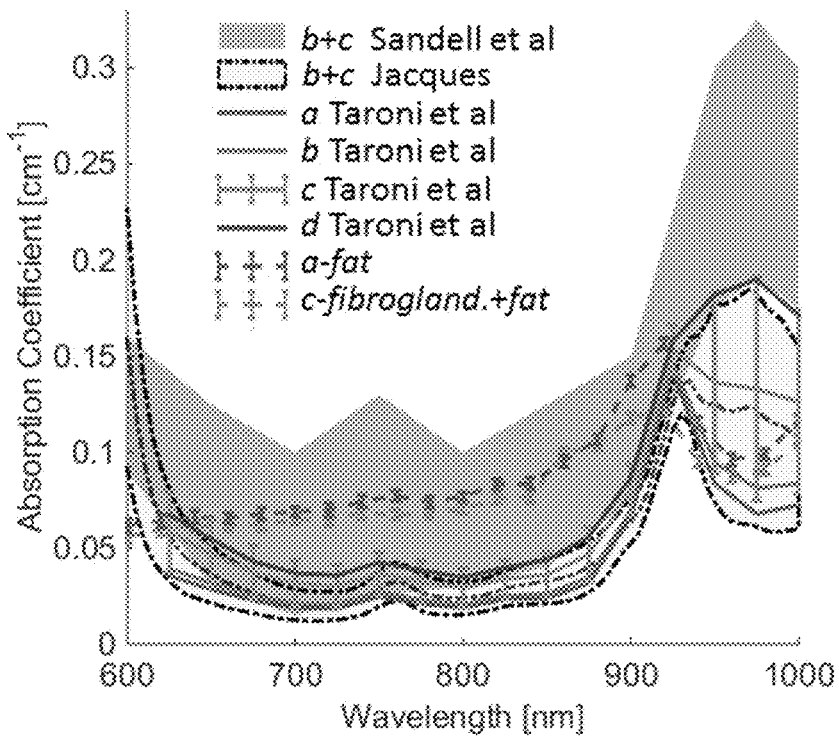
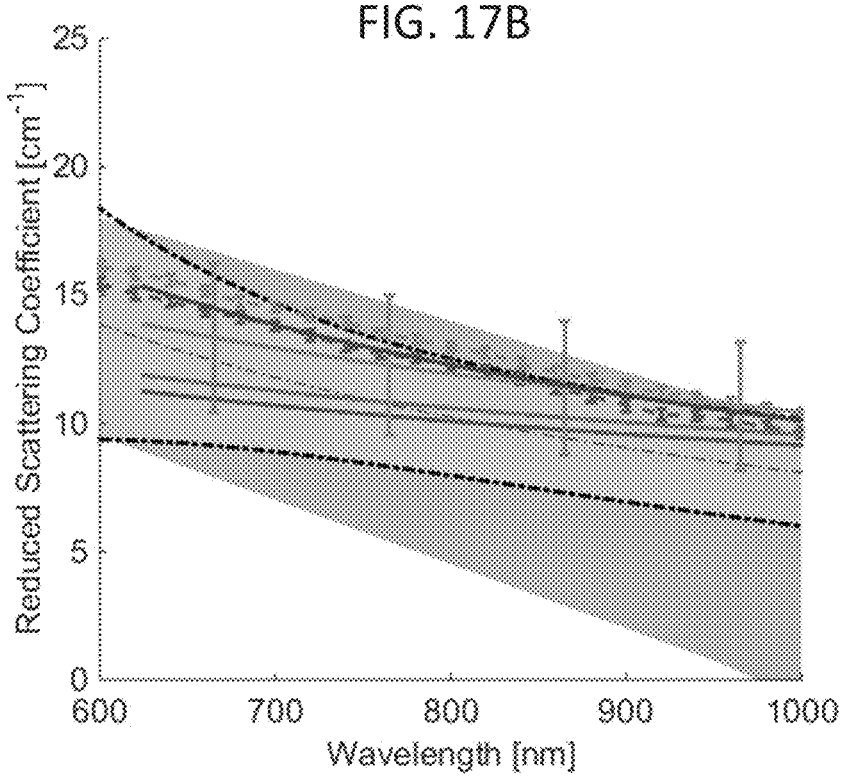

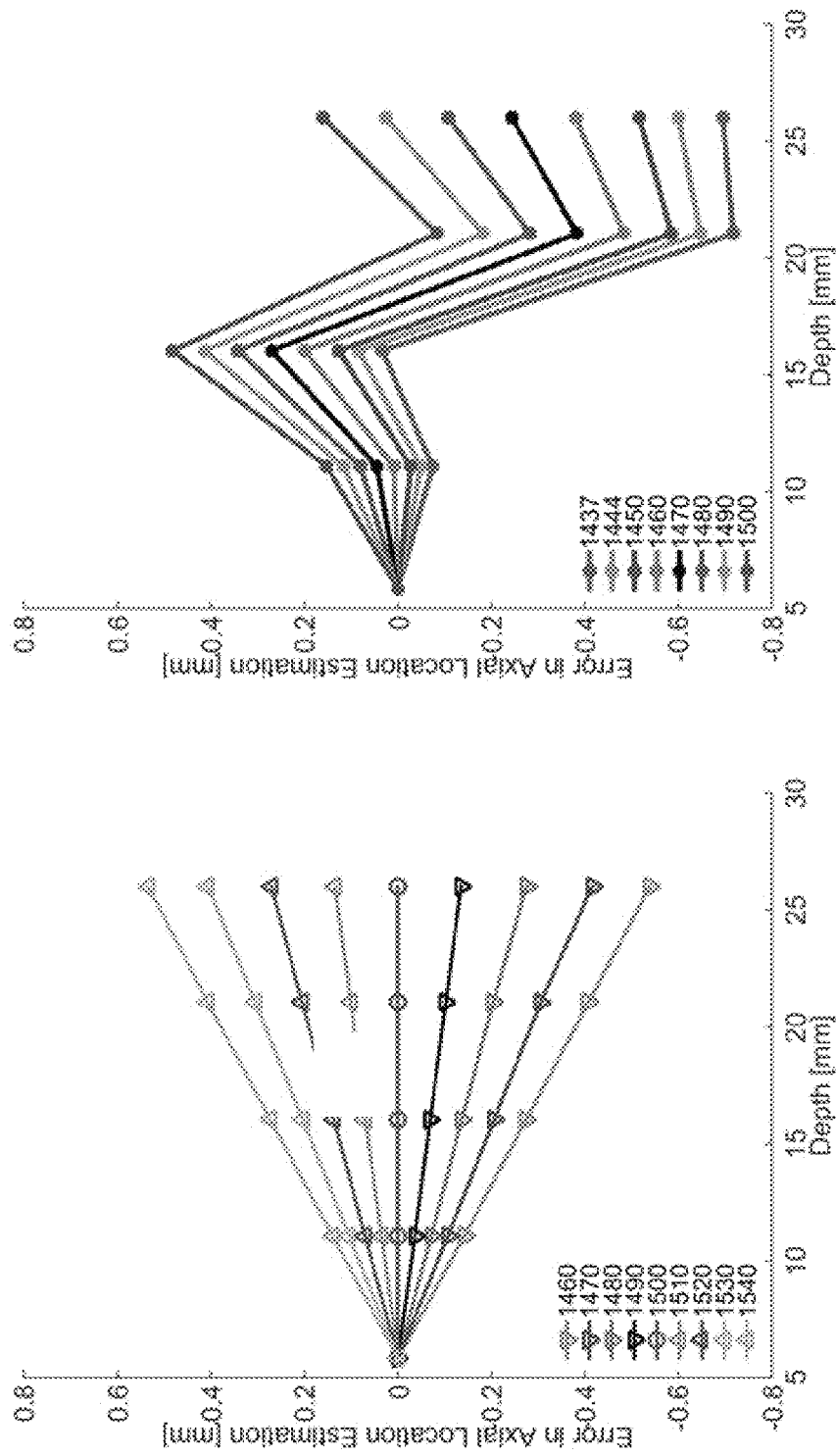

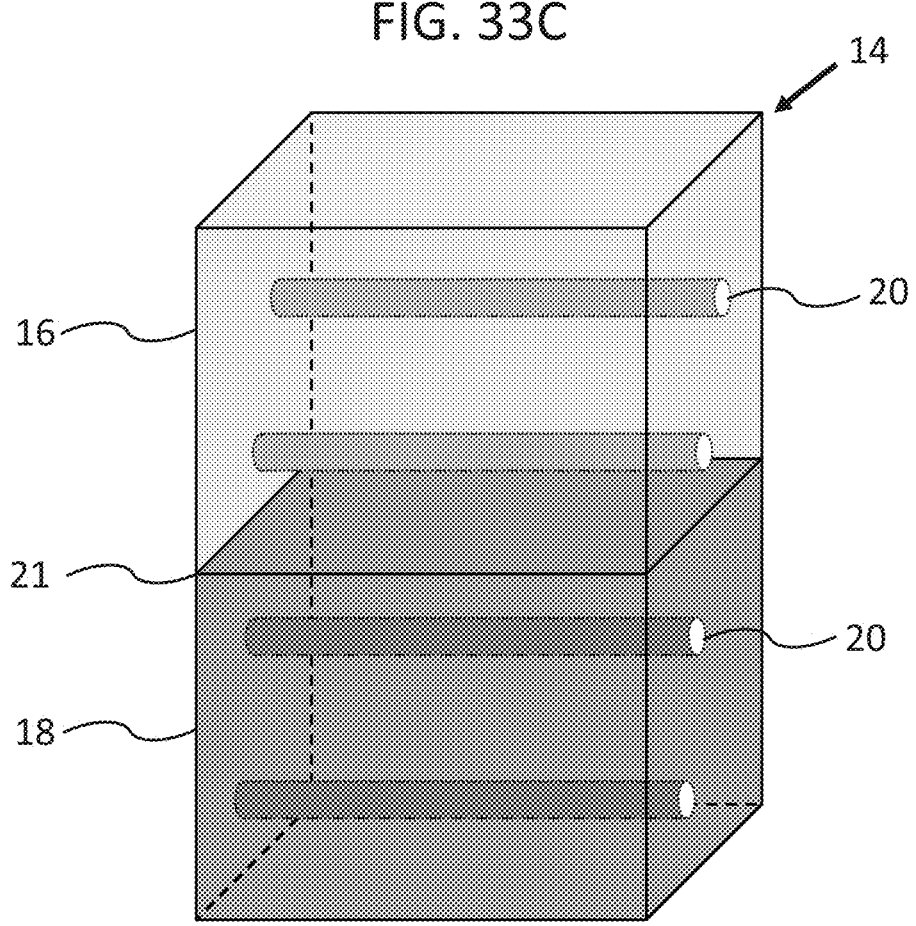

PVCP PHANTOMS AND THEIR USE

CROSS REFERENCE TO RELATED APPLICATIONS

This application claims priority to U.S. Provisional Application No. 62/249,809, filed Nov. 2, 2015, which is incorporated by reference in its entirety.

FIELD OF THE DISCLOSURE

This relates to phantoms that can accurately mimic the optical and acoustic properties of living tissue and their use, for example, to calibrate and test instrumentation for detecting (such as sensing and imaging) optical and/or acoustic properties of a sample.

BACKGROUND

Photoacoustic Imaging (PAI) is an imaging modality that combines pulsed laser irradiation with ultrasonic sensing to provide optical absorption information at depths on the order of centimeters. Exemplary PAI applications include vascular imaging, cancer detection, and mammography. Because PAI is an emerging technology, there are no currently recognized standard test methods for conducting device performance assessment, quality control, and inter-comparison. Tissue-simulating phantoms provide useful test objects and are incorporated in image quality standards for medical imaging technologies. Prior PAI phantoms can successfully mimic the optical properties of tissue or the acoustic properties of tissue, but not both.

SUMMARY

This disclosure provides novel poly(vinyl chloride) plastisol (PVCP) phantoms that are stable, have biologically-relevant optical and acoustic characteristics, and can be used for standardized assessment of detection and imaging systems, particularly photoacoustic and ultrasound detection and imaging systems. Thus, in several embodiments, the PVCP phantom can be a photoacoustic imaging phantom or ultrasound imaging phantoms.

In several embodiments, the PVCP phantom can be constructed of a PVCP gel comprising a combination of poly(vinyl chloride) (PVC) and binary plasticizer comprising benzyl butyl phthalate (BBP) and di(2-ethylhexyl) adipate (DEHA). In contrast to prior PVCP phantoms, the novel combination of materials used in the disclosed phantoms allows for speed of sound and acoustic attenuation through the phantom that overlap with tissue-relevant properties.

In some embodiments, the PVCP gel included in the PVCP phantom can include one or more additives comprising an optical absorber, an optical scatterer, an acoustic absorber, and/or an acoustic scatterer to adjust the optical and/or acoustic properties of the PVCP gel to mimic the corresponding optical and/or acoustic properties of a particular tissue type of interest. Non-limiting examples of the particular tissue type that the PVCP gel can mimic include fatty breast tissue, breast tissue with moderate relative fat/parenchyma content, parenchymal breast tissue, skin, abdominal fat, brain, liver, and skeletal muscle.

The PVCP phantom can be shaped as needed for its intended use. In some embodiments, the PVCP phantom can have realistic optical and/or acoustic properties and comprise a shape that simulates the morphology, optical properties, and acoustic properties of a living organ or tissue, of body parts, or of whole animals, such as a small mammal, for example, a mouse. In some embodiments, the PVCP phantom can comprise the shape of a breast. In some embodiments, the PVCP phantom can comprise the shape of a cube, cuboid, sphere, ellipsoid, or cylinder.

In some embodiments, one or more filaments, one or more solid inclusions, and/or one or more fluid channels, can be embedded in the PVCP gel included in the PVCP phantom to provide a series of targets for calibrating or testing the performance characteristics of a photoacoustic detection system. In some embodiments, the one or more fluid channels can be filled with a liquid solution comprising one or more of an optical absorber, an optical scatterer, an acoustic absorber, and an acoustic scatterer, to provide a series of targets for calibrating or testing the performance characteristics of a photoacoustic detection system or an acoustic detection system.

Compositions that comprise PVC and a binary plasticizer comprising or consisting of BBP and DEHA are also provided. The compositions can be used, for example, in a method of producing a disclosed PVCP phantom. For example, in some embodiments, a method of producing a disclosed PVCP phantom is provided, the method comprising providing a disclosed composition comprising PVC and a binary plasticizer comprising or consisting of BBP and DEHA, and forming the composition into the shape of the phantom.

Methods of using a disclosed PVCP phantom to calibrate or test an optical and/or acoustic detection system, such as a photoacoustic imaging system or ultrasound imaging system, are also provided. Optical acoustic detection systems including a disclosed PVCP phantom are also disclosed.

The foregoing and other features and advantages of this disclosure will become more apparent from the following detailed description of several embodiments which proceeds with reference to the accompanying figures.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIGS. 6A-6C illustrate the backscatter estimation for PVCP gels formed using 10% m/m PVC and binary plasticizer comprising 75/25% v/v BBP/DEHA and varying concentrations of glass microparticles. A reference ultrasound phantom (Model 059, CIRS, Norfolk, Va.) was used as a control. Ultrasound images of (FIG. 6A) CIRS phantom and (FIG. 6B) CIRS phantom with PVCP phantom containing 50 mg/mL glass beads on top. White box denotes analyzed Region of Interest (ROI). (FIG. 6C) Mean ROI intensity vs. PVCP glass bead concentration.

(FIG. 9A) mass loss, (FIG. 9B) optical absorption, (FIG. 9C) optical scattering, (FIG. 9D) acoustic attenuation, (FIG. 9E) speed of sound. Curves in (FIGS. 9B-9D) are mean spectra with error bars omitted for clarity. Maximum 95% confidence interval is ±6% for (FIG. 9B) and (FIG. 9C), ±11.5% for (FIG. 9D).

In FIGS. 10A-10C, the phantoms and chicken breast included an array of metal wire inclusions to assay for depth of penetration. (FIG. 10D) Absorption (solid lines) and reduced scattering (dashed lines) coefficients of the two phantoms. (FIG. 10E) Contrast vs. depth in the two phantoms and chicken breast tissue. Error bars denote ±1 standard deviation.

FIGS. 13A-D illustrate a cross-sectional view of PVCP phantoms for optical and/or acoustic detection systems, such as a photoacoustic imaging system or ultrasound imaging system. The cross sections of two heterogeneous phantoms: phantom 1 with wires (13A) and phantom 2 with tubes (13B); an example of an aluminum mold with an undulating plate (13C); and an example of ultrasound breast image with an undulating boundary between fatty and fibroglandular tissue containing a cancer circled (13D) are shown.

FIGS. 17A-17B show a set of graphs illustrating (17A) optical absorption coefficient and (17B) reduced scattering coefficient for breast tissue and that two formulated phantoms (a-fat and c-fibrogland.+fat).

FIGS. 21A and 21B are a set of graphs showing the error in axial location estimation for the first five wires in the homogeneous phantom (21A) and the heterogeneous phantom (21B) using the location of the first target as reference and location estimated using true sound speed of 1500 m/s in the homogenous phantom as ground truth.

FIGS. 33A-33D illustrate exemplary embodiments of PVCP phantoms as disclosed herein. FIGS. 33A and 33B show perspective views of PVCP phantoms containing an array of embedded tubes or filaments (33A) or an array of embedded spherical inclusions (33B). FIGS. 33C and 33D show perspective views of multilayered PVCP phantoms with an array of embedded tubes or filaments (33C) or an array of embedded spherical inclusions (33D).

DETAILED DESCRIPTION

Figure 1A:
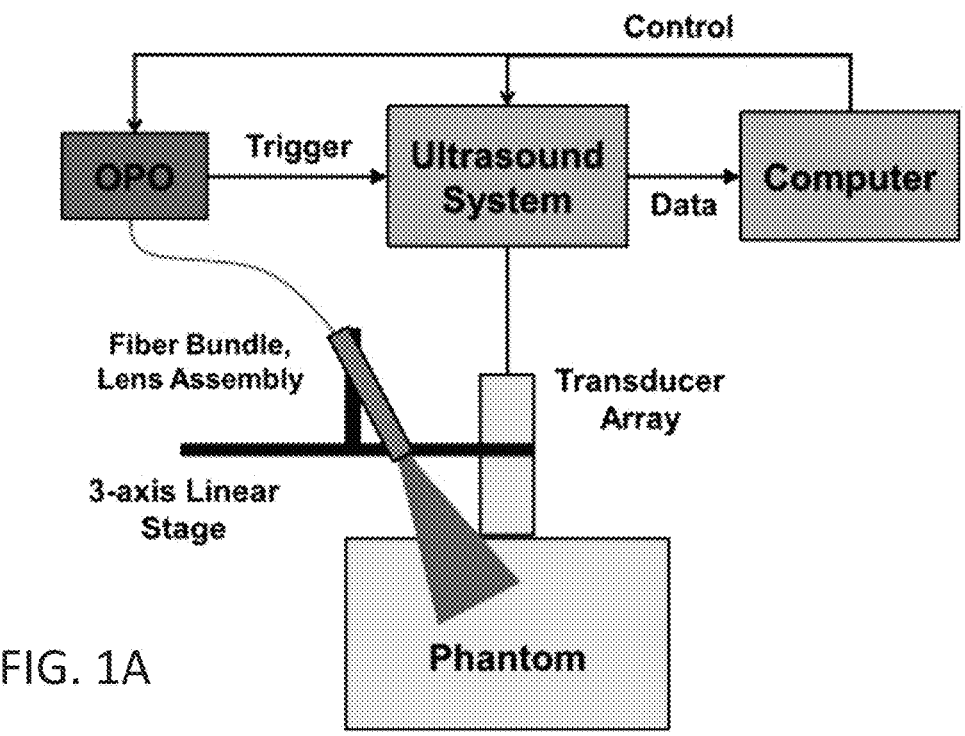
FIGS. 1A and 1B are a set of schematic diagrams illustrating a PAT system for detecting photoacoustic properties of a sample (FIG. 1A), and an exemplary embodiment of fluid channel geometry in a PVCP phantom (FIG. 1B).

Phantom-based test methods are commonly used in medical imaging device development and optimization, system inter-comparison, benchmarking, clinical trial standardization, constancy testing, recalibration, quality assurance, and regulatory evaluation. While there has been significant work on developing phantoms for biophotonic imaging systems, no standardized phantom materials currently exist for photoacoustic imaging.

The majority of materials used for prior PAI and ultrasound phantoms phantoms are comprised of hydrogels including gelatin, agar/agarose gel, polyacrylamide, and polyvinyl alcohol (PVA) cryogels. These gels suffer from poor mechanical strength, short shelf life, diffusion/redistribution of mixed-in particle additives over time, and can also be infiltrated by bacteria and fungi. Further, these hydrogels need to be stored in water or otherwise sealed from the environment to prevent desiccation. Commercial ultrasound phantoms typically improve shelf life and stability by encasing the hydrogel phantom in a protective housing and sealing the housing with a thin acoustic membrane that allows ultrasonic viewing of the gel. However, phantom fabrication quality, robustness to wear, aging, and damage, and total shelf-life or product lifetime would be substantially improved if a tissue-mimicking material with higher mechanical strength and greater temporal stability were available.

PVCP has also been proposed for use to construct phantoms. PVCP phantoms are not made of hydrogels; instead highly plasticized and fused materials are used. Thus, PVCP does not possess the aforementioned limitations of hydrogels. However, prior PVCP phantoms demonstrated poor acoustic properties, with the speed of sound through the prior PVCP phantoms being ~1400 m/s (Spirou et al, Phys Med Biol 50, 2005). In contrast, soft tissues generally have sound speeds from 1450-1570 m/s (see Example 1). Further, Example 1 provides acoustic attenuation data, acquired from 4.0-9.0 MHz, suggesting that prior PVCP phantoms have a lower acoustic attenuation spectrum than many types of soft tissues in this frequency range.

This disclosure provides novel PVCP phantoms that are stable, have biologically-relevant optical and acoustic characteristics, and can be used for standardized assessment of optical and acoustic detection systems, particularly photoacoustic and ultrasound detection systems. In several embodiments, the disclosed PVCP phantoms can be constructed of a PVCP gel comprising a novel combination of PVC and binary plasticizer comprising BBP and DEHA. In contrast to prior PVCP phantoms, the novel combination of materials used in the disclosed phantoms allows for a speed of sound through the phantom of from 1400-1520 m/s, overlapping with tissue-relevant properties, as well as having a tissue-relevant, frequency dependent acoustic attenuation spectrum. Accordingly, the novel combination of PVC and binary plasticizer comprising BBP and DEHA described herein can be used to construct phantoms with surprisingly accurate biologically-relevant acoustic and optical properties. Further, by addition of optical and/or acoustic absorbing or scattering additives, the PVCP formulations can be tuned to mimic the corresponding optical and/or acoustic properties of particular tissue types of interest.

The disclosed phantoms provide an unexpected combination of features that make them particularly suitable for use as phantoms for acoustic and photoacoustic detection systems. While many hydrogel phantoms in the prior art have sound speed tunable from ~1480-1600 m/s, these materials cannot accurately mimic the acoustic properties of fatty tissues, which may have speed of sound from 1425-1475 m/s depending on the relative amount of fatty versus non-fatty tissue. Furthermore, hydrogel phantoms have poor temporal stability due to desiccation over a period of days, and are thus not suitable for long-term use without sufficiently sealing the phantom from the environment (for example, an air tight housing including a thin plastic membrane for allowing a photoacoustic or ultrasound system to interrogate the gel). In contrast, the disclosed PVCP-based phantoms include PVCP gel with a speed of sound between 1400-1520 m/s. Not only does this formulation exhibit more biologically relevant sound speed than prior phantoms, but it provides the ability to fine-tune the sound speed to simulate a range of tissue types. The base PVCP gel exhibits sufficiently low (and spectrally appropriate) acoustic attenuation and optical properties such that by adding a moderate quantity of dyes and particulates it is possible to achieve a range of independently-tunable, biologically-realistic optical and acoustic properties. The fact that a formulation of components could produce phantoms with such realistic, tunable and stable properties—and thus be so uniquely well-suited for use with bi-modal optical/acoustic biomedical devices—represents a very surprising result.

There are also unique benefits to using the disclosed PVCP gel formulations to construct phantoms with multiple components with different optical and/or acoustic properties. A phantom with multiple tissue-mimicking components wherein all components have the same base, but different ratios for each of the constituent chemicals, can provide better optical and acoustic property matching at interfaces, thus reducing the potential for interface artifacts (e.g., reflections). Prior art materials have larger differences in key parameters such as speed of sound and refractive index; thus larger artifacts detrimental to image quality would be produced.

Accordingly, the disclosed PVCP phantoms can be used, for example, for optical, acoustic (such as ultrasound), and photoacoustic (such as PAT) medical device development and optimization, system inter-comparison, benchmarking, clinical trial standardization, constancy testing, calibration, quality assurance, training, education, and regulatory evaluation.

I. Abbreviations
BBP benzyl butyl phthalate
BPC black plastic color
DEGB diethylene glycol dibenzoate
DEHA di(2-ethylhexyl) adipate
DPGB dipropylene glycol dibenzoate
PAI Photoacoustic Imaging
PAM Photoacoustic Microscopy
PAT Photoacoustic Tomography
PVA poly(vinyl) alcohol
PVC poly(vinyl chloride)
PVCP poly(vinyl chloride) plastisol
ROI Region of interest II. Summary Of Terms As used in this application and in the claims, the singular forms "a," "an," and "the" include the plural forms unless the context clearly dictates otherwise. Additionally, the term "includes" means "comprises." The disclosed systems, methods, and apparatus are not limited to any specific aspect or feature or combinations thereof, nor do the disclosed systems, methods, and apparatus require that any one or more specific advantages be present or problems be solved. Any theories of operation are to facilitate explanation, but the disclosed systems, methods, and apparatus are not limited to such theories of operation.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed systems, methods, and apparatus can be used in conjunction with other systems, methods, and apparatus. Additionally, the description sometimes uses terms like "produce" and "provide" to describe the disclosed methods. These terms are high-level abstractions of the actual operations that are performed. The actual operations that correspond to these terms will vary depending on the particular implementation and are readily discernible by one of ordinary skill in the art.

Unless context indicates otherwise, all technical and scientific terms used herein have the same meaning as commonly understood to one of ordinary skill in the art to which this disclosure pertains. Although methods and materials similar or equivalent to those described herein can be used in the practice or testing of the present disclosure, suitable methods and materials are described below. The materials, methods, and examples are illustrative only and not intended to be limiting. In case of conflict, the present specification, including explanations of terms, will control.

About: With reference to a numerical parameter, the term "about" refers to a plus or minus 5% range around the numerical parameter. For example, "about 5%" refers to "4.75% to 5.25%."

Binary Plasticizer: A plasticizer including two liquid plasticizers. In several embodiments, a binary plasticizer can include BBP and DEHA.

Detection: Identification of existence, presence, fact, or characteristics of something. General methods of detection are known to the skilled artisan and may be supplemented with the protocols and devices disclosed herein. In some embodiments, detection includes use of a device to provide structural or functional information, such as an image, a non-spatial distribution (such as an optical spectrum), an individual value, or binary or multi-level indicator of endogenous or exogenous constituent, disease state, or biomarker; or some combination thereof. Detection can include identification of the optical and/or acoustic properties of a phantom as disclosed herein.

Image: A set of data points representative of a spatially resolved parameter, such as a set of spatially resolved values, where each data point corresponds to a value of a parameter (such as ultrasonic signal intensity) in a position. The positions may be comprised within a plane, corresponding to a one-dimensional or two-dimensional image, or they may be distributed across more dimensions, for example three dimensions. Further, each data-point may correspond to a finite area or volume, such as having a finite area or finite volume being assigned to each data point, although the position is described as a mathematically ideal point in space. In several embodiments, an image can be displayed on a screen, for example, for view by a user.

Phantom: A synthetic object that can be measured with a detection/imaging system to evaluate, analyze, and/or calibrate the detection system or device, or for other purposes such as training. Tissue-simulating phantoms that have biologically relevant physical (e.g., optical, acoustic) properties are often used to evaluate medical detection/imaging devices. Phantoms can be used for evaluating system performance or safety. The use of phantoms for the evaluation of medical imaging devices is well established in the scientific literature and international standards. Phantoms are preferred to in vivo or ex vivo tissue for testing and calibrating detection systems and devices as they have well-characterized properties, are more convenient, more temporally and mechanically stable, and provide more consistent results than the living or dead tissue, and can be designed to have inclusions (such as an array of microwires of preselected diameter), for determining image quality characteristics, such as the spatial resolution of a photoacoustic imaging system. Phantom-based test and calibration methods are commonly used in medical imaging device development and optimization, system inter-comparison, benchmarking, clinical trial standardization, constancy testing, recalibration, quality assurance, training, education, and regulatory evaluation. Additionally, the use of phantom-based performance test methods reduces the need to use animal or human studies, reducing risks to human subjects, need for animal sacrifices, and device development and testing costs.

Imaging phantoms are an effective tool for evaluating detection/imaging system performance (e.g., image quality). In several embodiments, a disclosed phantom is an imaging phantom that can be used to test or calibrate a PAI system or an ultrasound imaging system. This may involve fixed measurements or scanning of the phantom for three-dimensional imaging. The imaging phantoms of the present disclosure can be used in several applications for PAI and/or ultrasound imaging, including but not limited to: 1) to facilitate early device development and optimization of instrumentation and software (e.g., image processing) components, 2) to ensure imaging system quality in the manufacturing process and provide end users with qualification of a delivered system; 3) to ensure consistent nominal image system performance over time; 4) to validate re-calibration during servicing, maintenance, and repair of imaging systems with degraded performance; 5) to compare the performance of different imaging systems or similar systems located at different sites, 6) as marketing tools to enable companies to gather objective, quantitative (or qualitative) evidence of imaging system efficacy, and 7) as education tools to train users how to operate an optical or acoustic detection system of interest, 8) to perform dosimetry and safety testing (e.g., temperature measurements with an embedded thermocouple in a phantom), 9) to conduct basic research on optical and acoustic phenomena and mechanisms, and 10) to verify computational models of physical processes in tissue using experimental measurements.

Photoacoustic Imaging (PAI) and Photoacoustic Tomography (PAT): Imaging techniques exploiting the photoacoustic effect (also known as the optoacoustic effect). The terms photoacoustic and optoacoustic are generally interchangeable. In typical PAI methods, very short light pulses produced by a laser or similar light source are delivered over a controlled/specified region in a sample. Some of the light is absorbed in the exposed region and converted to thermal energy, i.e., heat. The resulting rapid heating per pulse causes absorbing material in the region to expand rapidly due to thermal expansion. The resulting sudden motion of the exposed region generates acoustic (ultrasonic) waves that propagate through the sample. These ultrasonic waves are then detected using acoustic transducers placed at the sample surface, and can be interpreted to form an image using conventional ultrasonic imaging methods and apparatus, resulting in reconstructed images whose contrast is based on optical absorption. PAI can achieve penetration depths of 2-5 cm in tissue samples because acoustic attenuation in tissues is much lower than optical attenuation, providing absorption information at much greater depths than pure optical imaging techniques (Wang et al., Science, 335(6075), 1458-1462, 2012).

By obtaining PAI images of multiple sample regions, three-dimensional imaging is possible, and is referred to as Photoacoustic Tomography (PAT). In PAI, image contrast is typically associated with contrast in local optical absorption in the sample. One of the most significant endogenous optical absorbers in tissue is oxy/deoxyhemoglobin present in blood, thus PAT systems are capable of visualizing deep tissue vasculature. Exogenous contrast agents such as bioconjugatable dyes (Erpelding et al., Radiology, 256(1), 102-110, 2010; Kim et al., Biomed Opt Express, 1(1), 278-284, 2010), or nanoparticles (Bouchard et al., PNAS, 106(11), 4085-4089, 2009) may also be used to enhance image contrast. Vascular imaging applications being investigated in the literature include oximetry (Laufer et al., Phys Med Biol, 50(18), 4409-4428, 2005), lymph node detection (Erpelding et al., Radiology, 256(1), 102-110, 2010), and cancer detection, especially mammography (Kruger et al., Med Phys, 37(11), 6096-6100. 2010).

Unless context indicates otherwise, the disclosed embodiments are not limited to any particular method of generating acoustic signals in response a pulsed optical beam.

Optical beams, optical radiation, and light: Propagating electromagnetic radiation at wavelengths between about 200 nm and 3000 nm. The term "optical beam" is used for convenient description and does not imply any particular beam collimation, and as used herein, optical beams can be associated with numerical apertures as large as 1.

Poly(vinyl chloride) plastisol (PVCP) is a suspension of poly(vinyl chloride) resin in a liquid plasticizing agent. Plastisols are a dispersed mixture of fine PVC particles in plasticizer. Smaller-sized PVC particles are preferred for plastisol formulation, rather than the larger, suspension-grade resins better suited for rigid PVC extrusion (such as PVC piping). (See, for example, Nakajima and Harrell, Journal of Colloid and Interface Science 238, 105-115, 2001.) In some embodiments, a commercial dispersion-grade resin with fine particle size (such as Geon 121A available from Mexichem, Inc.) can be used in a PVCP gel to produce a disclosed phantom.

PVCP gel: A stable, non-aqueous polymer gel formed when PVCP made with PVC and appropriate plasticizer (such as BBP and/or DEHA) is hardened (or cured) by heating to temperatures in excess of 170-190° C. to induce gelation/fusion, followed by subsequent cooling to allow hardening of the gel.

Tissue Mimicking Material (TMM): A material that has optical and/or acoustic properties that simulate the corresponding optical and/or acoustic properties of biological tissue from a subject (such as a live human). The disclosed PVCP gel formulations comprising PVC and binary plasticizer including BBP and DEHA are an example of a TMM. Tissue mimicking materials can be used to make a phantom, such as a phantom for calibrating or testing an optical or acoustic detection system, such as an ultrasound imaging system.

Ultrasound: Acoustic signals having frequencies between 10 kHz and 20 GHz.

Ultrasound Imaging: Imaging techniques involving application of ultrasound to a target (such as a region of interest in a human patient) and detection of reflected sound waves to generate an image of the target. Ultrasound imaging techniques and systems are widely used for medical imaging and described, for example, in Tsabo (*Diagnostic Ultrasound Imaging: Inside Out*, $2^{nd}$ Edition, Academic Press, San Diego, 2014).

III. Phantoms

Novel phantoms for assaying, calibrating, and/or testing the performance of an optical or acoustic detection system (such as a photoacoustic imaging system) are provided. The disclosed phantoms are made of a PVCP gel comprising PVC and a binary plasticizer comprising or consisting of BBP and DEHA, as well as additional materials to mimic biological properties. As disclosed in the Examples section, and unlike prior phantom materials, by adding dopant particles to the PVCP gel, the optical and acoustic properties of the phantom may be tuned to simulate the corresponding optical and acoustic properties of many different biological tissues of interest. Thus, such PVCP gels can be used to generate phantoms that enable accurate simulation of many distinct tissue types and compositions that cannot be achieved with other phantom materials. Further, multiple PVCP gels comprising PVC and binary plasticizer comprising or consisting of varying ratios of BBP and DEHA can be made with distinct tissue-specific properties. In several embodiments, the PVCP gels can be molded and incorporated into an phantom to represent an anatomical body region, part, or organ containing multiple tissue types.

The disclosed phantoms comprise a PVCP gel comprising PVC and a binary plasticizer comprising or consisting of BBP and DEHA. In some embodiments, the PVC included in the PVCP gel can be a dispersion grade PVC resin with fine particle size, such as Geon 121A (commercially available from Mexichem, Inc).

In some embodiments, the PVCP gel comprises from 2% to 20% m/m PVC/binary plasticizer. For example the PVCP gel can comprise from 2% to about 10%, from about 5% to about 10%, from about 5% to about 15%, from about 5% to about 20%, from about 7% to about 10%, from about 7% to about 11%, from about 7% to about 12%, from about 8% to about 10%, from about 8% to about 11%, from about 8% to about 12%, from about 9% to about 10%, from about 9% to about 11%, from about 9% to about 12%, from about 10% to about 12%, from about 10% to about 15%, from about 10% to 20%, or from about 15% to 20% m/m PVC/binary plasticizer. In additional embodiments, the PVCP gel can comprise from 2% to 10%, from 5% to 10%, from 5% to 15%, from 5% to 20%, from 7% to 10%, from 7% to 11%, from 7% to 12%, from 8% to 10%, from 8% to 11%, from 8% to 12%, from 9% to 10%, from 9% to 11%, from 9% to 12%, from 10% to 12%, from 10% to 15%, from 10% to 20%, or from 15% to 20% m/m PVC/binary plasticizer. In additional embodiments, the PVCP gel can comprise about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20%, m/m PVC/binary plasticizer. In additional embodiments, the PVCP gel can comprise 2%, 3%, 4%, 5%, 6%, 7%, 8%, 9%, 10%, 11%, 12%, 13%, 14%, 15%, 16%, 17%, 18%, 19%, or 20%, m/m PVC/binary plasticizer.

In several embodiments, the binary plasticizer included in the PVCP gel can be a liquid plasticizer, for example comprising or consisting of a mixture of BBP and DEHA. BBP and DEHA are available from several different commercial sources (for example, Sigma Aldrich, TCI America, Eastman Chemical Company, Univar, Corp). BBP and DEHA are liquid plasticizers that can be mixed together in varying ratios to form the binary plasticizer used in the disclosed phantoms. Any appropriate method of mixing BBP and DEHA to form the binary plasticizer can be used; exemplary methods are provided in the examples.

The concentration of PVC in a PVCP gel can be altered as needed to increase or decrease acoustic attenuation of the PVCP gel, as well as gel mechanical stiffness and speed of sound. Increased PVC concentration leads to increased acoustic attenuation of the PVCP gel, as well as increased gel mechanical stiffness. As disclosed herein, acoustic attenuation can also be affected by the ratio of BBP to DEHA in the binary plasticizer. Thus, the concentration of PVP in the PVCP gel, as well as the ratio of BBP to DEHA in the binary plasticizer can be altered to modify the acoustic and/or optical properties of the PVCP gel as needed to mimic a selected tissue.

In some embodiments, the binary plasticizer included in the PVCP gel comprises or consists of a mixture of BBP and DEHA at a volume ratio of 1000:1 to 1:1000. For example, the binary plasticizer can comprise or consist of a mixture of BBP and DEHA at a volume ratio of 100:1 to 1:100. In some embodiments, the binary plasticizer can comprise or consist of a mixture of BBP and DEHA at a volume ratio of about 99:1, about 95:5, about 90:10, about 85:15, about 80:20, about 75:25, about 70:30, about 60:40, about 50:50, about 40:60, about 30:70, about 25:75, about 10:90, or about 1:99. In some embodiments, the binary plasticizer can comprise or consist of a mixture of BBP and DEHA at a volume ratio of 99:1, 95:5, 90:10, 85:15, 80:20, 75:25, 70:30, 60:40, 50:50, 40:60, 30:70, 25:75, 10:90, or 1:99.

Additives

The PVCP gel can further comprise additives with optical absorbing, optical scattering, acoustic absorbing, and/or acoustic scattering properties to modify the acoustic and/or optical properties of the PVCP gel to mimic a selected tissue. The additives are typically added to the PVC/binary plasticizer mixture prior to heating to form the PVCP gel.

In some embodiments, the PVCP gel can include one or more acoustic scattering additives, such as glass microparticles (for example, silica microspheres or ground silica powder) with a mean particle size less than the acoustic wavelength of interest (such as less than 100 microns). By adding the glass microparticles, acoustic scattering can be imparted to the PVCP gel to increase acoustic attenuation and provide acoustic backscattering, which generates speckle, or texture, in both ultrasound and photoacoustic images. In some embodiments, the glass microparticles can have a mean diameter of from 10 to 100 μm. In additional embodiments, the glass microparticles can have a mean diameter of from 30-60 μm. In some embodiments, the PVCP gel can comprise glass microparticles at a concentration range of from 1-300 mg/mL, such as from 1-200 mg/mL, from 10-100 mg/mL, or from 25-50 mg/mL. In some embodiments, the PVCP gel can comprise glass microparticles at a concentration of about 5 mg/mL, about 10 mg/mL, about 15 mg/mL, about 20 mg/mL, about 25 mg/mL, about 30 mg/mL, about 35 mg/mL, about 40 mg/mL, about 45 mg/mL, about 50 mg/mL, about 60 mg/mL, about 70 mg/mL, about 80 mg/mL, about 90 mg/mL, about 100 mg/mL, about 125 mg/mL, about 150 mg/mL, about 175 mg/mL, or about 200 mg/mL. In some embodiments, the PVCP gel can comprise glass microparticles at a concentration of 5 mg/mL, 10 mg/mL, 15 mg/mL, 20 mg/mL, 25 mg/mL, 30 mg/mL, 35 mg/mL, 40 mg/mL, 45 mg/mL, 50 mg/mL, 60 mg/mL, 70 mg/mL, 80 mg/mL, 90 mg/mL, 100 mg/mL, 125 mg/mL, 150 mg/mL, 175 mg/mL, or 200 mg/mL.

In some embodiments, the PVCP gel can include one or more optical absorbing additives. Exemplary optical absorbing additives include dyed polymer microparticles, dyed glass microparticles, metal particles, metal microparticles, carbon black, and black plastic colorant (BPC). The PVCP gel can include the optical absorbers at an appropriate concentration for the PVCP gel to mimic the optical properties of a selected tissue.

BPC typically is a composition of carbon black dispersed in liquid plasticizer or PVC resin and can be acquired commercially (for example, from M-F Manufacturing Co.). Use of BPC as an optical absorbing additive in prior PVCP gel-based phantoms has been described (see, e.g., Spirou et al., Phys Med Biol, 50(14), N141-N153, 2005, and Bohndiek et al., PloS One, 8(9), 2013, each of which is incorporated by reference herein). In the disclosed embodiments, the BPC can be added to the PVC/binary plasticizer mixture prior to heating. In some embodiments, the PVCP gel can comprise BPC at a concentration of from 0.0001% to 0.1% v/v BPC/binary plasticizer. For example the PVCP gel can comprise BPC at a concentration of from 0.001% to 0.05% v/v BPC/binary plasticizer, from 0.001% to 0.01% v/v BPC/binary plasticizer, from 0.002% to 0.004% v/v BPC/binary plasticizer, from 0.002% to 0.008% v/v BPC/binary plasticizer, from 0.002% to 0.015% v/v BPC/binary plasticizer, from 0.004% to 0.008% v/v BPC/binary plasticizer, from 0.004% to 0.015% v/v BPC/binary plasticizer, from 0.008% to 0.02% v/v BPC/binary plasticizer, or from 0.008% to 0.015% v/v BPC/binary plasticizer. In some embodiments, the PVCP gel can comprise BPC at a concentration of about 0.002% v/v BPC/binary plasticizer, about 0.004% v/v BPC/binary plasticizer, about 0.006% v/v BPC/binary plasticizer, about 0.008% v/v BPC/binary plasticizer, about 0.010% v/v BPC/binary plasticizer, about 0.012% v/v BPC/binary plasticizer, about 0.015% v/v BPC/binary plasticizer, or about 0.02% v/v BPC/binary plasticizer. In some embodiments, the PVCP gel can comprise BPC at a concentration of 0.002% v/v BPC/binary plasticizer, 0.004% v/v BPC/binary plasticizer, 0.006% v/v BPC/binary plasticizer, 0.008% v/v BPC/binary plasticizer, 0.010% v/v BPC/binary plasticizer, 0.012% v/v BPC/binary plasticizer, 0.015% v/v BPC/binary plasticizer, or 0.02% v/v BPC/binary plasticizer, In some embodiments, the PVCP gel can include one or more optical scattering additives. Exemplary optical scattering additives include barium sulfate, silica microparticles having a diameter less than 10 μm, and titanium dioxide ($TiO_2$, such as anatase, such as anatase $TiO_2$ with mean particle/agglomerate diameter of 25-1000 nm, such as 500 to 600 nm). The PVCP gel can include the one or more optical scattering additives at an appropriate concentration for the PVCP gel to mimic the optical properties of a selected tissue.

In some embodiments, the PVCP gel can include $TiO_2$ as an optical scattering additive. For example, the PVCP gel can comprise $TiO_2$ at a concentration range of from 0.1-5 mg/mL, such as from 0.5-5 mg/mL, from 1-5 mg/mL, from 0.5-2 mg/mL, from 0.5-3 mg/mL, from 1-3 mg/mL, or from 1-2 mg/mL. In some embodiments, the PVCP gel can comprise $TiO_2$ at a concentration of about 0.5 mg/mL, about 0.8 mg/mL, about 1 mg/mL, about 1.25 mg/mL, about 1.5 mg/mL, about 1.75 mg/mL, about 2.0 mg/mL, about 2.25 mg/mL, about 2.5 mg/mL, about 2.75 mg/mL, about 3 mg/mL, about 4 mg/mL, or about 5 mg/mL. In some embodiments, the PVCP gel can comprise $TiO_2$ at a concentration of 0.5 mg/mL, 0.8 mg/mL, 1 mg/mL, 1.25 mg/mL, 1.5 mg/mL, 1.75 mg/mL, 2.0 mg/mL, 2.25 mg/mL, 2.5 mg/mL, 2.75 mg/mL, 3 mg/mL, 4 mg/mL, or 5 mg/mL.

Non-limiting examples of other additives that may be incorporated into the PVCP gel of a disclosed phantom include air-release agents, viscosity reducers, and other classes of commercial PVCP additives.

In some embodiments, the phantom comprises a PVCP gel comprising 7-12% m/m PVC/binary plasticizer wherein the binary plasticizer comprises or consists of BBP and DEHA at a volume ratio of from 25/75 to 90/10 BBP/DEHA; 0-100 mg/mL glass microparticles; 0-3 mg/mL titanium dioxide, and 0-0.5% v/v black plastic colorant (BPC). In some embodiments, the phantom comprises a PVCP gel comprising 7-12% m/m PVC/binary plasticizer wherein the binary plasticizer comprises or consists of BBP and DEHA at a volume ratio of from 25/75 to 90/10 BBP/DEHA; 0-100 mg/mL glass microparticles; 0-3 mg/mL titanium dioxide, and 0-0.1% v/v black plastic colorant (BPC).

In several embodiments, the phantom comprises a PVCP gel formulated to mimic the photoacoustic properties of a particular tissue type, such as fatty breast tissue, breast tissue with moderate relative fat/parenchyma content, parenchymal breast tissue, skin, abdominal fat, brain, liver, or skeletal muscle. The speed of sound in such phantoms is of superior biological relevance than that of prior PVCP phantoms (which have a speed of sound of approximately of 1400 m/s with poor tenability, and which have acoustic attenuation that can only mimics highly fatty tissues).

In some embodiments, the phantom comprises a PVCP gel formulated to mimic fatty breast tissue. For example, the phantom comprises a PVCP gel comprising from 7-12% m/m PVC/binary plasticizer (such as about 10% m/m PVC/binary plasticizer), binary plasticizer comprising BBP and DEHA at a volume ratio of about 30 to about 70, about 25 mg/mL silica microparticles, about 1.5 mg/mL titanium dioxide. In another example, the phantom comprises a PVCP gel comprising from 7-12% m/m PVC/binary plasticizer (such as from 8-9% m/m PVC/binary plasticizer, for example, about 8.4% m/m PVC/binary plasticizer), binary plasticizer comprising BBP and DEHA at a volume ratio of about 40 to about 60 (such as about 42 to about 58), from 5-15 mg/ml silica microspheres (such as about 10 mg/mL silica microparticles), and from 2.1 to 2.4 mg/mL titanium dioxide (such as from 2.2 to 2.3 mg/mL titanium dioxide, for example about 2.29 mg/mL titanium dioxide or about 2.293 mg/mL titanium dioxide).

In some embodiments, the phantom comprises a PVCP gel formulated to mimic breast tissue with moderate relative fat/parenchyma content. For example, the phantom comprises a PVCP gel comprising from 7-12% m/m PVC/binary plasticizer (such as about 10% m/m PVC/binary plasticizer), binary plasticizer comprising BBP and DEHA at a volume ratio of about 75 to about 25, about 50 mg/mL silica microparticles, about 1.75 mg/mL titanium dioxide, and about 0.002% v/v BPC. In another example, the phantom comprises a PVCP gel comprising from 7-12% m/m PVC/binary plasticizer (such as about 10% m/m PVC/binary plasticizer), binary plasticizer comprising BBP and DEHA at a volume ratio of about 75 to about 25, about 30 mg/mL silica microparticles, about 2.0 mg/mL titanium dioxide, and about 0.002% v/v BPC. In another example, the phantom comprises a PVCP gel comprising from 7-12% m/m PVC/binary plasticizer (such as from 8-9% m/m PVC/binary plasticizer, for example, about 8.6% m/m PVC/binary plasticizer), binary plasticizer comprising BBP and DEHA at a volume ratio of about 85 to about 15 (such as about 87 to about 13), from 20-40 mg/ml silica microspheres (such as about 30 mg/mL silica microparticles), and from 2.8 to 3.1 mg/mL titanium dioxide (such as from 2.9 to 3.0 mg/mL titanium dioxide, for example about 2.95 mg/mL titanium dioxide or about 2.947 mg/mL titanium dioxide).

In some embodiments, the phantom comprises a PVCP gel formulated to mimic parenchymal breast tissue. For example, the phantom comprises a PVCP gel from 7-12% m/m PVC/binary plasticizer (such as about 10% m/m PVC/binary plasticizer), binary plasticizer comprising BBP and DEHA at a volume ratio of about 90 to about 10, about 100 mg/mL silica microparticles, about 2.5 mg/mL titanium dioxide, and about 0.002% v/v BPC.

In some embodiments, the phantom comprises a PVCP gel formulated to mimic skin. For example, the phantom comprises a PVCP gel comprising from 7-12% m/m PVC/binary plasticizer (such as about 10% m/m PVC/binary plasticizer), binary plasticizer comprising BBP and DEHA at a volume ratio of about 99 to about 1, about 200 mg/mL silica microparticles, about 2.5 mg/mL titanium dioxide, and about 0.008% v/v BPC.

In some embodiments, the phantom comprises a PVCP gel formulated to mimic abdominal fat. For example, the phantom comprises a PVCP gel comprising from 7-12% m/m PVC/binary plasticizer (such as about 10% m/m PVC/binary plasticizer), binary plasticizer comprising BBP and DEHA at a volume ratio of about 40 to about 60, no silica microparticles, about 1.5 mg/mL titanium dioxide. In some such embodiments, the PVCP gel in the phantom does not comprise BPC.

In some embodiments, the phantom comprises a PVCP gel formulated to mimic brain tissue. For example, the phantom comprises a PVCP gel comprising from 7-12% m/m PVC/binary plasticizer (such as about 8% m/m PVC/binary plasticizer), binary plasticizer comprising BBP and DEHA at a volume ratio of about 90 to about 10, about 25 mg/mL silica microparticles, about 2.5 mg/mL titanium dioxide. In some such embodiments, the PVCP gel in the phantom does not comprise BPC.

In some embodiments, the phantom comprises a PVCP gel formulated to mimic liver. For example, the phantom comprises a PVCP gel comprising from 7-12% m/m PVC/binary plasticizer (such as about 8% m/m PVC/binary plasticizer), binary plasticizer comprising BBP and DEHA at a volume ratio of about 75 to about 25, about 50 mg/mL silica microparticles, about 1.5 mg/mL titanium dioxide, and about 0.004% v/v BPC.

In some embodiments, the phantom comprises a PVCP gel formulated to mimic skeletal muscle. For example, the phantom comprises a PVCP gel comprising from 7-12% m/m PVC/binary plasticizer (such as about 8% m/m PVC/binary plasticizer), binary plasticizer comprising BBP and DEHA at a volume ratio of about 75 to about 25, about 100 mg/mL silica microparticles, about 2.0 mg/mL titanium dioxide, and about 0.012% v/v BPC.

In some embodiments, the phantom comprises a PVCP gel including one or more heat stabilizers, such as liquid heat stabilizer. The heat stabilizer is typically added to the PVC/binary plasticizer mixture prior to heating to form the PVCP gel. Exemplary liquid heat stabilizers for use with the disclosed phantoms include stearates, organotin stabilizers, and mixed-metal stabilizers, for example, those based on cadmium, zinc, or barium intermediates. In some embodiments, the phantom comprises a plastisol gel comprising about 1% v/v liquid heat stabilizer/binary plasticizer.

Inclusions/Targets

One or more heterogeneous inclusions or targets can be included in the disclosed phantom to be used in calibrating or testing the performance of an optical or acoustic detection system, such as a PAI system or an ultrasonic imaging system. For example, phantoms incorporating targets/inclusions may be used to evaluate the image quality of a PAI system. The heterogeneous inclusions or targets are typically made of a material designed and/or selected to withstand the high temperature (e.g. heat resistant to ~150-200 □C) used to induce the gel phase of the PVC/binary plasticizer mixture. Non-limiting examples of suitable materials include thin filaments such as metal wires and nylon suture wires for sub-resolution targets, solid inclusions of PVCP gel with differing properties from surrounding PVCP, and fluid channels or embedded tubing injected with absorptive dye solutions.

Arrays of heterogeneous inclusions or targets can be used to quantitatively and objectively assess image quality of an optical or acoustic detection system, such as a photoacoustic imaging system. There are multiple uses for such an array, including measurement of axial resolution, lateral resolution, elevational resolution, spatial measurement accuracy, sensitivity, signal-to-noise ratio, dynamic range, image uniformity, distortion, and image artifacts.

In some embodiments, one or more filaments (such as an array of regularly spaced filaments) may be embedded in the PVCP gel to produce a series of targets for the purpose of measuring spatial resolution (in the axial, lateral, and elevational directions), spatial distance measurement accuracy, image uniformity, and geometric distortion, of a detection system, such as a PAI system. Array targets are desired which produce high photoacoustic signal, but can withstand the high temperatures during cast-molding with PVCP. These filaments may be metal wires, such as aluminum, nickel, steel, or tungsten, or polymeric materials, including dyed (e.g. blue, black) nylon suture wire. Monofilament sutures can be used as point targets for imaging applications. Filament thickness may range from 30 μm to 1 mm. Data presented in the Examples Our presented data has used filaments down to such as about 30 μm diameter wires or larger wires with a 0.5-1 mm diameter.

In some embodiments, one or more solid inclusions (such as an array of regularly spaced solid inclusions) may be embedded within the PVCP gel. Typically the solid inclusion has different optical and/or acoustic properties compared to surrounding PVCP gel. By varying inclusion size, depth, and absorption strength, quantitative analysis can provide performance metrics such as image penetration depth, contrast-to-noise ratio, signal-to-noise ratio, uniformity within the image plane, low-contrast detectability, image artifacts, and sensitivity, of a detection system, such as a PAI system. Non-limiting examples of materials that can be used for the solid include PVCP gels, other gels (such as plastisols, hydrogels, or polymer gels) capsules filled with the other gels, and metal ball bearings. In some embodiments, the solid inclusions be made of a PVCP gel comprising 7-12% m/m PVC/binary plasticizer wherein the binary plasticizer comprises or consists of BBP and DEHA at a volume ratio of from 25/75 to 90/10 BBP/DEHA; 0-100 mg/mL glass microparticles; 0-3 mg/mL titanium dioxide, and 0-0.5% v/v black plastic colorant (BPC). In some embodiments, the solid inclusions be made of a PVCP gel comprising 7-12% m/m PVC/binary plasticizer wherein the binary plasticizer comprises or consists of BBP and DEHA at a volume ratio of from 25/75 to 90/10 BBP/DEHA; 0-100 mg/mL glass microparticles; 0-3 mg/mL titanium dioxide, and 0-0.1% v/v black plastic colorant (BPC). The solid inclusions can have higher, lower, or equal optical and/or acoustic properties relative to a surrounding phantom medium. In some embodiments, the solid inclusions can have different acoustic properties from the background PVCP to simulate image artifacts due to mismatched speed of sound and tissue boundaries.

In some embodiments, one or more fluid channels (such as an array of regularly spaced fluid channels) may be used to enable contrast-detail analysis with liquid solutions containing light-absorbing molecules. Non-limiting examples of methods of forming fluid channels include 1) suspending metal wires/rods and cast-molding PVCP around them, then withdrawing the wires from the cured PVCP, or 2) embedding transparent lengths of tubing in PVCP. After the fluid channels are formed in the PVCP gel, they can be filled with the liquid solutions containing optical or acoustic absorbing and/or scattering molecules. By varying fluid channel size and depth, and the absorption/scattering strength of any injected fluid, quantitative analysis can provide performance metrics such as image penetration depth, contrast-to-noise ratio, signal-to-noise ratio, uniformity within the image plane, low-contrast detectability, image artifacts, and sensitivity, of a detection system, such as a PAI system.

Non-limiting examples of absorbing molecules that can be included in a liquid solution injected into a fluid channel include biological molecules such as oxyhemoglobin, deoxyhemoglobin, methemoglobin, and carboxyhemoglobin, as well as exogenous molecules such as nanoparticles, cyanine dyes, and methylene blue. Additional examples of absorbing molecules that can be included in the liquid injected into the fluid channel include chromophores, fluorophores, and/or photosensitizers, including but not limited to gold nanoparticles (nanoshells, nanorods), indocyanine green, other cyanine dyes, fluorescein, Cy5, Cy7, protoporphyrin IX, and bioconjugated fluorescent tags and biomarkers. After injection of the liquid solution, the fluid channels can be sealed shut to prevent changes in liquid solutions due to environmental effects.

The phantom can also include one or more complex inclusions embedded within the PVCP gel, such as a tumor simulator (e.g., a solid inclusion simulating tumor tissue surrounded by liquid and/or differing solid inclusions that simulate the tumor microenvironment and vasculature), or one or more channels simulating complex vasculature.

Phantom Shape & Manufacture

Figure 1B:
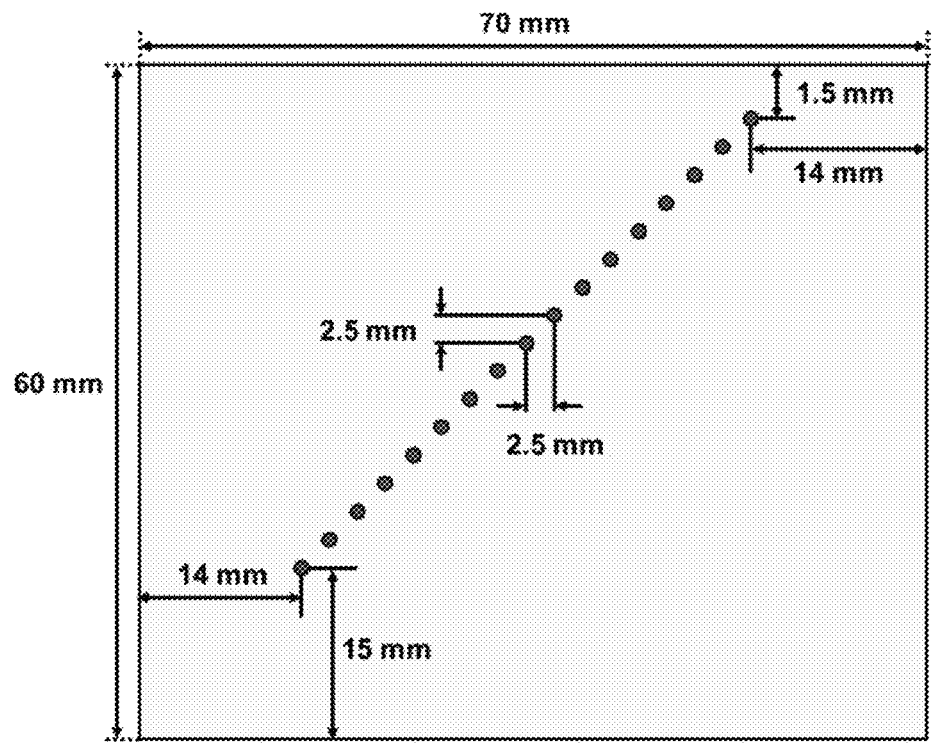

The disclosed phantoms can have any shape appropriate for the intended use. Typically the phantom is cast-molded from the disclosed PVCP gel into a particular pre-selected shape of interest. For example, the PVCP gel included in the phantom can be molded into a cube, cuboid, sphere, ellipsoid, or cylinder shape. FIGS. 1B, 12, 13 and 33 show illustrative embodiments of the disclosed phantoms having a cubical geometry. FIG. 1B illustrates a disclosed phantom having a cubical shape that is approximately 6 cm high, 7 cm wide and 7 cm deep; however, different shapes and sizes can also be used.

In some embodiments, the phantom can contain multiple layers of PVCP gels made with differing properties, for example to simulate the optical or acoustic properties of heterogeneous tissue. FIG. 13 shows a cross sectional view of an exemplary phantom that simulates breast tissue. The phantom has a lower section made of PVCP gel that simulates the optical and acoustic properties of parenchymal breast tissue and an upper section that simulates the optical and acoustic properties of breast tissue with moderate relative fat/parenchyma content. The two sections are separated by an undulating surface similar to that found between parenchymal breast tissue and breast tissue with moderate relative fat/parenchyma content (FIG. 13D). As illustrated in FIG. 13, the phantom can contain one or more (such as an array) of equally distributed filaments (such as microwires) or tubes for testing and calibration purposes. The phantom has a cubical shape, although any suitable shape can be used.

Figure 33A:
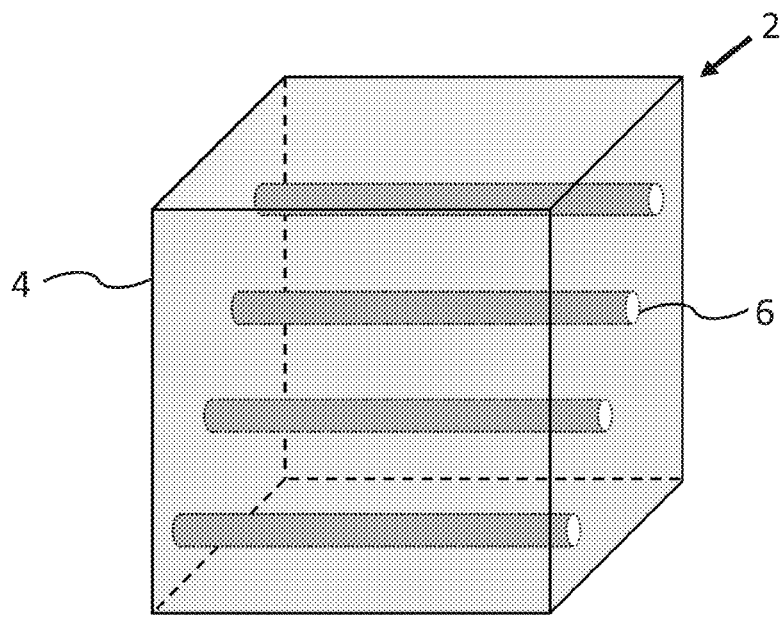
Figure 33B:
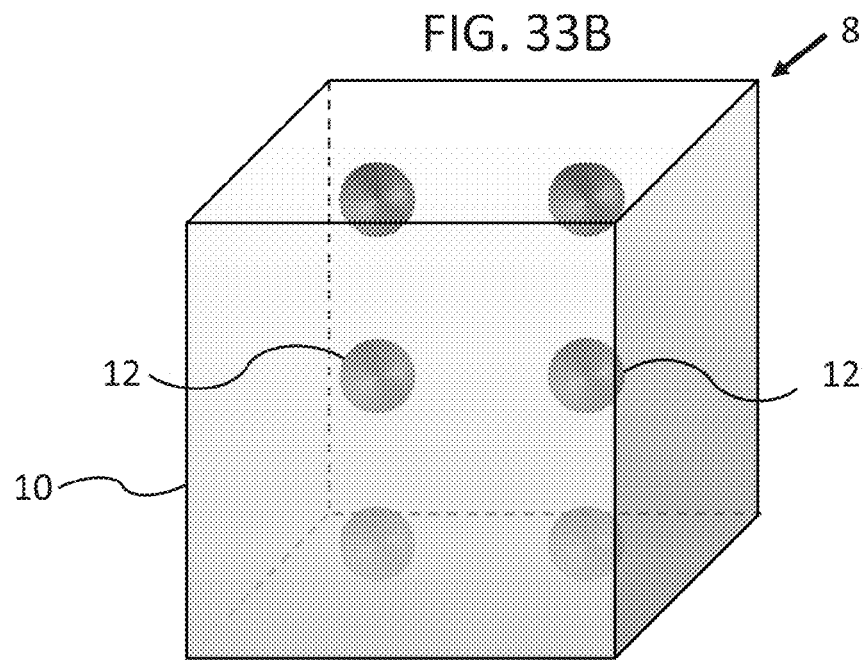

Additional embodiments of PVCP phantoms are illustrated in FIGS. 33A-33D. In FIG. 33A, phantom 2 comprises a cubical shape and is constructed of cured PVCP gel 4 (which can be made of any combination of PVC and binary plasticizer and additives disclosed herein to mimic a tissue of interest). The PVCP gel 4 contains an array of embedded filaments 6, and can be used to with an optical and/or acoustic detection system, such as a photoacoustic imaging system or ultrasound imaging system, as described herein (for example, for calibration, testing, or training purposes). The array of filaments can have any suitable arrangement and/or number of filaments. In several embodiments, the filaments are evenly spaced throughout the phantom. FIG. 33B shows a corresponding PVCP phantom 8 constructed of cured PVCP gel 10, which can be made of any combination of PVC and binary plasticizer and additives disclosed herein to mimic a tissue of interest. PVCP phantom 8 contains an array of embedded spherical inclusions 12, and can be used to calibrate and test the functionality of an optical and/or acoustic detection system, such as a photoacoustic imaging system or ultrasound imaging system imaging system, as described herein (for example, for calibration, testing, or training purposes). The array of spherical inclusions can have any suitable arrangement and/or number of inclusions. In some embodiments, the spherical inclusions can be made of PVCP gel of differing properties compared to that of the gel 10.

Figure 33D:
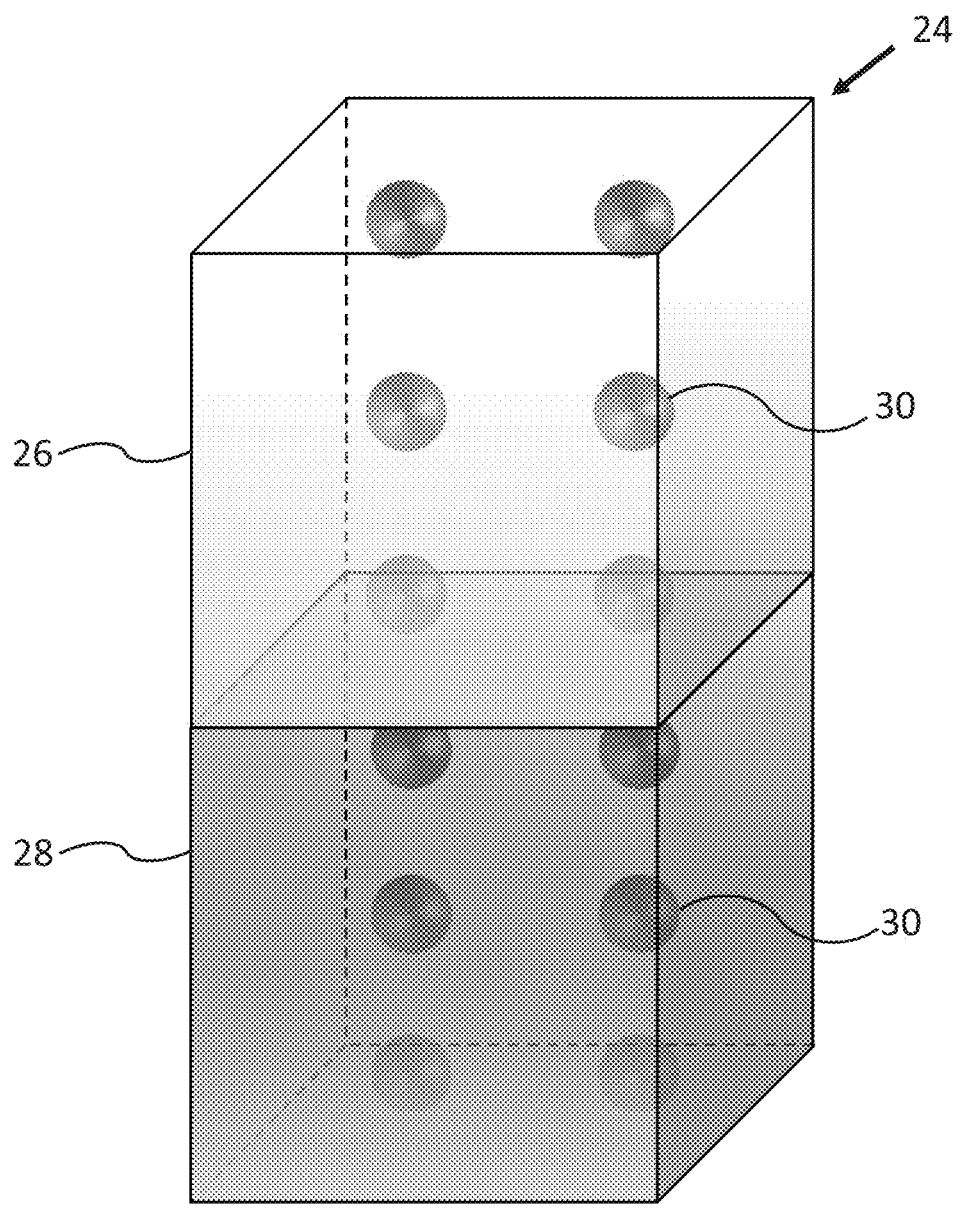

FIGS. 33C and 33D illustrate embodiments of PVCP phantoms having multiple layers of PVCP gel with different properties, into which arrays of inclusions have been embedded. In FIG. 33C, phantom 14 comprises a rectangular cuboid shape and is constructed of an upper cured PVCP gel 16 (which can be made of any combination of PVC and binary plasticizer and additives disclosed herein to mimic a tissue of interest) and a lower cured PVCP gel 18 (which can be made of any combination of PVC and binary plasticizer and additives disclosed herein to mimic a tissue of interest that is different from that of PVCP gel 16). The PVCP gels 16 and 18 contain an array of embedded filaments 20, and can be used with an optical and/or acoustic detection system, such as a photoacoustic imaging system or ultrasound imaging system, as described herein (for example, for calibration, testing, or training purposes). The array of filaments can have any suitable arrangement and/or number of filaments. In FIG. 33C, the filaments are embedded in both PVCP gels 16 and 18; however, the multilayered PVCP phantom can have inclusions or targets embedded in just one layer, or more than one, but not all layers (in the case of phantoms with three or more layers of differing PVCP gel layers). The filaments can be evenly spaced throughout the phantom as shown for phantom 14, or not evenly spaced. The interface 22 between the upper and lower PVCP gels 16 and 18 of the phantom 14 can be planar (as shown in FIG. 33). Alternatively, in some embodiments the interface 22 can have a non-planar shape, for example an undulating shape as shown for the embodiment of the phantom illustrated in FIG. 13. FIG. 33D shows a corresponding PVCP phantom 24 constructed of an upper cured PVCP gel 26 (which can be made of any combination of PVC and binary plasticizer and additives disclosed herein to mimic a tissue of interest) and a lower cured PVCP gel 28 (which can be made of any combination of PVC and binary plasticizer and additives disclosed herein to mimic a tissue of interest that is different from that of PVCP gel 26). The PVCP gels 24 and 26 contain an array of embedded spherical inclusions 30, and can be used with an optical and/or acoustic detection system, such as a photoacoustic imaging system or ultrasound imaging system as described herein (for example, for calibration, testing, or training purposes). The array of spherical inclusions can have any suitable arrangement and/or number of inclusions. In some embodiments, the spherical inclusions can be made of PVCP gel of differing properties compared to that of the gels 26 and 28.

Although not pictured in FIG. 33, in some embodiments the PVCP phantom can contain more than one type of inclusion, such as an array of filaments (for example metal microwires) as well as one or more spherical inclusions.

In some embodiments, the PVCP gel included in the phantom can be molded into the shape of a body part or tissue of interest. In some embodiments, multiple PVCP gels with tissue-specific properties can be molded into shapes representing different parts or tissues of a body region of interest containing multiple organs and/or tissue types (such as a breast) and then incorporated into a single phantom. For example, phantoms representing complex biological organs, body parts, systems, and even small organisms (such as a mouse) can be generated by constructing the phantom using a plurality of PVCP gels comprising PVC and a binary plasticizer comprising or consisting of BBP and DEHA, with each gel in the plurality modified as needed with additives and/or inclusions to simulate a particular tissue or component of the organ, body part, system, or small organism.

Compositions including poly(vinyl chloride) (PVC) and a binary plasticizer comprising or consisting of BBP and DEHA are also provided. The compositions can include the components of any of the PVCP gels discussed above. In several embodiments, the compositions can be used to make the PVCP gel included in the disclosed phantom.

In some embodiments a method of producing the phantom is provided, the method comprising providing a composition including the components of any of the PVCP gels discussed above, and forming the composition into the shape of the phantom. For example, the composition can be heated to a molten gel stage (such as 150-200 $\square$C), pouring the molten gel into a cast mold and allowing the composition to cool. In some embodiments wherein the phantom has one or more embedded inclusions or targets, the inclusion or target can be included in the mold into which the molten gel is poured. In some embodiments wherein the phantom has one or more fluid channels, the fluid channels can be formed by including one or more retractable wires in the mold, and then retracting the wires from the mold after the gel has cooled to a solid gel phase to form the fluid channels (see FIGS. 12A and 12B, which show a mold with retractable wires (12A) and a phantom with fluid channels made using the mold (12B).

IV. Optical And Acoustic Detection Systems

The disclosed phantoms provide realistic simulations of the optical and acoustic properties of tissue. Accordingly, the phantoms can be used with any optical or acoustic detection system where it is desirable to use a phantom that simulates the optical and/or acoustic properties of a tissue or organ, for example, to calibrate or test the performance of the detection system. Non-limiting examples of optical and acoustic detection systems for use with the disclosed phantoms are discussed below.

Photoacoustic Detection Systems

This section provides a description of exemplary photoacoustic detection systems with which the disclosed phantoms can be used. Photoacoustics is an emerging technology with clinical imaging and sensing applications. By irradiating tissues with pulsed light, thermoacoustic waves are generated in absorptive tissue regions, which can be collected by acoustic transducers. By varying the optical wavelength (Photoacoustic Spectroscopy), multispectral data can be used to sense and isolate absorption features of different tissue components. Use of a single stationary transducer results in a photoacoustic sensor device, where the received acoustic signal is correlated to tissue light absorption. By mechanically or electronically scanning one or more transducers, an image can be produced, giving rise to PAI (also known as optoacoustic imaging). Due to high absorption of endogenous hemoglobin in blood, vasculature can be sensed and imaged noninvasively at depths down to 4-6 centimeters (Wang and Hu, Science, 335(6075), 1458-1462, 2012), much deeper than the penetration depth of optical imaging systems based on light transport alone (with the possible exception of diffuse optical tomography, which offers similar penetration but worse resolution). Thus, PAI can provide information on optical absorption contrast, which pure ultrasound cannot provide, at greater depths than pure optical imaging. One application of PAI using endogenous contrast is cancer detection, especially mammography. Exogenous contrast agents such as methylene blue, indocyanine green, or nanoparticles may also be administered for sensing and imaging applications such as cancer detection and lymph flow imaging. Some of the most promising applications of PAI include breast imaging, cerebrovascular imaging, sentinel lymph node mapping, intravascular plaque detection, benchtop and in vivo microscopy and spectroscopy, glucose sensing/monitoring, functional neuroimaging, tissue oximetry, vascular imaging, and molecular imaging for enhanced sensing/interrogation of targeted tissues, including cancerous lesions (Wang, *Med Phys* 2008) and Yao *Contrast Media Mol Imaging* 2011).

Generally, PAI systems are classified into two types: Photoacoustic Computed Tomography (PAT) and Photoacoustic Microscopy (PAM) (Wang and Hu, Science, 335 (6075), 1458-1462, 2012). PAT is well-suited for macroscale imaging over wide fields of view to depths of 4-5 cm, while PAM is capable of performing microscopic imaging of small blood vessel networks in shallow tissues (~1-5 mm depths).

In PAT systems, the primary design parameters are the number and arrangement of acoustic transducers, transducer frequency range, and light illumination pattern. Two commercial systems sold for small animal research are the VisualSonics Vevo LAZR and Endra Nexus 128 (see Bohndiek et al., Plos One, 8(9), 2013). These systems highlight two general types of PAT systems: systems using a linear array ultrasound transducer and systems using a large-aperture array of transducers. Additional exemplary PAT and PAM systems include those provided, for example, in Erpelding et al. (Radiology, 256(1), 102-110, 2010) and; Kim et al. (Biomed Opt Express, 1(1), 278-284, 2010) each of which is incorporated by reference herein and which describe a PAT system using a clinical ultrasound system and transducer; Ermilov et al. (J Biomed Opt, 14(2), 2009, which is incorporated by reference herein) which describes a PAT mammography system using C-shaped transducer array; Dima et al. (Opt Express, 20(22), 25044-25057, 2012, which is incorporated by reference herein) which describes a comparison of linear and curved arrays that may be rotated around a target; Manohar et al. (Phys Med Biol, 50(11), 2543-2557, 2005, which is incorporated by reference herein) which describes a PAT mammography systems using plate array; Wang et al. (Sci Rep 4, 2014, which is incorporated by reference herein) which describes an Intravascular PAI probe for intravascular plaque detection and representative PAI images taken using such a probe; and Wang and Hu (Science, 335(6075), 1458-1462, 2012, which is incorporated by reference herein) which describes optical-resolution photoacoustic microscopy (OR-PAM) and acoustic-resolution photoacoustic microscopy (AR-PAM).

One clinical application of PAT is mammography, since deep penetration is required to interrogate breast lesions. Many PAT mammography systems utilize a standard clinical ultrasound system and linear array transducer to collect acoustic signals. Light is delivered to the tissue beneath the transducer using fiberoptic bundles arranged to provide uniform illumination over the entire transducer/tissue area. Water or acoustic coupling gel is often introduced between the transducer and sample to ensure good transmission of acoustic signals from the tissue to the transducer. Other types of systems utilize a single acoustic transducer that is mechanically scanned around a target sample immersed in a water bath (Xia et al., J Biomed Opt, 16(7), 2011; Bouchard et al., PNAS, 106(11), 4085-4089, 2009). Alternative approaches utilize a large number of transducers arranged at multiple points around a target in 360 degree rings (Xia et al., J Biomed Opt, 17(5), 2012), open rings (<360 degrees) (Dima et al., Opt Express, 20(22), 25044-25057, 2012; van Es et al., J Biomed Opt, 19(6), 2014; Ermilov et al., J Biomed Opt, 14(2), 2009), or hemispherical geometries (Kruger et al., Med Phys, 37(11), 6096-6100, 2010). The use of a transducer ring or shell increases the viewing aperture of the detector scheme, improving image quality and reducing artifacts with fewer scan points. A PAT system resembling a traditional X-ray mammography system has been demonstrated using a plate array of transducers and transillumination of compressed breast tissue (Manohar et al., Phys Med Biol, 50(11), 2543-2557, 2005).

In addition to systems designed for imaging breast and other large organs, there are many examples of intravascular or endoscopic PAI systems. Such systems have been developed for vascular plaque detection (Wang et al., Sci Rep-Uk, 4, 2014), transvaginal ovary imaging (Salehi et al., Biomed Opt Express, 5(9), 3074-3079, 2014), and esophageal imaging (Yang et al., Plos One, 10(4), 2015). A recent study on photoacoustic prostate imaging demonstrated the use of two separate probes, a transurethral fiberoptic illuminator and a transrectal ultrasound detector (Bell et al., J Biomed Opt, 20(3), 2015).

PAM systems often resemble a benchtop microscope. Light is focused to a very small spot size, and a focused acoustic transducer is used to collect signals from a smaller region of tissue. PAM systems may be limited by either the optical resolution (small laser spot size, OR-PAM), or acoustic resolution (small acoustic focal zone, AR-PAM,). While PAM offers penetration depths of 1-10 mm (much deeper than pure optical microscopy), it also offers high spatial resolution (~1-10 µm lateral, 5-15 µm with depth). By imaging at multiple wavelengths, highly detailed maps of vasculature can be generated with spectral information related to vessel oxygenation. The disclosed phantoms can be readily constructed for PAM applications.

Additional photoacoustic detection systems and applications thereof are described below:

Two-Photon Absorption-Induced PAI. PAI performed with femtosecond pulses harnessing two-photon absorption effects (relatively rare event where two photons of equal wavelength combine into a single photon with half the wavelength (i.e., twice the energy) (see, e.g., Langer et al., Opt Express, 21(19), 22410-22422, 2013, incorporated by reference herein).

Combined PAT/Diffuse Optical Tomography (DOT). DOT provides optical property data on tissue, which may be used to improve PAT image reconstruction and tissue analysis (see, e.g., Li et al., Biomed Opt Express, 2(8), 2348-2353, 2011, incorporated by reference herein).

Multiphoton Photoacoustic/Fluorescence Spectroscopy. Multiphoton photoacoustic sensing, but in a spectroscopic system for smaller samples (such as biopsy tissue samples) (see, e.g., Chandrasekharan et al., Appl Spectrosc, 58(11), 1325-1333, 2004, incorporated by reference herein).

Frequency Domain PAI. Instead of using a rapid pulsed laser, PAT may be done using an continuous laser source with rapidly modulated intensity (see, e.g., Telenkov et al., Opt Lett, 36(23), 4560-4562, 2011, incorporated by reference herein).

Molecular Imaging: By combining light-absorbing particles (plasmonic nanoparticles, dyes) with biochemical targeting labels/moieties, optical sensing of biomolecules may be performed. Targeted biological molecules include cell receptors such as HER2, EGFR, and VEGF, as well as infectious bacterial or viral agents. Molecular imaging may be performed by many pure optical imaging modalities as well as by PAI (see, e.g., James et al., Physiol Rev, 92(2), 897-965, 2012, incorporated by reference herein).

Raman-PAI. By delivering successive pulses at different wavelengths, Raman vibrational effects can be converted into photoacoustic signals. Useful for label-free molecular sensing in tissues (see, e.g., Yakovlev et al., Opt Lett, 36(7), 1233-1235, 2011, incorporated by reference herein).

Photoacoustic Elastography. The measurement of tissue elastic/mechanical properties via photoacoustic sensing. (see, e.g., Liu and Yuan, Biomed. Opt. Exp. 7, 2016, http://dx.doi.org/10.1364/BOE.7.003323)

Ultrasound-Mediated Optical Tomography.

Another hybrid light-sound imaging technique is Ultrasound-Mediated Optical Tomography (UMOT) (Elson et al., Interface Focus, 1(4), 632-648, 2011, which is incorporated by reference herein). Instead of emitting light and detecting generated sound waves (as in PAI), light is transmitted to tissue and detected using an optical photodetector or CCD camera. An ultrasound beam is used to vibrate the tissue within the beam, which changes the position of light-scattering particles. This effect "tags" photons and will cause changes in the laser beam phase and speckle pattern received by the detector. These speckle patterns can be used to infer tissue absorption and scattering properties, enabling applications related to vascular imaging, oximetry, breast cancer, and functional imaging. Because this modality involves light and sound transport, the disclosed phantoms would be well suited to this technology.

Optical Detection Systems

Because the disclosed phantoms have realistic tunable optical properties, they are also suitable for evaluating performance of pure medical optical imaging systems.

Hyperspectral Reflectance Imaging. Hyperspectral Reflectance imaging (HRI) is a superficial imaging technique where a camera/filter system acquires superficial images of tissues at multiple filtered wavelengths, thus acquiring an optical spectrum at each pixel in the image. These spectra can then be used to determine tissue absorption and scattering properties, especially relative concentrations of oxy- and deoxy-hemoglobin, as well as exogenously delivered contrast agents (e.g. ICG) (see, e.g., Lu et al., J Biomed Opt, 19(1), 2014, and Wang et al., Proc SPIE, 9325(932508), 2015, each of which is incorporated by reference herein).

Diffuse Optical Tomography. Diffuse Optical Tomography (DOT) is a pure optical imaging modality that offers deeper imaging (~3-4 cm) but with poor resolution (~5 mm). Light is delivered from and collected at multiple points across the tissue using fiberoptics. Many systems use endogenous tissue contrast from blood, water, and lipids, but others utilize fluorescent detection of delivered contrast agents (Ntziachristos et al., PNAS, 97(6), 2767-2772, 2000). DOT has been studied extensively for breast cancer detection due to its ability to detection deep lesions with different optical properties from adjacent healthy tissue. Recently, a combined DOT/PAT has been demonstrated, where DOT data is used to improve the quality of PAT measurements of quantitative chromophore concentration and distribution (Li et al., Biomed Opt Express, 2(8), 2348-2353, 2011). Another application of DOT is in vivo functional brain imaging, often called functional near-infrared spectroscopy (fNIRS). Near-infrared light may be transmitted through the skull, enabling oximetry of the outer layers of the brain. This oximetry information can then be correlated with brain metabolic response to various stimuli, such as a motor task or visual stimuli. Exemplary features of DOT are provided, for example, in Leproux et al., (Breast Cancer Res, 15(5), 2013, which is incorporated by reference herein and describes breast cancer detection using DOT) and Li et al. (Biomed Opt Express, 2(8), 2348-2353, 2011, which is incorporated by reference herein and describes an integrated DOT/PAT system for breast imaging).

Functional Near-Infrared Spectroscopy (fNIRS). A technology similar to DOT, where different wavelengths of light are used to estimate blood oxygenation. The most common application is brain imaging, where oxygen consumption mapping may be correlated with neurological function (see, e.g., Hillman, J Biomed Opt, 12(5), 2007, incorporated by reference herein).

Spatial Frequency Domain Imaging (SFDI). A form of diffuse imaging where a slotted mask is used to only allow partial illumination of a tissue. The addition of this "spatial wave" results in depth-selective optical imaging capable of estimating chromophore distributions (see, e.g., O'Sullivan et al., J Biomed Opt, 17(7), 2012, incorporated by reference herein).

Ultrasound Detection Systems

The disclosed phantoms have biologically realistic acoustic properties and therefore can be used for testing and calibrating ultrasound imaging systems, including standard B-mode (2D) imaging, Doppler imaging, and 3D Ultrasound Tomography. Such ultrasound systems are commonly used in medical practice (see, e.g., Tsabo, *Diagnostic Ultrasound Imaging: Inside Out*, 2$^{nd}$ Edition, Academic Press, San Diego, 2014).

V. Performance Characteristics Of Detection Systems For Interrogation

The disclosed phantoms can be used to calibrate and assay numerous performance characteristics of an optical or acoustic detection system, such as a PAI system, or any system that generates photoacoustic-based data and can benefit from a phantom having biomimetic optical and acoustic properties (for example, photoacoustic imaging data, non-imaging probe data such as pump-probe lifetime-type measurement techniques for pH sensing (see, e.g., Ashkenazi, J Biomed Opt., 13(3), 034023, 2008)). Non-limiting examples of such performance characteristics are provided below:

Spatial resolution (Axial, Lateral, Elevational): the ability to distinguish two closely-spacing point-like objects from each other. Spatial resolution in imaging can be measured using many different phantom targets. A single thin wire or filament may be imaged over its cross section, producing a resolution-limited point spread function (PSF) from which axial and lateral resolution may be calculated. Alternatively, images may be acquired along the wire axis, showing a line spread function (LSF). In some embodiments, the phantom can contain dense arrays of adjacent wires, relying on visual distinction of overlapping PSFs as the measure of resolution. Targets for resolution testing should be much smaller than the resolution of the system (e.g. <100 µm for a typical PAT system).

Penetration depth: The maximum depth at which a target of known absorbing strength is detectable (distinguishable from system noise). This characteristic may be tested using an array of equally absorptive targets at several depths within the phantom. If the detection criterion is qualitative visualization by an observer, the maximum penetration depth is given by the deepest visualized target. Quantitative analysis may also be used, where metrics such as target contrast, contrast-to-noise ratio, or signal-to-noise ratio above a certain threshold may dictate sufficient detectability.

Low-contrast detectability, contrast-detail analysis: Visualization of a target depends on its intensity/brightness as well as its size and shape (e.g. a small but medium-contrast target may be more visible than a large but low-contrast target). Testing of this effect is referred to as contrast detail analysis; contrast detail analysis phantoms possess targets of varying size at different contrast levels. Low-contrast detectability, the ability to visualize weak-signal targets against background signals, is a related component of this analysis that captures the sensitivity of the system to target absorption strength (related to concentration of absorbing particles/chromophores).

Field of view: the physical dimensions of the area or volume that may be simultaneously imaged by a system. FOV tests may be performed in phantoms with any type of target, but small, high-contrast targets provide the most accurate determination of FOV.

Uniformity: PAT image intensity may vary within the field of view due to many factors, e.g. uneven illumination of the tissue, differences in tissue optical/acoustic properties, or reconstruction artifacts. To distinguish from target contrast variance with depth (see Penetration Depth and low-contrast detectability), uniformity can be defined as the image background uniformity. Uniformity may be tested in a phantom similar to penetration depth phantoms, where an expected depth dependence in background signal may be observed and quantified.

Distortion: Distortion is the spatial warping of an image resulting in deviation of perceived physical dimensions from the true physical dimensions. Distortion may result from hardware effects (e.g. optical lensing/focusing, acoustic transducer aperture effects), inadequate image reconstruction (e.g. incorrect assumed speed of sound in the phantom causes mis-registration of spatial coordinates), or spatially inhomogeneous properties of the imaged object/medium. Distortion may be quantified using an array of targets with known spacing in a regular pattern within the image (e.g. rectangular grid of sub-resolution targets or larger targets). The choice of target depends on what distortion sources are of interest: geometric distortion/mis-registration is easily captured using point targets, while other types of distortion such as reconstruction artifacts should be characterized using larger targets. A classic example is the limited aperture artifact in ultrasound/photoacoustics, where circular objects near the edge of the transducer field of view appear as lateral "spindle" shapes, even though the grid pattern of the target array may appear unaltered.

Spatial measurement accuracy: Spatial measurement accuracy is another component of spatial registration accuracy (see Distortion), referring to measurement of distances, areas, and volumes of features within the image. Distance accuracy is the simplest type of spatial measurement, and may be readily characterized using sub-resolution PSF targets placed at highly accurate positions within a phantom with biologically relevant optical and acoustic properties (IEC 61391-1 calls for placement to within +/−0.1 mm). Because tissues are heterogeneous, interfaces with mismatched acoustic properties cause reflection artifacts and spatial mis-registration. The disclosed phantoms may be used to simulate these complex tissue environments, where traditional PAT/ultrasound phantoms are acoustically uniform.

Signal-to-noise ratio (SNR): SNR is a description of the recoverability of a target signal relative to the noise/image background, but generally refers to the measured acoustic wave signal amplitude of the acoustic transducer, rather than the SNR of the imaged target based on pixel intensity. SNR may be characterized vs. depth (see penetration depth) using an array of absorptive inclusions. However, instead of computing target contrast relative to the background, target intensity is compared against an image acquired under pure electronic noise (e.g., the transducer in open air).

Linearity: Linearity describes the relationship between target signal strength and its imaged intensity. Linearity may be measured using similar phantoms to low-contrast detectability, such as an array of targets with different known signal strength. Linearity is determined by curve-fitting measured target image intensity versus target absorption strength (e.g. contrast level or absorber concentration). For a linear PAT system, a linear relationship between target intensity/contrast and absorber concentration is expected. Linearity may be affected by system hardware and software as well as by tissue effects. Linearity phantoms may be comprised of one or more channels filled with varying concentrations of an absorptive dye/material, where images are recorded for each concentration and target intensity/contrast data are compared. Linearity can also be represented as the relationship between a secondary parameter (e.g., blood oxygenation, pH)—that causes changes in a photoacoustically-detectable parameter (e.g., absorption coefficient)—and the imaged or device-detected intensity.

Dynamic Range: The range of device-determined signal intensities that can be generated based on a range of inherent target strengths—ideally from a target strength of zero to the maximum expected in biological tissue. Can also be represented as the range of device-generated signal intensities caused by changes in a secondary parameter (e.g., temperature, pH), that directly affects a photoacoustically detectable parameter (e.g., absorption coefficient).

Artifacts: Artifacts are undesirable features in an image that do not represent the structure or properties of the sample being imaged or measured. The presence of artifacts may degrade image/data quality and/or obfuscate visualized features in an image, making image/data interpretation challenging. Artifacts may be caused by incorrect acquisition and post-processing techniques, as well as by tissue/sample properties and geometry, instrumentation or physical processes which cannot easily be corrected for by data processing, or some combination of these factors. System susceptibility to artifacts may be characterized using phantoms containing inclusions designed to reproduce artifacts encountered in tissue. Artifacts may be quantified using metrics such as artifact-to-noise ratio or artifact-to-background ratio.

Spectral measurement accuracy: Photoacoustic and other optical imaging techniques may utilize multiple-wavelength illumination to perform spectroscopic measurement of tissues. The measured spectra may be thought of as a combination of the spectra of distinct chromophore species (e.g. water, lipids, blood, nanoparticles). From these spectral data, unmixing algorithms may be used to determine the relative amount of each absorber present. Phantom methods for evaluating this aspect of PAT systems should provide targets and a background medium with biologically relevant optical property spectra. For example, hemoglobin solutions contained within fluid channels will accurately simulate discrete blood vessel absorption at multiple wavelengths, while phantom background properties could be tuned to match tissue-relevant absorption and scattering spectra. Specific versions of this testing include evaluation of:

a. Tissue blood oxygen saturation (sO2) due to oxy-, deoxy-hemoglobin b. Concentration of dyshemoglobins (metHb, carboxyHb)

c. Concentration of targeted or untargeted contrast agents (plasmonic nanoparticles, absorptive or fluorescent dyes).

Biomimetic geometry: One of the advantages of the disclosed phantoms is that they can be formed into the shape of living organ or tissue, of body parts, or of whole animals (such as a small mammal, for example a mouse), and can further include selected defects, such as optical or acoustic inclusion bodies that mimic tumor tissue. Thus, the disclosed phantoms can be used to test and calibrate the performance of optical acoustic detection systems in the context of a sample with a morphologically realistic shape. Additionally, phantoms with biologically realistic geometry may be used for other uses such as user training for optical and acoustic detection/imaging systems or exhibition/demonstration of the use of such systems.

V. Additional Embodiments

Clause 1. A composition, comprising:
poly(vinyl chloride) (PVC) and a binary plasticizer comprising or consisting of benzyl butyl phthalate (BBP) and di(2-ethylhexyl) adipate (DEHA).

Clause 2. The composition of clause 1, comprising from 2% to 20% m/m PVC/binary plasticizer; and particularly comprising from 10% to 20%, from 5% to 15%, from 7% to 12%, or from 8% to 10%, m/m PVC/binary plasticizer; or particularly comprising about 5%, about 8%, about 9%, about 10%, about 11%, about 15%, or about 20%, m/m PVC/binary plasticizer.

Clause 3. The composition of clause 1 or clause 2, wherein the binary plasticizer comprises or consists of BBP and DEHA at a volume ratio of from 1000:1 to 1:1000; and particularly wherein the binary plasticizer comprises or consists of BBP and DEHA at a volume ratio of from 100:1 to 1:100;

particularly wherein the binary plasticizer comprises or consists of BBP and DEHA at a volume ratio of about 99:1, about 95:5, about 90:10, about 85:15, about 80:20, about 75:25, about 70:30, about 60:40, about 50:50, about 40:60, about 30:70, about 25:75, about 10:90, or about 1:99; or particularly wherein the binary plasticizer comprises or consists of BBP and DEHA at a volume ratio of 99:1, 95:5, 90:10, 85:15, 80:20, 75:25, 70:30, 60:40, 50:50, 40:60, 30:70, 25:75, 10:90, or 1:99.

Clause 4. The composition of any of clauses 1-3, further comprising one or more additives comprising an optical absorber, an optical scatterer, an acoustic absorber; and/or an acoustic scatterer;

particularly wherein:
the optical absorber comprises black plastic colorant (BPC);
the optical scatterer comprises titanium dioxide;
the acoustic absorber comprises glass microparticles comprising a mean diameter of from 10 to 100 μm; and/or the acoustic scatterer comprises glass microparticles comprising a mean diameter of less than 10 μM.

Clause 5. The composition of clause 4, comprising about 10% m/m PVC/binary plasticizer, binary plasticizer comprising BBP and DEHA at a volume ratio of about 30 to about 70, about 25 mg/mL silica microparticles, about 1.5 mg/mL titanium dioxide, and no BPC;

about 10% m/m PVC/binary plasticizer, binary plasticizer comprising BBP and DEHA at a volume ratio of about 75 to about 25, about 50 mg/mL silica microparticles, about 1.75 mg/mL titanium dioxide, and about 0.002% v/v BPC;

about 10% m/m PVC/binary plasticizer, binary plasticizer comprising BBP and DEHA at a volume ratio of about 90 to about 10, about 100 mg/mL silica microparticles, about 2.5 mg/mL titanium dioxide, and about 0.002% v/v BPC;

about 10% m/m PVC/binary plasticizer, binary plasticizer comprising BBP and DEHA at a volume ratio of about 99 to about 1, about 200 mg/mL silica microparticles, about 2.5 mg/mL titanium dioxide, and about 0.008% v/v BPC;

about 10% m/m PVC/binary plasticizer, binary plasticizer comprising BBP and DEHA at a volume ratio of about 40 to about 60, no silica microparticles, about 1.5 mg/mL titanium dioxide, and no BPC;

about 8% m/m PVC/binary plasticizer, binary plasticizer comprising BBP and DEHA at a volume ratio of about 90 to about 10, about 25 mg/mL silica microparticles, about 2.5 mg/mL titanium dioxide, and no BPC;

about 8% m/m PVC/binary plasticizer, binary plasticizer comprising BBP and DEHA at a volume ratio of about 75 to about 25, about 50 mg/mL silica microparticles, about 1.5 mg/mL titanium dioxide, and about 0.004% v/v BPC; or about 8% m/m PVC/binary plasticizer, binary plasticizer comprising BBP and DEHA at a volume ratio of about 75 to about 25, about 100 mg/mL silica microparticles, about 2.0 mg/mL titanium dioxide, and about 0.012% v/v BPC.

Clause 6. The composition of any of clause 5, further comprising about 1% v/v heat stabilizer/binary plasticizer.

Clause 7. A method of producing a phantom, comprising:

providing a composition according to any one of clauses 1-6; and forming the composition into the shape of the phantom.

Clause 8. The method of producing the phantom of clause 7, wherein the phantom has one or more fluid channels comprising a tubular wall formed by the PVCP gel, and wherein forming the composition into the shape of the phantom comprises:

heating the composition to a molten gel phase;

pouring the composition into a mold comprising one or more retractable wires;

allowing the composition to cool to a solid gel phase; and retracting the wires to form the one or more fluid channels in the phantom.

Clause 9. A method of using an optical and/or acoustic detection system, comprising:

providing the phantom of any of claims 1-26;

directing optical pulses of light at ultraviolet, visible, near-infrared and/or infrared wavelengths to the phantom; and/or directing acoustic waves at frequencies between 10 kHz and 20 GHz to the phantom; and detecting optical and/or acoustic signals produced at the phantom responsive to the optical pulses and/or acoustic waves.

Clause 10. The method of clause 9, wherein the detection system is a photoacoustic detection system or an ultrasound detection system.

Clause 11. The method of clause 9 or clause 10, wherein using the optical and/or acoustic detection system comprises calibrating or testing the system, or training a user on the system.

Clause 12. A method of calibrating or testing a photoacoustic imaging system, comprising:

providing the phantom of any of claims 1-26;

directing optical pulses at near-infrared and/or infrared wavelengths to the phantom;

detecting a plurality of acoustic signals produced at the phantom responsive to the optical pulses;

processing the plurality of the acoustic signals to generate a target image.

Clause 13. A method of calibrating or testing an optical acoustic detection system, comprising:

providing the phantom of any of claims 1-26;

directing optical pulses at ultraviolet, visible, near-infrared and/or infrared wavelengths to the phantom; and detecting an acoustic signal produced at the phantom responsive to the optical pulses.

Clause 14. The method of clause 13, further comprising processing the acoustic signal to generate spectroscopic data or imaging data and/or other diagnostic data.

Clause 15. A method of calibrating or testing an ultrasound imaging system, comprising:

providing the phantom of any of claims 1-26;

directing acoustic energy at ultrasonic frequencies to the phantom;

detecting a plurality of acoustic signals remitted from the phantom responsive to the delivered acoustic energy processing the plurality of the acoustic signals to generate a target image.

Clause 16. A photoacoustic imaging system, comprising:

an optical pulse source configured to direct optical pulses at near-infrared or infrared wavelengths to a target;

the target, wherein the target comprises the phantom of any of claims 1-26;

one or more acoustic transducers configured to detect acoustic signals produced in response to the optical pulses directed to the target; and a signal processor configured to receive the detected acoustic signals and produce a target image based on the detected acoustic signals.

Clause 17. An optical acoustic detection system, comprising:

an optical pulse source configured to direct optical pulses at ultraviolet, visible, near-infrared and/or infrared wavelengths to a target;

the target, wherein the target comprises the phantom of any of claims 1-26;

one or more acoustic transducers configured to detect acoustic signals produced in response to the optical pulses directed to the target; and a signal processor configured to receive the detected acoustic signals and process the acoustic signals to generate spectroscopic data or imaging data and/or other diagnostic data.

Clause 18. An ultrasound detection system, comprising:

an ultrasound source configured to direct ultrasound pulses of frequencies between 10 kHz and 20 GHz to a target;

the target, wherein the target comprises the phantom of any of claims 1-26;

one or more acoustic transducers configured to detect acoustic signals produced in response to the ultrasound pulses directed to the target; and a signal processor configured to receive the detected acoustic signals and process the acoustic signals to generate spectroscopic data or imaging data and/or other diagnostic data.

EXAMPLES

The following examples are provided to illustrate particular features of certain embodiments, but the scope of the claims should not be limited to those features exemplified.

Example 1

Biologically Relevant Photoacoustic Phantoms with Tunable Optical and Acoustic Properties Photoacoustic Tomography (PAT) is a rapidly maturing imaging modality that combines pulsed laser irradiation with ultrasonic sensing to provide optical absorption information at depths on the order of centimeters. Applications of PAT include vascular imaging, cancer detection, and mammography. Because PAT is an emerging technology, there are no currently recognized standard test methods for conducting device performance assessment, quality control, and intercomparison. Tissue-simulating phantoms provide useful test objects and are incorporated in image quality standards for mature medical imaging technologies. For PAI system evaluation, a phantom material with tunable acoustic and optical properties is needed to accurately mimic the multi-domain tissue response. The design and characterization of novel phantom materials comprised of novel polyvinyl chloride plastisol formulations with widely tunable optical and acoustic properties is provided. Optical absorption and scattering were characterized from a wavelength of 400-1100 nm, while speed of sound and acoustic attenuation were determined over a frequency range of 4-9 MHz. A formulation specifically mimicking bulk breast tissue and construct a simple image quality phantom using this material is provided. This phantom was then used to assess performance of a PAT system, including contrast vs. depth and spatial distortion. Results indicate that this material is suitable for use in phantom-based test methods for evaluating PAT systems.

Development of appropriate phantom materials for evaluating PAI systems presents a novel challenge: phantoms should accurately mimic both the acoustic and optical properties and behavior of a particular tissue of interest. Phantom properties should also be independently tunable to enable the widest diversity in simulated tissue property sets. The most critical properties to control are optical absorption coefficient, optical scattering coefficient, speed of sound, and acoustic attenuation coefficient (Table 1 provides an approximate range of literature values for these properties in various tissues (Bosschaart et al., Lasers Med Sci, 29, 453-479, 2014; Duck, F. A., [Physical Properties of Tissue] Academic Press, London, 1990; Sandell et al., J Biophotonics, 4(11-12), 773-787, 2011; Edmonds et al., Ultrasonic Imaging, 13(2), 162-185, 1991). In this study, simulating breast tissue properties was the focus given the potential of PAT for mammography applications (Kruger et al., Med Phys, 37(11), 6096-6100. 2010; Xia et al., Biomed Opt Express, 4(11), 2555-2569, 2013; Manohar et al., J Biomed Opt, 9(6), 1172-1181, 2004; Manohar et al., Phys Med Biol, 50(11), 2543-2557, 2005; Heijblom et al., Technol Cancer Res T, 10(6), 607-623, 2011; Ermilov et al., J Biomed Opt, 14(2), 2009). Breast tissue may be thought of as a heterogeneous mix of fatty and fibroglandular tissues; fatty tissue has lower speed of sound and acoustic attenuation, while fibroglandular tissue has higher speed of sound and attenuation (D'Astous et al., Ultrasound Med Biol, 12(10), 795-808, 1986). Breast tissue composition and morphology are strongly affected by many factors, including age, menopausal state, and diseases such as cancer (Katz-Hanani et al., Ultrasound Med Biol, 40(9), 2265-2271, 2014). Thus, a highly tunable phantom material is needed to simulate various breast compositions.

Many materials have been doped with optical absorbers and scatterers for use as optical phantoms, including hydrogels, polymers, epoxies, and liquid fat emulsions such as Intralipid (Pogue et al., J Biomed Opt, 11(4), 2006). However, each of these materials has significant drawbacks for photoacoustic phantoms. Polymers and elastomers tend to have dissimilar speed of sound to tissue (e.g. silicone at 1,030 m/s (Zell et al., Phys Med Biol, 52(20), N475-N484, 2007) or polydimethylsiloxane at 1300 m/s (Avigo et al., J Biomed Opt, 20(4), 046008, 2015)), while liquid fat emulsions possess low acoustic attenuation, present a limited tuning range for speed of sound (Laufer et al., Ieee J Sel Top Quant, 16(3), 600-607, 2010), and degrade over time. Hydrogels such as agarose and gelatin containing hairs, absorbing inclusions, or fluid channels are commonly used for photoacoustic phantoms (Xia et al., Biomed Opt Express, 4(11), 2555-2569, 2013; Cook et al., Biomed Opt Express, 2(11), 3193-3206, 2011; Xia et al., J Biomed Opt, 16(7), 2011; Dima et al., Opt Express, 20(22), 25044-25057, 2012; Ephrat et al., Med Phys, 37(4), 1619-1628, 2010; Xu et al., J Biomed Opt, 15(3), 2010; Su et al., J Biomed Opt, 15(2), 2010), but hydrogel material properties and overall gel mechanical strength typically destabilize quickly over a matter of days, making them ill-suited for long-term quality control or calibration phantoms. Another material that has seen considerable use in photoacoustics is poly(vinyl alcohol) (PVA) cryogel (Manohar et al., J Biomed Opt, 9(6), 1172-1181, 2004; Xia et al., J Biomed Opt, 16(7), 2011; Kharine et al., Phys Med Biol, 48(3), 357-370, 2003; Haisch et al., Anal Bioanal Chem, 397(4), 1503-1510, 2010). PVA cryogels are formed through repeated freeze-thaw cycling, where each cycle simultaneously increases gel mechanical stiffness and optical turbidity without requiring light-scattering dopants. However, dye diffusion from inclusions has been observed after 1 year (Manohar et al., J Biomed Opt, 9(6), 1172-1181, 2004), and the acoustic and optical properties are not independently tunable, which may limit the types of tissues that can be accurately simulated.

PVCP is a suspension of a PVC resin in liquid plasticizer. When heated to its fusion temperature (typically 170-190° C.), the resin and plasticizer undergo mutual dissolution, resulting in gelation and fusion. After fusion, PVCP is poured into mold cavities to cool and solidify into a variety of pre-selected shapes. PVCP has been investigated as a material for photoacoustic phantoms (Spirou et al., Phys Med Biol, 50(14), N141-N153, 2005; Bohndiek et al., Plos One, 8(9), 2013; Lashkari et al., Rev Sci Instrum, 82(9), 2011; Lu et al., Biomaterials, 31(9), 2617-2626, 2010; Tavakoli et al., J Biomed Opt, 16(5), 2011; Telenkov et al., Opt Lett, 36(23), 4560-4562, 2011), and solid PVCP inclusions within background PVCP matrix have been reported stable for at least 6 months (Bohndiek et al., Plos One, 8(9), 2013), suggesting that this material is suitable for fabricating highly robust phantoms with stable properties. The PVCP formulation used in the literature is a commercial product for making soft fishing lures (M-F Manufacturing Co., Inc., Fort Worth, Tex.). The commercial product is denoted as 'commercial PVCP' to distinguish it from the disclosed PVCP tissue-mimicking material. This product, which produces translucent phantoms, can be doped with scatterers or absorbers to adjust the optical properties of resultant PVCP gels. However, this formulation has a speed of sound of ~1400 m/s (Spirou et al., Phys Med Biol, 50(14), N141-N153, 2005), lower than that of soft tissues (see Table 1).

TABLE 1

Optical and acoustic properties of representative soft tissues. Optical properties cover a spectrum from 600-1100 nm, while acoustic properties span 1-10 MHz.

| Tissue | Speed of Sound [m/s] | Acoustic Attenuation over 1-9 MHz [dB/cm] | Optical Absorption over 600-1100 nm [1/cm] | Reduced Optical Scattering over 600-1100 nm [1/cm] |
|---|---|---|---|---|
| Breast (fatty tissue) | 1400-1450 | 0.5-15 | 0.05-0.1 | 7-15 (bulk breast data) |
| Breast (fibroglandular tissue) | 1500-1540 | 0.5-25 | 0.05-0.3 | 7-15 (bulk breast data) |
| Breast tumors, lesions | 1450-1540 | 0.1-30 | 0.05-0.5 | 7-15 (bulk breast data) |
| Brain | 1500-1560 | 0.5-10 | 0.15-0.3 | 4-24 |
| Adipose tissue | 1410-1490 | 0.4-15 | 0.01-0.1 | 10-16 |

Methods

Plastisol Base Components and Additives

Gels made using commercially available PVCP (Super Soft Plastic, M-F Manufacturing Co., Inc.) were first characterized to enable comparison between the PVCP materials disclosed herein and previously demonstrated PVCP phantoms. The addition of hardening agent (plastic hardener, M-F Manufacturing Co.) was also assayed to modify the acoustic properties of commercial PVCP gels. In order to develop new PVCP formulations, the base plastisol components must first be selected. For PVC resin, Geon 121A was selected, which is a dispersion-grade resin appropriate for making plastisols with high plasticizer content (Shah et al., J Vinyl Addit Techn, 9(3), 146-154, 2003) (Mexichem Specialty Resins, Inc. Avon Lake, Ohio). From preliminary formulation and testing, it was determined that plasticizer choice has a profound impact on both speed of sound and acoustic attenuation of PVCP gels. Acoustic characterization of 13 liquid plasticizers was performed (Table 2) using methods described in the acoustic characteristic section below, in order to identify those plasticizers expected to produce tissue-relevant PVCP gels. From these 13 plasticizers, 4 were selected for fabricating and characterizing PVCP gels: DEGB, DPGB, BBP, and DEHA. For each plasticizer, PVCP gels were fabricated using PVC resin content from 10-20% m/m. Gels were also prepared using binary mixtures of either DEGB/DPGB or BBP/DEHA, varying composition from 0-100% v/v of each plasticizer. All gels comprised of binary plasticizer mixtures contained 10% m/m PVC. Gel acoustic properties were characterized and compared with measured acoustic properties of commercial PVCP gels.

Previous studies by others have demonstrated that optical scattering can be induced by $TiO_2$ in PVCP, while optical absorption can be increased by a black plastic colorant (BPC) consisting of carbon black dissolved in plasticizer (Black Plastic Colorant, M-F Manufacturing Co.) (Spirou et al., Phys Med Biol, 50(14), N141-N153, 2005; Bohndiek et al., Plos One, 8(9), 2013). In this study these additives were also utilized. Optical scattering affects the penetration depth of PAT, while optical absorption can be used to increase background optical attenuation or to fabricate absorptive inclusions within the phantom. Acoustic attenuation is a combination of acoustic absorption and scattering losses. The gel structure typically imparts some base acoustic absorption and scattering, while scattering may be further increased by adding microparticles such as silica (Cook et al., Biomed Opt Express, 2(11), 3193-3206, 2011; Culjat et al., Ultrasound Med Biol, 36(6), 861-873, 2010). Acoustic scattering was imparted by adding soda lime glass microspheres (diameter=38-60 μm, Spheriglass A, Potter Industries LLC, Malvern, Pa.). Each additive was separately characterized in PVCP gels containing various concentrations of either 0-1% v/v BPC, 0-2 mg/mL $TiO_2$, or 0-200 mg/mL glass microspheres. All gels used for additive characterization were fabricated using a base PVCP mixture of 75%/25% v/v BBP/DEHA, 10% m/m PVC. Gel properties were characterized using methods described in the acoustic and optical characterization sections below, while acoustic backscatter of gels containing glass microspheres was estimated using ultrasound imaging against a reference breast phantom (see acoustic backscatter section below).

Phantom Fabrication

For each batch of phantoms, a stock PVCP solution was prepared by mixing either a plasticizer or binary mixture of plasticizers with 1% v/v calcium-zinc heat stabilizer (M-F Manufacturing Co.). PVC resin was then added and dissolved using magnetic stirring for 30 min, after which the solution was degassed for 60 min. At this point the desired set of additives may be introduced to the stock solution. After mixing the PVC solution, $TiO_2$ was added to a 40 mL volume of stock solution, which was sonicated at 40° C. for 20 min. This volume was then reintroduced to the stock solution and stirred for 5 min. At this point, BPC and/or glass microspheres may be added and stirred in for 5 min. PVCP formulations were heated following the method described by Bohndiek et al. (Bohndiek et al., Plos One, 8(9), 2013). Briefly, PVCP was poured into a 100 mL round bottom flask in a magnetically-stirred oil bath maintained at 190° C. by a thermocouple. The flask, which contains a stir bar, was then evacuated and stirred at ~300 rpm. Depending on composition, after about 3-5 minutes, the PVCP undergoes a transition into a highly viscous state as gelation begins; during this time the stir rate is reduced to ~75 rpm. After an additional 4-6 minutes, the PVCP approaches full fusion, reducing viscosity and allowing stirring at initial speeds. At 12-15 minutes total heating time, the PVCP is poured into lubricated aluminum molds and cast into 5-mm thick, 38 mm diameter disks. All subsequent characterization experiments use PVCP phantoms in this shape, but with varied composition.

Acoustic Characterization

PVCP phantom acoustic properties were characterized using a broadband through-transmission technique (Wear et al., J Acoust Soc Am, 128(4), 2191-2203, 2010; Wear et al., Ultrasound Med Biol, 26(4), 641-646, 2000). Briefly, PVCP disks of various composition were placed in a water bath at the shared focus of a pair of co-axially aligned broadband transducers (V320, Panametrics, Waltham, Mass.), with one transducer acting as an emitter and the other as a detector. Both transducers have 7.5 MHz center frequencies, 1.27 cm diameters, and 3.81 cm focal lengths. Transducers were connected to a pulser/receiver (Model 5800PR, Panametrics), and received US signals were digitized (8 bit, 50 MHz) using a 400 MHz oscilloscope (9310C, Teledyne LeCroy, Chestnut Ridge, N.Y.). Speed of sound in liquid plasticizers was also measured using this technique by replacing the solid sample with a liquid sample housing with thin plastic membranes. Because the membranes were thick enough to cause attenuation at higher acoustic frequencies, liquids were measured using a pair of lower-frequency transducers with 1 MHz center frequencies, 1.91 cm diameters and 3.81 cm focal lengths (V314, Panametrics). Speed of sound in the sample, $c_s$, was calculated as (Wear et al., Ultrasound Med Biol, 26(4), 641-646, 2000)

$$c_s = \frac{c_w}{1 + \frac{\Delta t}{\Delta x} c_w}$$

where $c_w$ is the speed of sound in water, $\Delta t$ is the pulse delay between sample measurement and a water-only path reference measurement, and $\Delta x$ is the sample thickness. The acoustic attenuation coefficient vs. frequency, (f), was calculated over 4-9 MHz as (Wear et al., J Acoust Soc Am, 128(4), 2191-2203, 2010)

$$\alpha(f) = \frac{10}{\Delta x} \log\left(\frac{P_w(f)}{P_s(f)}\right)$$

where $P_w(f)$ is the acoustic power spectrum measured through a water path, and $P_s(f)$ is the power spectrum measured through the sample. Attenuation coefficient spectra were fitted to the power-law relationship $\alpha(f)=af^n$, where $\alpha$ and n are fitting parameters.

Acoustic Backscatter Estimation

Since many PAT systems also provide ultrasound imaging, PVCP phantoms should provide tissue-relevant ultrasound images. Acoustic backscattering is the major source of contrast in ultrasound images; to characterize the effect of glass microspheres on acoustic backscattering and phantom ultrasound visualization, PVCP gels containing 0-200 mg/mL glass microspheres were placed over a commercial, breast-equivalent ultrasound phantom (Model 059, CIRS, Inc., Norfolk, Va.) and imaged using the ultrasound mode in the PAT system. This commercial phantom served as an approximate reference material for breast tissue echogenicity. A region of interest (ROI) was drawn over each PVCP gel, and pixel intensity was averaged and compared with that in the same ROI in the commercial breast phantom without an overlying PVCP sample.

Optical Characterization

PVCP optical properties were characterized using spectrophotometry. PVCP disks were placed between 1-mm thick, 75 mm×50 mm glass slides (refractive index=1.51) and diffuse transmittance and reflectance measurements were made over 400-1100 nm using an integrating sphere spectrophotometer (Lambda 1050, PerkinElmer, Waltham, Mass.). NIST-traceable Spectralon standards were used to normalize measurements. Optical measurements were made on phantoms composed of 75/25% v/v BBP/DEHA, 10% m/m PVC and containing 0-1% v/v BPC, 0-4 mg/mL $TiO_2$, or 0-200 mg/mL glass microspheres. Optical absorption coefficient ($\mu_a$) and reduced scattering coefficient ($\mu_s'$) spectra were calculated using the inverse adding-doubling (IAD) method (Prahl et al., Appl Optics, 32(4), 559-568, 1993), which requires knowledge of the anisotropy factor and refractive index of the sample. The refractive indices of BBP and DEHA are 1.540 and 1.447, respectively; using the Lorentz-Lorenz mixture rule for refractive index (Helle et al., J Phys Chem-Us, 69(4), 1123, 1965), 75/25% BBP/DEHA PVCP is expected to have a refractive index of 1.516. Scattering anisotropy factor was assumed to equal 0.7 based on Mie scattering theory of $TiO_2$ in a medium with index 1.516. Phantoms with glass microspheres only present very low to mild scattering over the concentrations studied, causing poor signal-to-noise ratio in spectrophotometry data. To improve IAD output accuracy, glass microsphere phantoms also contained a fixed concentration of 1.5 mg/mL $TiO_2$ to increase phantom turbidity.

Temporal Stability

Mechanical durability and stability over time are important aspects of image quality phantoms. To evaluate temporal stability, PVCP phantoms (N=8) with similar geometry as above were made using 90/10% v/v BBP/DEHA, 10% m/m PVC, 1% v/v heat stabilizer, 1.4 mg/mL $TiO_2$, and 100 mg/mL silica particles (median diameter 10.5 μm, MIN-U-SIL 40, U.S. Silica, Frederick, Md.). Percent mass loss, optical properties, and acoustic properties were measured over 12 weeks. Initial phantom fabrication and mass measurements occurred 72 hours prior to the first measurement timepoint. Phantoms were stored in a dry steel container at normal temperature and pressure.

Phantom Imaging

To evaluate the use of PVCP phantoms for assessing PAT system performance, a PAT system was developed (FIG. 1A) comprised of a cart-based tunable near infrared (NIR) pulsed laser/optical parametric oscillator (OPO) (Phocus Mobile, Opotek, Inc., Carlsbad, Calif.) and a research-grade ultrasound system (Vantage 128, Verasonics, Kirkland, Wash.) which provides a Matlab interface for instrument control. The OPO provides 5 ns laser pulses at repetition rates up to 10 Hz, over wavelengths from 690-950 nm, and at energies up to 120 mJ. Acoustic sensing is performed using a 128-channel ultrasound transducer array with a 7.5 MHz center frequency, 7.0 MHz bandwidth, and 38.1 mm length (L11-4v, Verasonics). The OPO sends a trigger signal to the ultrasound system to synchronize data acquisition per laser pulse. An engineered diffuser (ED1-L4100-MD, Thorlabs, Newton, N.J.) is used to produce a 5 mm×40 mm elliptical beam spot to ensure uniform illumination in the image plane. The optics assembly and transducer are affixed to a 3-axis motorized stage for position control. Aluminum foil with a layer of acoustic coupling gel was fitted against the transducer surface to reduce reverb artifacts due to high surface fluence and absorption near the transducer. Image reconstruction is performed using a proprietary pixel-based reconstruction algorithm, and each frame is corrected for pulse-pulse energy variation using recordings from the OPO's internal energy meter.

Simple image quality phantoms were constructed by pouring PVCP into a mold containing an array of 0.5 mm diameter steel wires spaced by 2.5 mm vertically and horizontally (FIG. 1B). These phantoms were much larger than disk phantoms (7×7×6 $cm^3$); therefore the production method was scaled up using a 250 mL flask and stronger stir bars. PVCP was poured in 5 sequential layers until the mold cavity was filled. After the PVCP cured, wires were extracted, leaving wall-less fluid channels that were injected with Multi-4 a well-controlled commercial oxyhemoglobin solution (Instrumentation Laboratory, Bedford, Mass.). To compare the disclosed PVCP material with commercially available PVCP, two phantoms were constructed: 1) a novel PVCP phantom comprised of 75/25% v/v BBP/DEHA, 10% m/m PVC, 1.7 $TiO_2$, 50 mg/mL glass microspheres, and 2) a commercial PVCP phantom containing 0.9 mg/mL $TiO_2$ and 0.002% v/v BPC. These phantoms were designed to have the same optical properties, but different acoustic attenuation. This difference in acoustic attenuation is expected to affect penetration/visualization depth in the fluid channel array. Phantoms were imaged at 800 nm and radiant exposure of 20 mJ/cm$^2$. Photoacoustic images were acquired at 8 spatial locations, averaging over 30 frames per location. Image data was normalized, log compressed, and displayed with 8-bit intensity mapping. Regions of Interest (ROIs) were selected around visually detectable targets for subsequent analysis. Because channels will appear as two spatially resolvable targets due to photoacoustic boundary buildup (Bauer et al., J Biomed Opt, 16(9), 2011), target contrast was calculated as the difference between the mean ROI intensity after masking by half the maximum ROI intensity (essentially, a 2D spatial mask of full-width half maximum) and the mean local background intensity. To compare phantom performance results with real tissue conditions, imaging was also performed in a stack of sliced chicken breast tissue (each slice was ~5-10 mm thick). A PTFE tube containing Multi-4 was placed between each slice in an array pattern similar to that in phantoms. Image reconstruction in chicken experiments assumed a speed of sound of 1540 m/s.

Image distortion is a common concern in acoustically heterogeneous tissues such as the breast. One mechanism of distortion is incorrect spatial registration due to mismatch between the speed of sound in the imaged tissue (which may also vary spatially within the image plane) and the assumed speed of sound value used in image reconstruction. To mimic this distortion effect, a second phantom was constructed using commercial PVCP, 1.5 mg/mL TiO$_2$, containing a 1 mm diameter channel at a depth of 2 cm. This phantom has a speed of sound of 1400±2 m/s and was imaged with similar laser settings as above, but varying the speed of sound value assumed in image reconstruction from 1300 to 1600 m/s. Modifying this assumed value is a simple technique for evaluating image distortion, even if the target phantom is acoustically homogeneous. Target channel diameters were estimated from the axial distance between the maximum-intensity pixels of the top and bottom wall signals.

Results

Commercial PVCP Properties

Figure 2A:
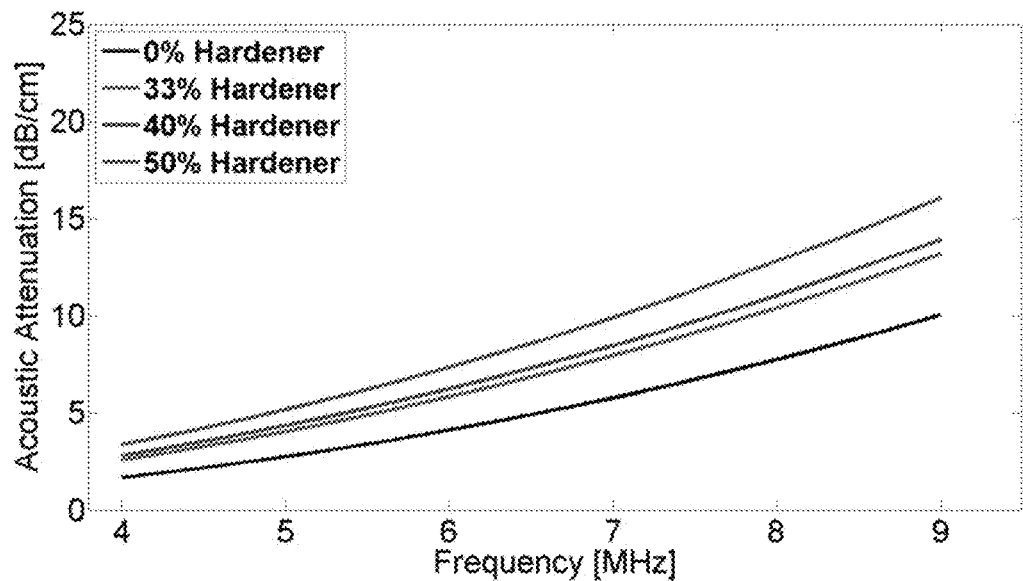
FIGS. 2A and 2B are a set of graphs showing acoustic attenuation (FIG. 2A) and the speed of sound (FIG. 2B) in a commercially purchased PVCP composition formed into a gel with varying percentages of hardener. Error bars for attenuation data omitted for clarity, with 95% confidence intervals no more than ±13.0%
Figure 2B:
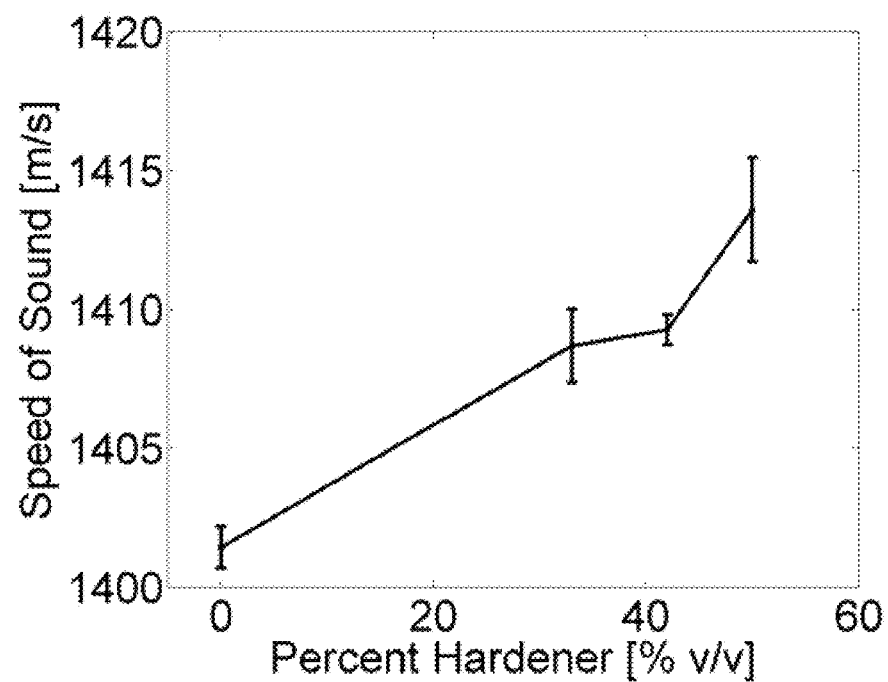

FIG. 2 shows the acoustic properties of commercial PVCP with added hardener. Hardener was found to significantly increase acoustic attenuation, but only produced small increases in speed of sound. Additional hardener was also found to increase plastisol viscosity, making fabrication and uniform mixing more difficult. From these data, it was concluded that commercial PVCP, even with commercially available additives, does not possess adequately tunable acoustic properties for tissue phantoms.

Liquid Plasticizer Properties

Table 2 shows measured speed of sound in 13 liquid plasticizers, as well as supplier-provided molecular weight and density data. The range of values was 1354-1540 m/s, which overlaps with the range of values in soft tissues, particularly fatty tissues. a positive correlation was also observed between speed of sound and plasticizer density, whereas no correlation was found with molecular weight. Of the four plasticizers selected for further characterization, three possess high speed of sound values, while DEHA provides a much lower speed of sound. It is worth noting that DEHA is the primary known plasticizer in the proprietary commercial PVCP used in this and other studies (Spirou et al., Phys Med Biol, 50(14), N141-N153, 2005; Bohndiek et al., Plos One, 8(9), 2013; Hungr et al., Med Phys, 39(4), 2031-2041, 2012).

TABLE 2

Measured sound speeds of various plasticizers. Bolded text denote plasticizers further characterized in this example. Sound speed precision <±1 m/s with 95% confidence. Molecular weight and density values provided by the supplier (Sigma-Aldrich, St Louis, MO).

| Plasticizer | Speed of Sound [m/s] | Molecular Weight [g/mol] | Density [g/mL] |
|---|---|---|---|
| Diethylene glycol dibenzoate | 1540 | 314.33 | 1.175 |
| Benzyl butyl phthalate | 1511 | 312.36 | 1.100 |
| Dipropylene glycol dibenzoate | 1480 | 342.39 | 1.120 |
| Dimethyl phthalate | 1469 | 194.18 | 1.190 |
| Diethyl phthalate | 1426 | 222.24 | 1.120 |
| Diisononyl phthalate | 1421 | 418.61 | 0.972 |
| Bis[2-(2-butoxyethoxy)ethyl] adipate | 1420 | 434.56 | 1.010 |
| Dibutyl phthalate | 1413 | 278.34 | 1.043 |
| Trioctyl trimellitate | 1413 | 546.78 | 0.990 |
| Dimethyl adipate | 1402 | 174.19 | 1.062 |
| Diisobutyl phthalate | 1386 | 278.34 | 1.039 |
| Di(2-ethylhexyl) adipate | 1381 | 370.57 | 0.925 |
| Dibutyl adipate | 1354 | 258.35 | 0.962 |

Acoustic Properties of PVCP Gels

Figure 3A:
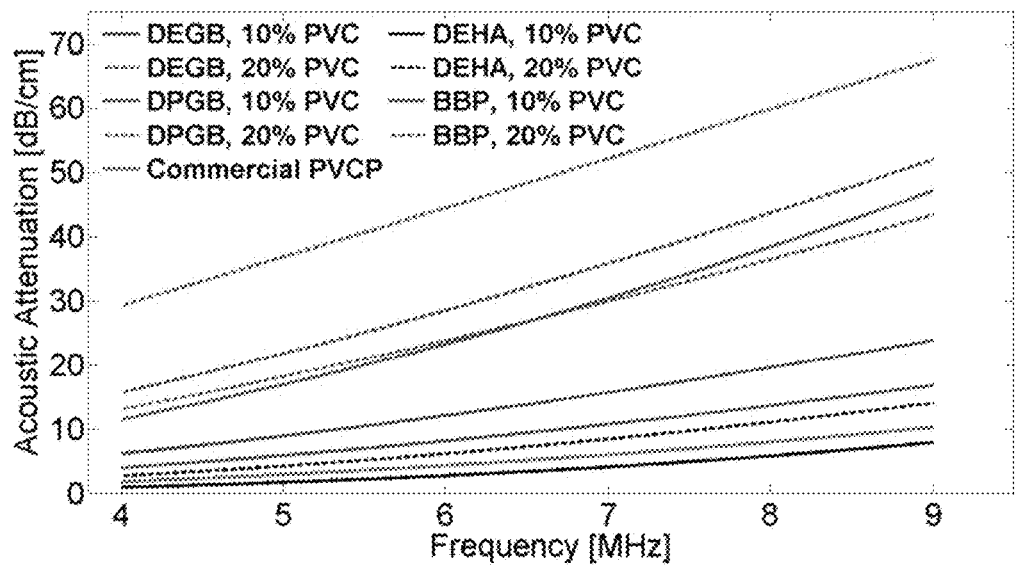
FIGS. 3A and 3B are a set of graphs showing acoustic attenuation (FIG. 3A) and the speed of sound (FIG. 3B) in PVCP gels formed with varying PVC concentrations and varying plasticizer. Comparison is provided to a commercially purchased PVCP gel. For FIG. 3A, attenuation data is shown for 10% and 20% PVC for clarity, and error bars are omitted for clarity, with 95% confidence intervals no more than ±20.2%. For FIG. 3B, error bars for speed of sound denote 95% confidence intervals.
Figure 3B:
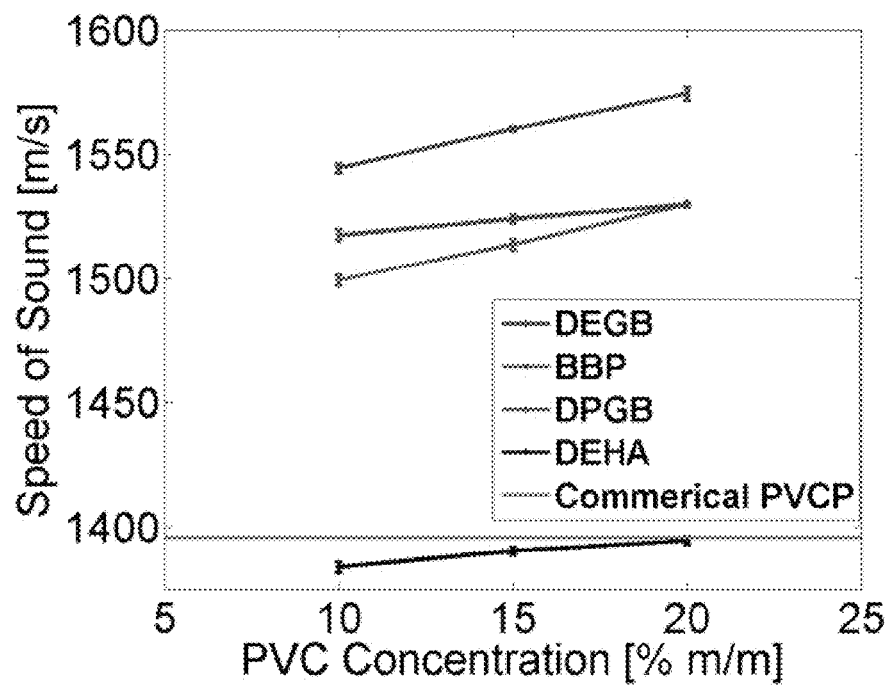
Figure 4A:
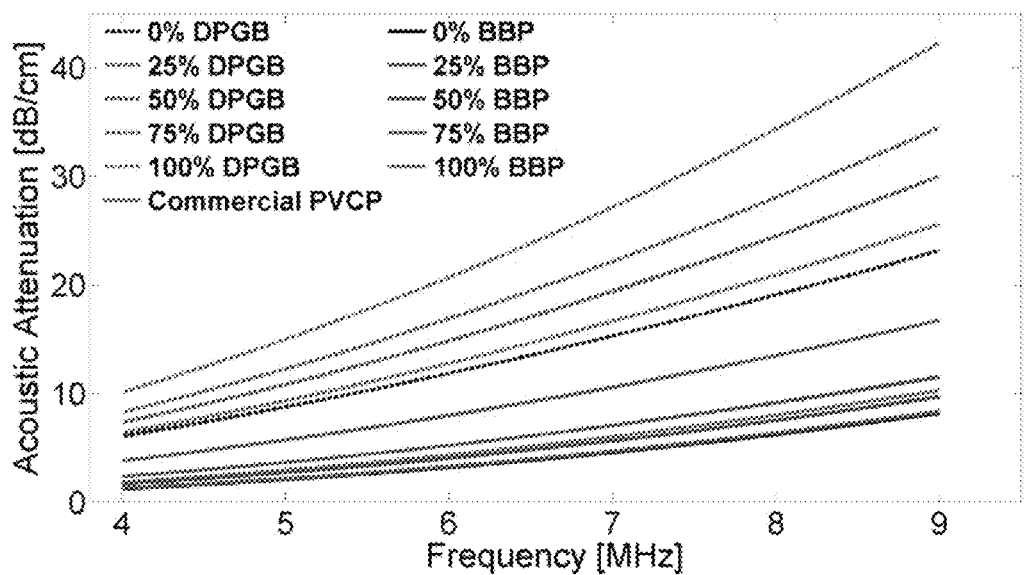
FIGS. 4A and 4B are a set of graphs showing acoustic attenuation (FIG. 4A) and the speed of sound (FIG. 4B) for PVCP gels formed using binary plasticizer comprising dipropylene glycol dibenzoate (DPGB) and diethylene glycol dibenzoate (DEGB), or BBP and DEHA. Error bars for attenuation data are omitted for clarity, with 95% confidence intervals no more than ±18.8%. Error bars for speed of sound denote 95% confidence intervals.
Figure 4B:
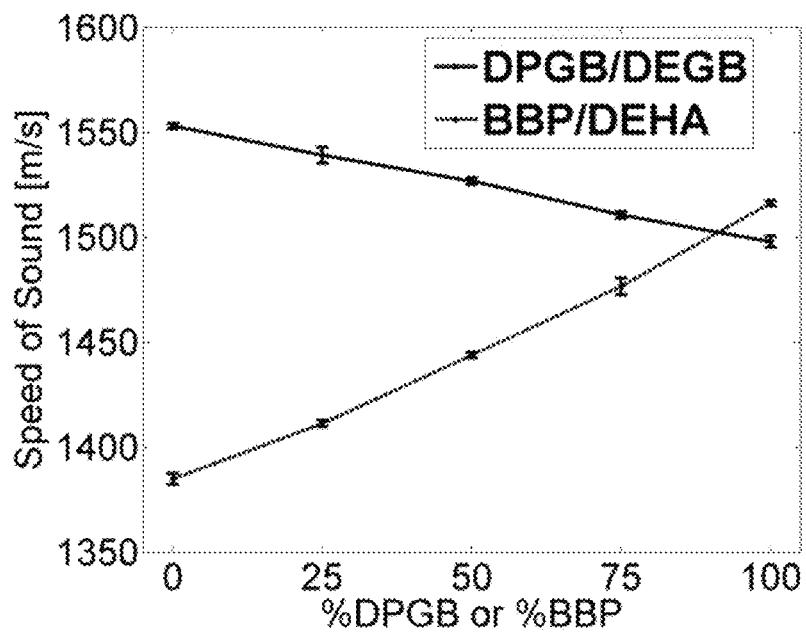

The effect of PVC concentration on acoustic properties of single-plasticizer PVCP gels is shown in FIG. 3. Increased PVC concentration causes small increases in speed of sound, but substantial increases in acoustic attenuation. Choice of plasticizer also strongly influences gel properties, with gel speed of sound closely following speed of sound values measured in liquid plasticizers. The speed of sound values for PVCP gels are generally higher than the speed of sound of the liquid plasticizers; this increase may be due to a combination of PVC having a higher speed of sound and increased fusion and strengthening of the gel matrix. Differences in acoustic attenuation between gels may be due to polymer-plasticizer solubility or affinity during the gelation and fusion processes. As shown in FIG. 4, measurements in PVCP gels containing binary mixtures of plasticizers indicate that speed of sound may be tuned following a linear rule of mixtures, while acoustic attenuation follows a nonlinear trend. It is evident that DEGB and DPGB plasticizers produce PVCP with high speed of sound, but also very high attenuation, while BBP/DEHA mixtures produce a broad tunable range for speed of sound with lower, more tissue-relevant attenuation. The speed of sound of the liquid heat stabilizer was found to be 1375 m/s; this value is similar to that of DEHA, and the low concentration (1% v/v) suggests a minimal impact on bulk properties.

Figure 5A:
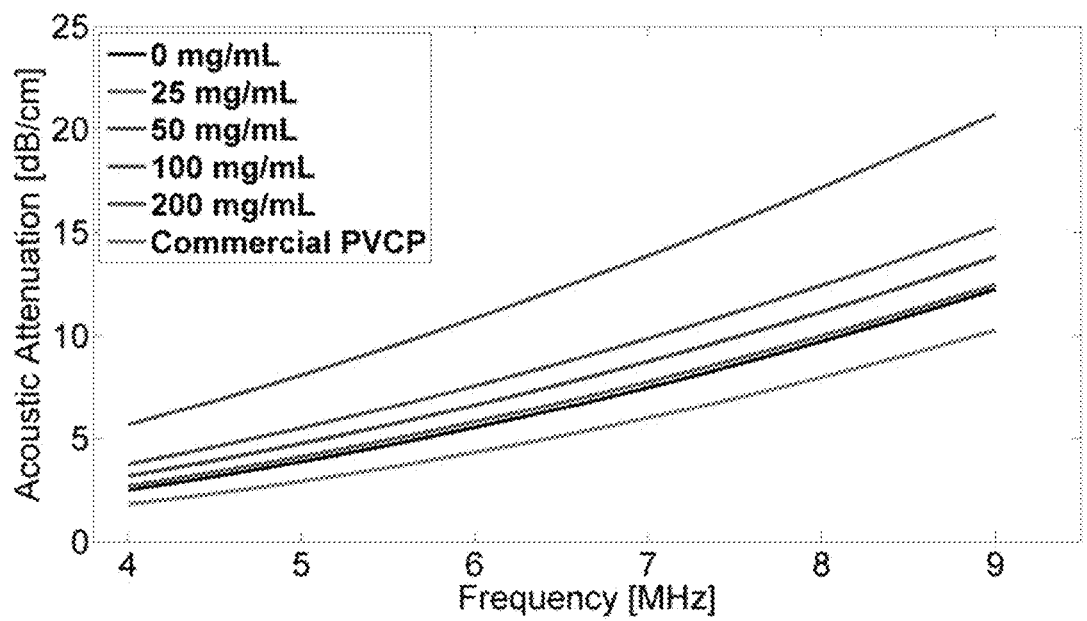
FIGS. 5A and 5B are a set of graphs showing acoustic attenuation (FIG. 5A) and the speed of sound (FIG. 5B) for PVCP gels formed using 10% m/m PVC and binary plasticizer comprising 75/25% v/v BBP/DEHA and varying concentrations of glass microparticles. Error bars for attenuation data are omitted for clarity, with 95% confidence intervals no more than ±18.8%. Error bars for speed of sound denote 95% confidence intervals.
Figure 5B:
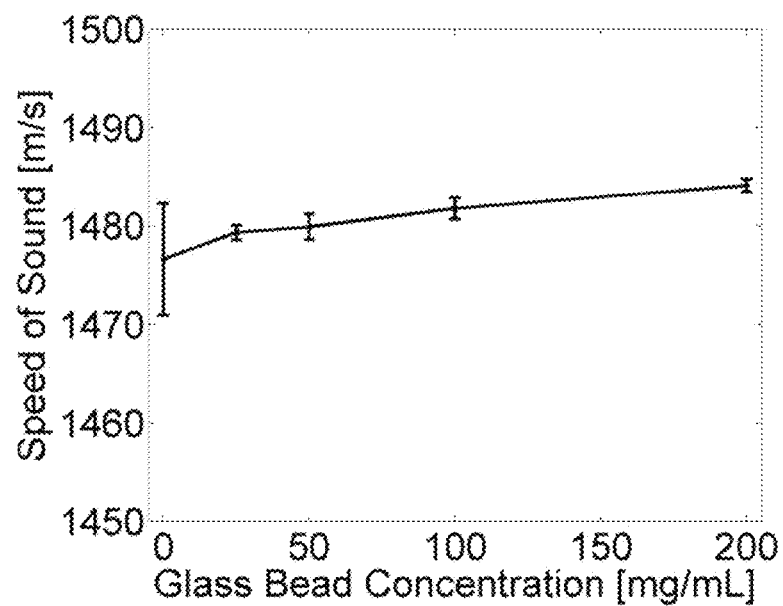

Glass beads were shown to significantly increase acoustic attenuation (FIG. 5). Phantom attenuation exhibits an approximately linear frequency dependence due to the combined effect of acoustic absorption and scattering. At higher concentrations a slight increase in speed of sound is seen, owing to the higher volume fraction occupied by the glass (~7% at 200 mg/mL). Optical additives (BPC, TiO$_2$) did not significantly affect acoustic properties, which is expected given the low concentrations and small particle sizes of carbon black and TiO$_2$. Backscatter estimation results are shown in FIG. 6. Images shown in FIGS. 6A and 6B were acquired using the same gain settings. Ultrasound images of PVCP disks show bright horizontal bands at the contact surface due to specular reflection at the boundary. Mean ROI intensity depended linearly on glass bead concentration (up to at least 100 m1g/mL), with a concentration of 50 mg/mL producing roughly equivalent intensity as the reference phantom. This suggests that PVCP phantoms can be tuned to adequately approximate acoustic backscatter in soft tissues such as the breast.

Figure 7A:
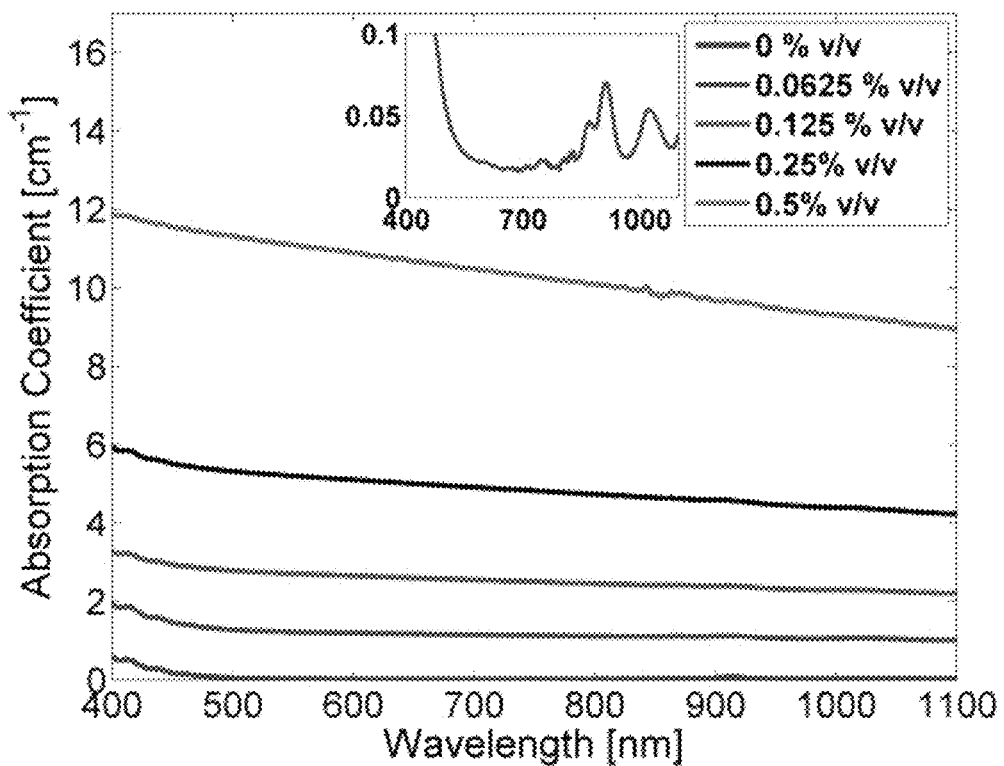
FIG. 7A is a graph showing the optical absorption coefficient for PVCP gels formed using 10% m/m PVC and binary plasticizer comprising 75/25% v/v BBP/DEHA, and varying concentrations of black plastic color (BPC) additive. The inset shows the 0% v/v spectrum, with axes in similar units.
Figure 7B:
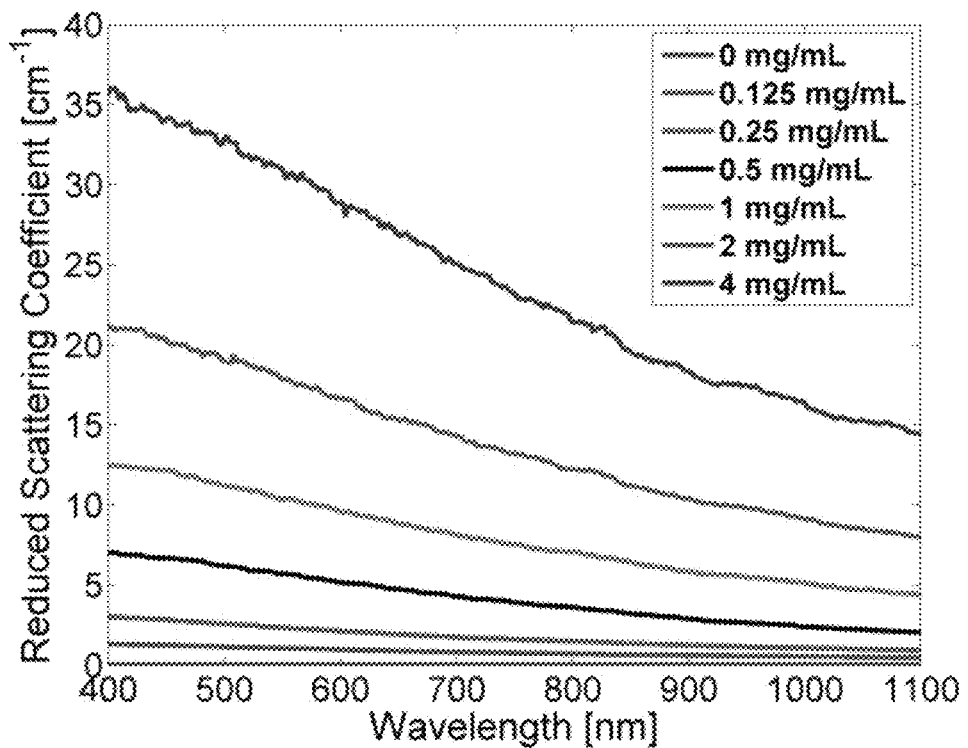
FIG. 7B is a graph showing the reduced scattering coefficient for PVCP gels formed using 10% m/m PVC and binary plasticizer comprising 75/25% v/v BBP/DEHA and varying concentrations of titanium dioxide ($TiO_2$) additive.
Figure 8A:
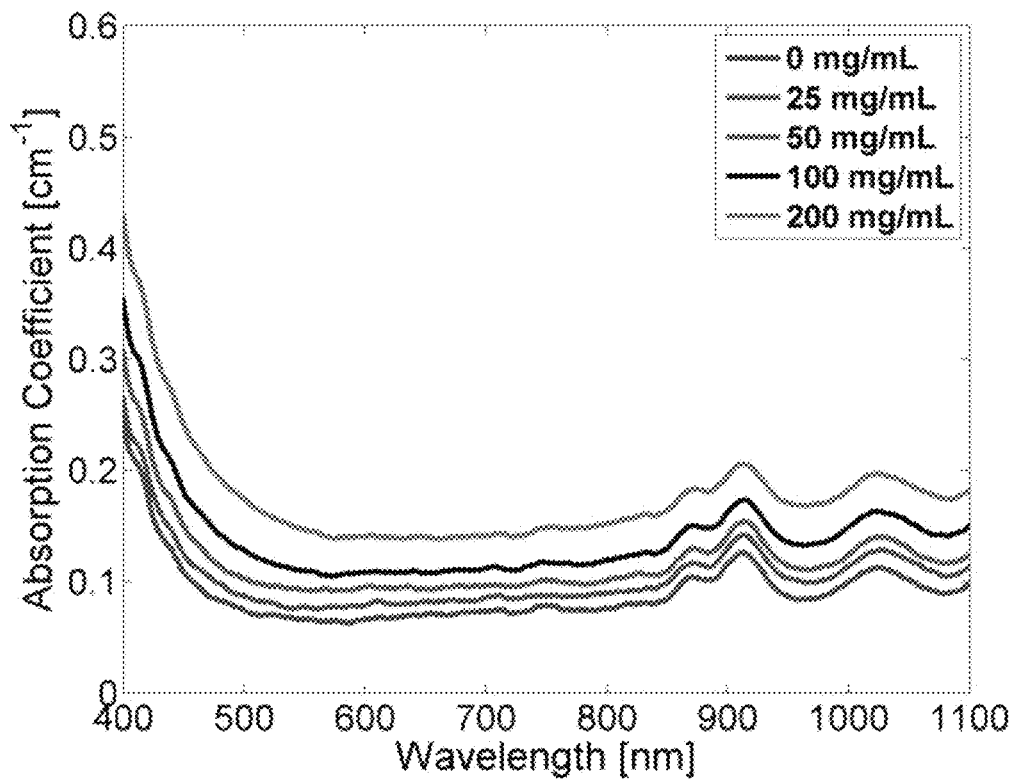
FIGS. 8A and 8B are a set of graphs showing the (FIG. 8A) optical absorption and (FIG. 8B) reduced optical scattering coefficients for PVCP gels formed using 10% m/m PVC and binary plasticizer comprising 75/25% v/v BBP/DEHA and varying concentrations of glass microparticles.
Figure 8B:
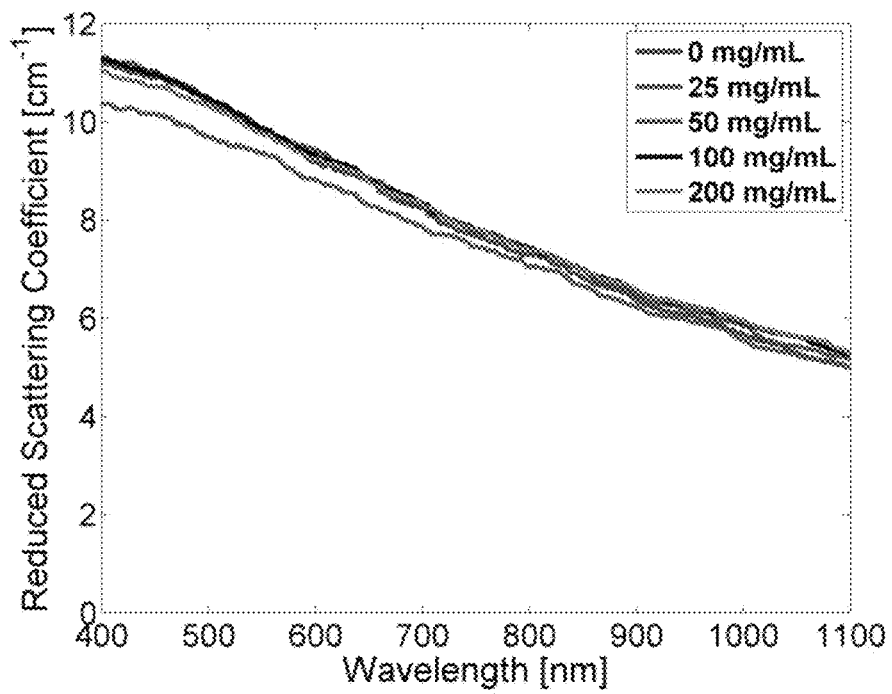
Figure 9A:
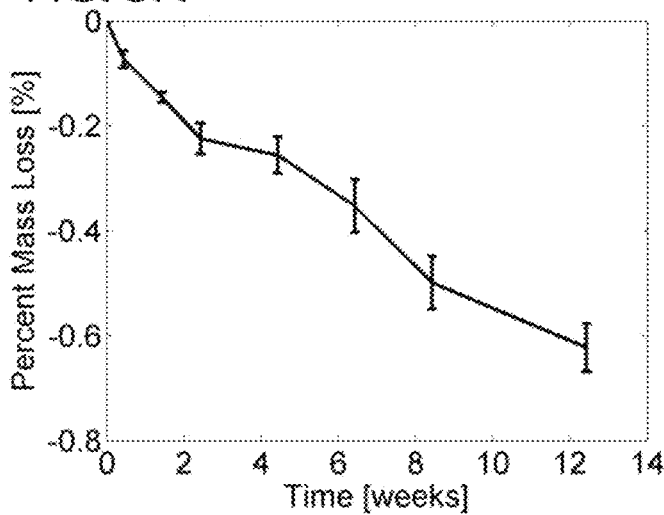
FIGS. 9A-9E are a set of graphs showing optical and acoustic properties of PVCP gels formed using 10% m/m PVC and binary plasticizer comprising 75/25% v/v BBP/DEHA over a period of 12 weeks.
Figure 9B:
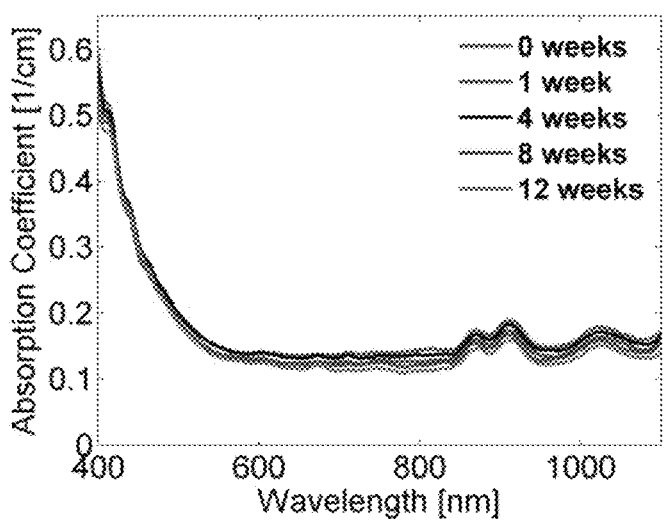
Figure 9C:
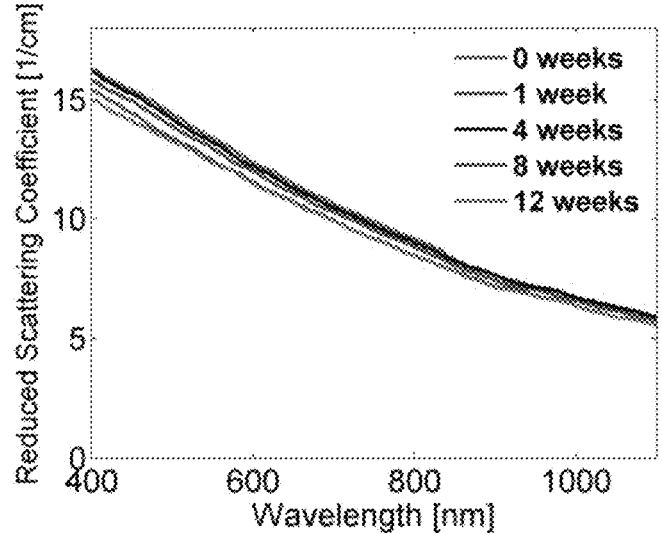
Figure 9D:
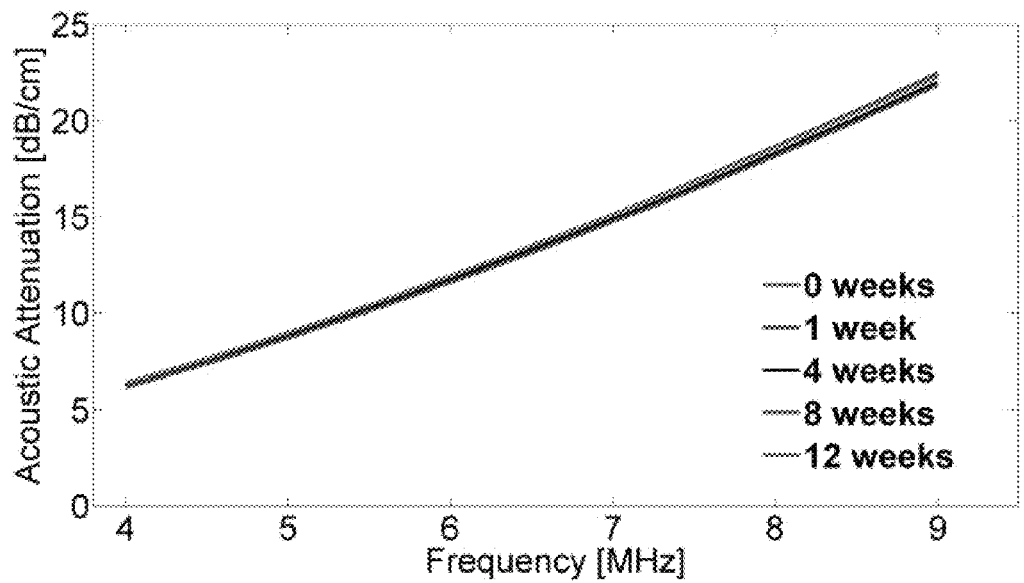
Figure 9E:
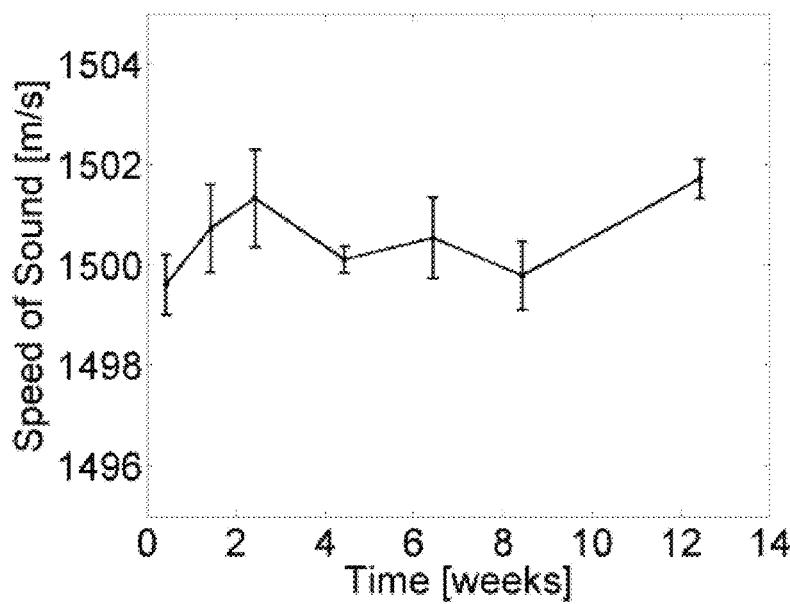

Calculated optical properties in 75/25% v/v BBP/DEHA, 10% m/m PVCP gels are shown in FIGS. 7 and 8. BPC is capable of producing relatively flat absorption spectra with values similar to that of blood. Property values strongly overlap with the reported ranges for soft tissues (Table 1). The base PVCP absorption spectrum at 0% BPC shows peaks in the NIR regime, which are characteristics of the plasticizers. As BPC content increases, these spectral peaks are removed due to dominant BPC absorption. $TiO_2$ was found to produce high optical scattering, with decreasing scattering for longer wavelengths. Glass microspheres did not significantly affect scattering relative to added $TiO_2$, but absorption was found to increase with glass microsphere concentration. However, at glass concentrations producing breast-relevant acoustic scattering (e.g., 50 mg/mL), the absorption coefficient is still breast-relevant at 0.1 $cm^{-1}$.

Stability results for BBP/DEHA phantoms are presented in FIG. 9. Small mass losses occur over time, but no monotonic trends are observed in measured acoustic properties. Mean optical absorption and reduced scattering coefficients appear to decrease at 8 weeks, but this trend was not found to be statistically significant. This variation between timepoints is likely due in part to experimental precision, rather than solely transient material changes. PVCP gels will be slightly deformed when measured with calipers or lightly held between glass slides, changing sample thickness from its nominal value. Varying the IAD sample thickness value input ±0.2 mm (±4%) caused estimated absorption and scattering outputs to vary by up to ±8%, while mean optical properties changed by up to 10% over 12 weeks. The combination of precision error and statistical error suggests that phantom optical properties are stable over 12 weeks.

The probable mass loss mechanism is volatile losses, i.e. a combination of surface evaporation and plasticizer exudation/porous diffusion. Phantoms were stored in air at normal temperature and pressure as a conservative estimate of phantom shelf life under typical usage conditions. In a more robustly fabricated image quality phantom, the phantom could be encased in a solid chamber and sealed with a thin plastic membrane to prevent environmental exposure and increase shelf life. Also, the relatively small size of these phantoms results in a higher surface-area-to-volume ratio, which may increase volatile losses compared to a larger phantom. It was observed that storage at lower temperatures can reduce plasticizer exudation, but storage below 0° C. can cause permanent damage. It was also qualitatively observed that temporal stability may increase with PVC resin concentration, but this could be undesirable depending on acoustic property requirements.

Figures 10A, 10B, 10C:
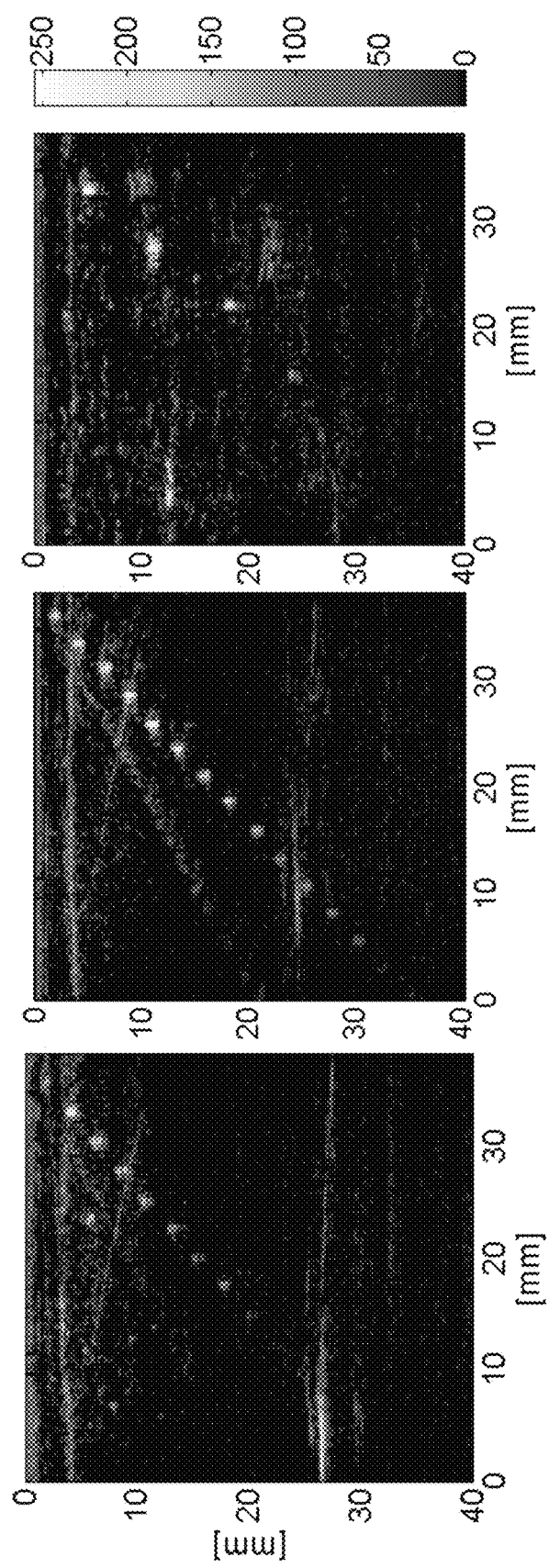
FIGS. 10A-10E show graphs and photoacoustic images illustrating the photoacoustic properties of PVCP gels, and tissue. Photoacoustic images are shown for (FIG. 10A) PVCP phantom formed using PVCP gel comprising 10% m/m PVC and binary plasticizer comprising 75/25% v/v BBP/DEHA, (FIG. 10B) PVCP phantom formed using commercial PVCP, and (FIG. 10C) chicken breast.
Figure 10D:
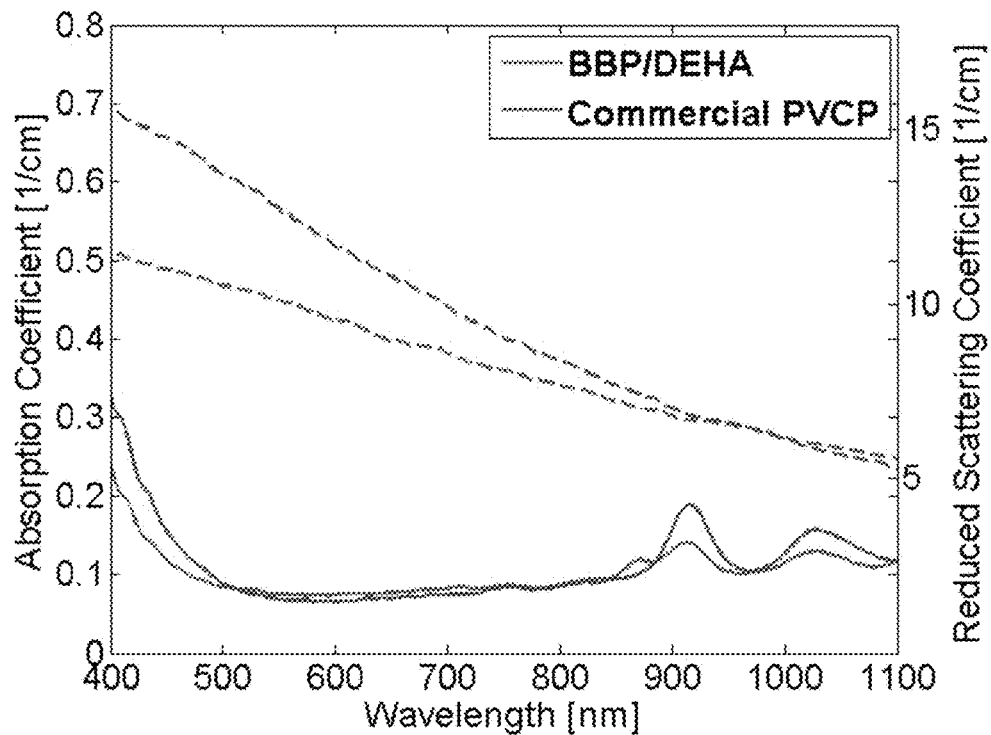
Figure 10E:
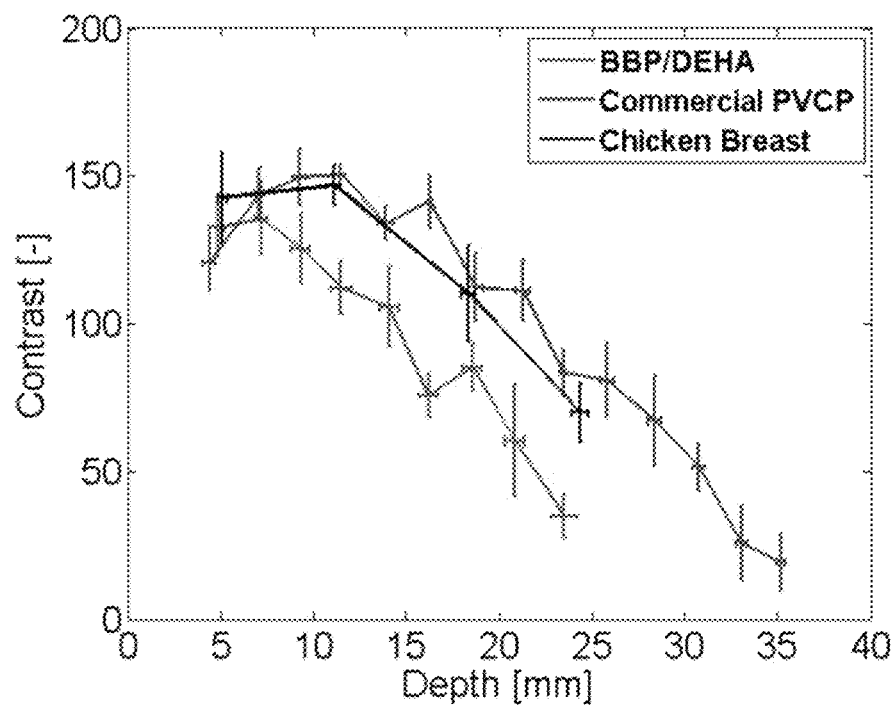

Phantom images generally high background before background subtraction as well as substantial near-field clutter due to both high surface fluence and the presence of aluminum foil over the transducer. Additionally, shallow targets produce reconstruction artifacts that appear as streaks extending laterally into deeper phantom regions. As shown in FIG. 10, measured penetration depth is significantly lower in the disclosed breast-simulating BBP/DEHA PVCP phantom, at ~23 mm vs. ~32 mm (based on qualitative limit of detectability). Because phantom optical attenuation is well matched (FIG. 10D), this difference must be due to higher acoustic attenuation in the BBP/DEHA phantom. Additionally, higher acoustic attenuation also appears to mitigate shallow reconstruction artifacts in BBP/DEHA phantoms. Penetration depth in chicken breast was similar to that observed in both the disclosed BBP/DEHA PVCP phantom and in commercial PVCP phantoms; phantoms were not intended to specifically simulate chicken tissue, but results demonstrate that phantoms produce realistic performance compared with an in vivo environment. These results illustrate the impact of tunable phantom acoustic properties on image quality testing and performance metrics.

Figure 11A:
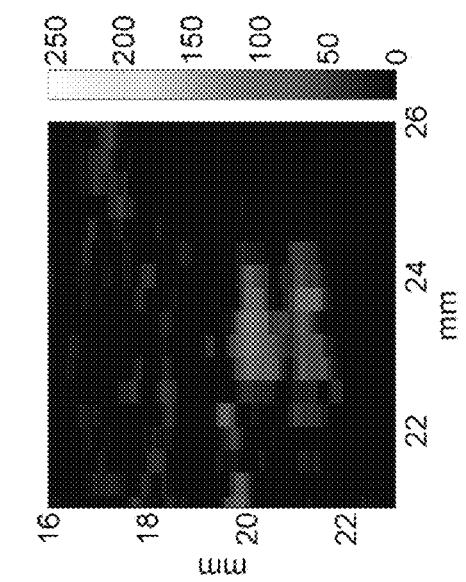
FIGS. 11A-11C are a set of photoacoustic images of a 1-mm diameter channel at ~2 cm depth in a commercial PVCP phantom, imaged assuming a reconstruction algorithm input value of speed of sound equal to (FIG. 11A) 1300 m/s, (FIG. 11B), 1400 m/s and (FIG. 11C) 1540 m/s. The actual speed of sound in this phantom is ~1400 m/s. The channel was filled a commercially available oxyhemoglobin solution (Multi4-L2, Instrumentation Laboratory, Bedford, Mass.)
Figure 11B:
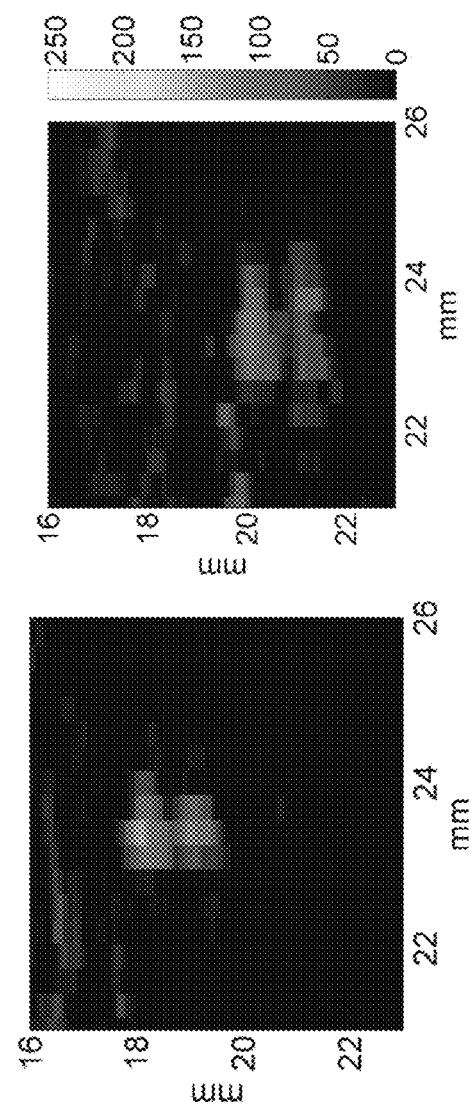
Figure 11C:
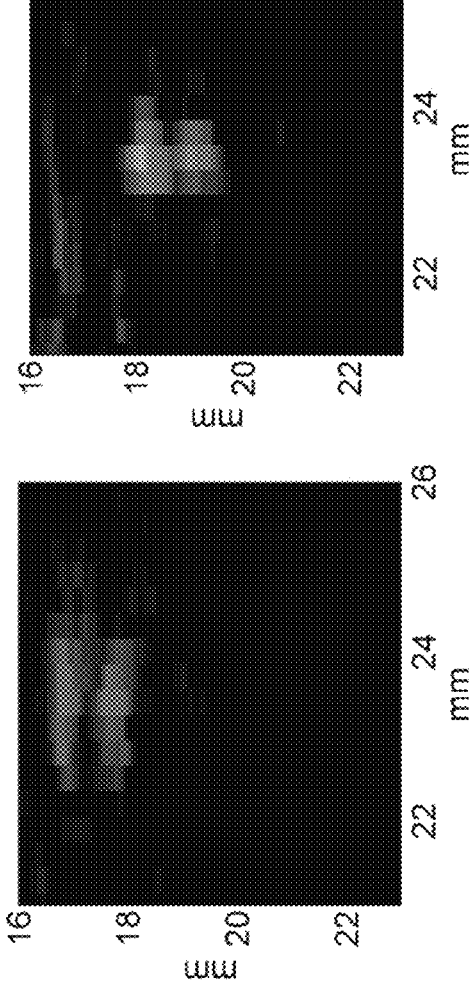
Figure 12A:
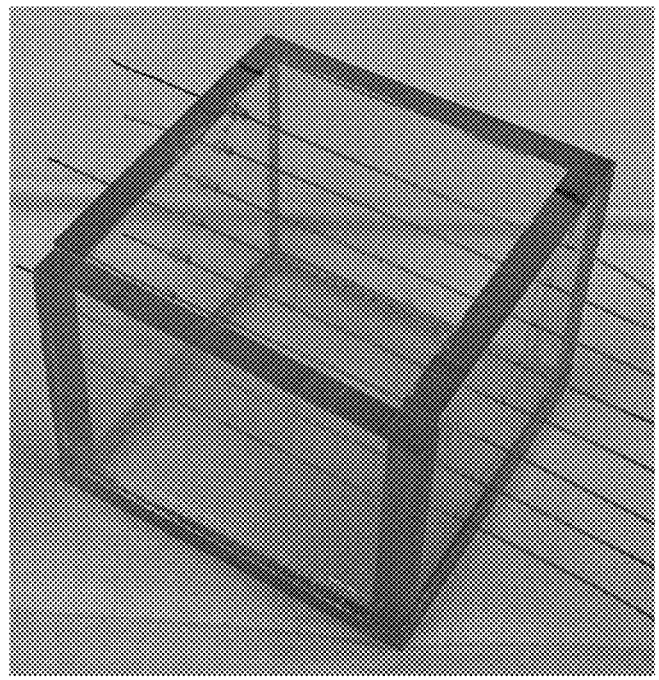
FIGS. 12A and 12B show a mold with retractable wires for use to form a disclosed phantom (FIG. 12A) and a phantom with fluid channels made using the mold (FIG. 12B).
Figure 12B:
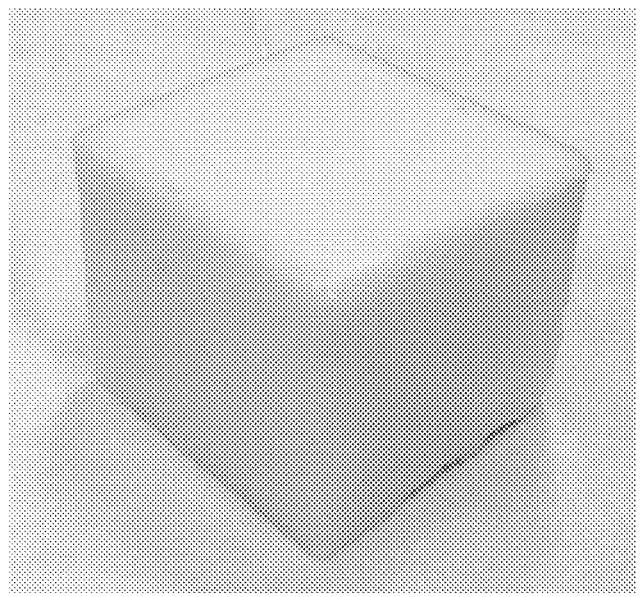

Representative images showing the effect of distortion on target visualization are shown in FIG. 11. Incorrect assumed values of speed of sound cause erroneous scaling in the axial direction, affecting perceived channel diameter as well as axial distance between channels. These errors also result in lateral resolution degradation due to smearing of the channels along circular wavefronts, which is equivalent to defocusing the beamforming data during reconstruction. Relative percent error in measured channel diameter relative to those in an image collected at 1400 m/s indicate a high correlation with the relative percent error in assumed speed of sound. This is expected as axial pixel length will be incorrectly scaled by a linear factor, specifically the ratio of assumed acoustic wavelength to true wavelength, where wavelengths are proportional to speed of sound. Since soft tissues vary between ~1400-1600 m/s, spatial measurement accuracy may degrade by up to 15% due to distortion effects in highly heterogeneous tissues such as breast. The acoustically tunable PVCP material could be used in future phantom designs to simulate the impact of acoustic heterogeneity on image quality, especially for spatial measurement accuracy testing.

Example 2

PVCP Formulations for Simulating Tissue

This example provides specific formulations for simulating particular tissues, and illustrates that the disclosed phantom materials possess broadly tunable optical and acoustic properties, enabling simulation of many types of biological tissues.

| Tissue type | Simulation Quality | BBP [% v/v] | DEHA [% v/v] | Heat stabilizer [% v/v plasticizer] | PVC [% m/m] | Silica [mg/mL] | $TiO_2$ [mg/mL] | BPC [% v/v] |
|---|---|---|---|---|---|---|---|---|
| breast (fatty) | Excellent | 30 | 70 | 1 | 10 | 25 | 1.5 | 0 |
| Breast (moderate) | Excellent | 75 | 25 | 1 | 10 | 50 | 1.75 | 0.002 |
| breast (parenchyma/dense) | Excellent | 90 | 10 | 1 | 10 | 100 | 2.5 | 0.002 |
| Skin | Good | 99 | 1 | 1 | 10 | 200 | 2.5 | 0.008 |
| abdominal fat | Excellent | 40 | 60 | 1 | 10 | 0 | 1.5 | 0 |

| | | | -continued | | | | | |
|---|---|---|---|---|---|---|---|---|
| Brain | Good | 90 | 10 | 1 | 8 | 25 | 2.5 | 0 |
| Liver | Moderate | 75 | 25 | 1 | 8 | 50 | 1.5 | 0.004 |
| Skeletal muscle | Moderate | 75 | 25 | 1 | 8 | 100 | 2.0 | 0.012 |

| Tissue type | Tissue SoS [m/s] | PVCP SoS [m/s] | Tissue Attenuation, (alpha = a*f^b) a [dB/cm/MHz^b] | b [—] | f [MHz] | Tissue alpha at 7 MHz [dB/cm] | PVCP alpha at 7 MHz [dB/cm] | $\mu_a$ [1/cm] (800 nm) | $\mu_s'$ [1/cm] (800 nm) |
|---|---|---|---|---|---|---|---|---|---|
| breast (fatty) | 1430-1450 | 1435 | 1.28 | 0.73 | 6 to 18 | 5.3 | 6 | 0.05 | 6 |
| Breast (moderate) | 1450-1500 | 1480 | 0.7 | 1.3 | N/A (fitted from fatty and dense values) | 9 | 8 | 0.1 | 8 |
| breast (parenchyma/dense) | 1500-1520 | 1500 | 0.87 | 1.5 | 3 to 7 | 16.1 | 15 | 0.13 | 12 |
| Skin | 1560 | 1520 | 3 | 0.7 | 1 to 5 | 11.7 | 13 | 0.2 | 15 |
| abdominal fat | 1420-1460 | 1450 | 0.3-5.2 | 0.4-1.4 | 1 to 6 | 8-11 | 9 | 0.08 | 10 |
| Brain | 1550 | 1500 | 0.58-0.60 | 1.20-1.46 | 1 to 6 | 7.5 | 7 | 0.08 | 15 |
| Liver | 1540-1580 | 1480 | 0.4 | 1.139 | 1-10 | 3.7 | 5 | 0.6-1.0 | 10 |
| Skeletal muscle | 1560 | 1480 | — | — | 4.3 | 8.6 | 9 | 0.3 | 8.5 |

Example 3

Phantom Fabrication

This example illustrates fabrication materials and methods for constructing one embodiment of an phantom using PVCP including a binary plasticizer including BBP and DEHA. The example is provided to illustrate an exemplary embodiment of a method of producing a disclosed phantom and is not intended to be limiting.

Materials/Chemicals
1. PVC dispersion resin (Geon 121A, Mexichem)
2. Plasticizers (e.g. BBP, DEHA)
3. Heat stabilizer (M-F manufacturing Co)
4. Titanium dioxide (anatase, Sigma-Aldrich)
5. Black Plastic colorant (BPC, M-F manufacturing Co)
6. Ground silica, ~40-50 µm mean diameter (U.S. Silica)

Equipment
1. Custom mold (made of metal such as aluminum. Some thick acrylics may work with shorter lifespan due to thermal damage from molten PVCP)
2. Graduated cylinders (10, 25, 50 mL)
3. round bottom flask (250 mL)
4. #5 rubber stopper with tube connection to house vacuum line, including release valve (T-valve)
5. mass balance (220 g capacity)
6. magnetic stir plate
7. Dessicator
8. heated bath sonicator (T=40 C)
9. magnetic hot plate, max temp >=200 C (distinct from magnetic stir plate)
10. silicone oil bath (Dow Corning fluid 230H, max temp=230 C)
11. Heat-resistant gloves (e.g., terry cloth lab oven gloves)
12. safety goggles, other PPE as needed Protocol
1. Identify relative weight/volume of components to be used, depending on desired phantom optical and acoustic properties
   a. Plasticizer ratio (% v/v)
   b. Heat stabilizer content (% v/v plasticizer mixture)
   c. PVC resin (% m PVC/m plasticizers)
   d. TiO2 concentration (mg/mL)
   e. BPC concentration (% v/v plasticizer mixture)
   f. Silica concentration (mg/mL)
2. In a 500 mL beaker, combine plasticizers and heat stabilizer, stir for 5 min
3. While stirring plasticizer/heat stabilizer mixture, slowly add PVC resin. Allow mixing for 1 hr.
4. Place beaker in dessicator, degas solution for 1 hr.
5. Assemble all mold components while waiting for degas.
6. While waiting for degas, place silicone oil bath on hot plate, add magnetic stir bar and bring to 200 C.
7. If adding materials requiring sonication (e.g. TiO$_2$), pour 60 mL degassed PVCP into a 100 mL cylindrical jar. Close jar lid, suspend in bath sonicator set to 40 C, and sonicate for 30 minutes, stopping every ~10 minutes to manually agitate and break up aggregates.
8. Reintroduce sonicated volume to stock solution, stir for 5 min.
9. If adding BPC, typically only small volumes are needed (e.g. 0.003% v/v, or ~10 µL in 400 mL of solution). A pipette is required, and due to BPC's higher viscosity, proper pipetting techniques should be followed, including vertical drawing and pre-wetting.
10. After adding sonicated particle species, add silica beads and continue stirring for 15 minutes. Use a metal tool/scoop to check for large silica aggregates/clumps. Generally, silica will fall out of suspension quickly due to their higher density than the plastisol. Thus, the stock solution (and solutions undergoing heating/gelation) should be constantly stirred.
11. Pour 75 mL PVCP in a 250 mL round bottom flask. Add magnetic stir bar. Clamp flask to ring stand, attach stopper lower into silicone oil bath regulated at 200 C. Evacuate flask by switching the T-valve. Start a timer.
   a. The thermocouple connection is easily disrupted if you pull on it. Always grab from the yellow plug. If getting thermocouple error, reassemble/refit thermocouple cable assembly.
12. Around 5 min, the PVCP will begin to thicken, and RPM should be reduced to ~50-100 rpm.
   a. The choice of magnetic hot plate RPM is difficult, and depends on sample viscosity, which changes during the melting process, and also on stir bar size and magnetic strength, as well as on flask height above the plate/bath interface. The goal is to always have the stir bar moving and in the flask center. This promotes gas release, mixing, and heat stability. It is also nearly impossible to confirm that this is working as intended due to sample turbidity.

13. Around ~9-10 min, PVCP viscosity should decrease; increase RPM to ~200-300 rpm.
14. Around ~14-17 min, PVCP should be ready for pouring. First set out the mold. Switch T-valve to release vacuum suction in flask, then lift flask up ringstand. While holding the flask in place, open the clamp jaws and manually pour the PVCP into the mold.
    a. However, the amount of bubbles remaining varies significantly with PVCP composition. When working with a given PVCP recipe, the total heating time should be kept constant to improve consistency, but there is a tradeoff between heat stability and air release that must fit the application.

Example 4

Two-Layer Heterogeneous Breast Phantom for Photoacoustic Imaging

This example illustrates multi-layer breast phantoms incorporating vessel-simulating inclusions and realistic undulations at the fat/fibroglandular tissue interface for PAT imaging. The phantoms are comprised of novel polyvinyl chloride plastisol formulations mimicking the acoustic/optical properties of each tissue type. Resulting PAT images demonstrate that in heterogeneous tissue lateral size of imaging targets is sensitive to the choice of sound speed in image reconstruction. The undulating boundary can further degrade target's lateral size due to sound speed variation in tissue and refraction of sound waves at the interface. The extent of this degradation is also influenced by the geometric relationship between an absorber and the boundary. Results indicate that a homogeneous phantom matrix may underestimate the degradation of PAT image quality in breast tissue, whereas the provided heterogeneous phantoms provide more realistic testing through improved reproduction of spatial variations in physical properties Most PAT phantoms presented in the literature use a homogeneous background medium to simulate healthy tissue. However, breast tissue is a highly heterogeneous mixture of fat and fibroglandular tissue. The fibroglandular tissue is surrounded by, admixed with, and covered by a layer of fatty tissue. These two types of tissue have been reported to have substantially different optical and acoustic properties, and spatial variations of these properties in breast may cause errors in image reconstruction or changes in image quality. Homogeneous phantoms with uniform optical and acoustic properties may be suitable for basic performance testing, but it is likely that heterogeneous phantoms are needed to simulate complex tissue interactions that affect in vivo imaging performance. In order to realize such phantoms, the spatial distribution of TMMs and their optical and acoustic properties must mimic those reported for complex breast tissue.

The acoustic properties affecting PAT system performance include speed of sound frequency-dependent acoustic attenuation, and backscattering coefficient. Speed of sound describes the propagation velocity of acoustic pressure waves in the medium and is a key input parameter to image reconstruction algorithms such as delay-and-sum beamformer, where the received ultrasound signals are delayed to account for time-of-flight differences and summed at each reconstruction point. Both in vitro measurements on excised breast tissues maintained at 37° C. and in vivo measurements reported sound speeds of less than 1460 m/s in fat and sound speeds more than 1500 m/s in fibroglandular tissue over the frequency range of 2 MHz to 13 MHz. The spatial variation in breast speed of sound due to the heterogeneous distribution of fatty and fibroglandular tissue can decrease the spatial size of imaging targets and accuracy of spatial registration of ultrasound and photoacoustic images when a single uniform speed of sound is assumed in the image reconstruction. Breast acoustic attenuation has been extensively characterized, particularly as a function of breast composition. Ex vivo and in vivo measurements have demonstrated lower acoustic attenuation in fatty tissue and higher attenuation in fibroglandular tissue over from the frequency range of 1 MHz to 10 MHz. Both speed of sound and acoustic attenuation of whole breast also vary with menopausal status and age.

Because many PAT systems are bi-modal, allowing for overlay of co-registered B-mode ultrasound images, complex PAT tissue phantoms should be suitable for imaging in both domains. Thus it is important to account for acoustic backscattering coefficient, which describes the relative amount of energy reflected back towards an acoustic emitter. This mechanism represents the primary source of contrast in B-mode ultrasound images. It is well-known that breast fatty and fibroglandular tissues have substantially different backscattering properties, as fibroglandular tissues produce high intensity in B-mode ultrasound images while fatty tissue is relatively hypoechoic. Ex vivo and in vivo studies have demonstrated that breast fibroglandular tissue may possess an order of magnitude higher backscattering coefficient compared to fatty tissue.

This example illustrates two-layer PVCP phantoms with acoustic and optical properties mimicking fatty and fibroglandular tissue regions arranged in a tissue-relevant layered geometry. This phantom also included an undulating boundary between the two layers, simulating realistic structures that may cause refraction of sound propagation, and the spatial size of embedded imaging objects with the same dimension was characterized as a function of depth, image reconstruction parameters, and location along the undulation pattern.

Methods

Phantom Fabrication

PVCP is a suspension of PVC resin in liquid plasticizers, which fuses into a gel after heating to high temperatures (~180° C.). A dispersion-grade PVC resin (Geon 121A, Mexichem Specialty Resins, Inc., Avon Lake, Ohio), benzyl butyl phthalate (BBP) (Sigma-Aldrich, St Louis, Mo.), and di(2-ethylhexyl) adipate (DEHA) (Sigma-Aldrich) were used to make phantoms described in this example. Two TMM formulations for simulating a and c type breast tissues, labeled as a-fat and c-fibrogland.+fat, respectively were used (see the following table). The speed of sound and acoustic attenuation were tuned by modifying the volume ratio between the two plasticizers (BBP and DEHA) and the mass/mass PVC concentration. Acoustic backscattering was adjusted by adding soda lime glass microspheres (Spheriglass A, Potter Industries LLC, Malvern, Pa.). Microspheres with diameters of 38-60 µm and 63-75 µm were used in the formulations for a-fat and c-fibrogland.+fat tissue, respectively. Optical scattering was induced by adding anatase titanium dioxide (Sigma-Aldrich).

TMM formulations for stimulating breast fat (a-fat) and fatty fibroglandular (c-fibrogland.+fat) tissue.

| Breast tissue type simulated | BBP (v/v) | DEHA (v/v) | PVC (m/m) | Microspheres (mg/mL) | TiO$_2$ (mg/mL) |
|---|---|---|---|---|---|
| a-fat | 42% | 58% | 8.4% | 10 (small) | 2.293 |
| c-fibrogland. + fat | 87% | 13% | 8.6% | 30 (large) | 2.947 |

PVCP phantoms were fabricated as generally described in the prior examples. Briefly, a large stock PVCP solution was prepared by mixing binary mixture of plasticizers with 1% v/v calcium-zinc heat stabilizer (M-F Manufacturing Co., Fort Worth, Tex.), adding PVC resin, then stirring for 30 min followed by degassing for 60 min. A 75 mL volume of PVCP solution was mixed with TiO$_2$, sonicated at 40° C. for 40 min, and then reintroduced to the original PVCP stock solution and stirred for 5 min. Glass microspheres were added to a 100 mL batch of PVCP solution and stirred for 5 min. This batch volume was then poured into a 200 mL round bottom flask immersed in a magnetically-stirred oil bath maintained at 190° C. using a thermocouple. The flask, which contains a stir bar, was evacuated and stirred at ~375 rpm for 15 min. The flask was then removed from the oil bath and stirred magnetically at a gradually reducing speed until the flask temperature was ~110° C. After reaching this temperature, PVCP was poured into phantom molds. This cooling protocol was used to increase PVCP viscosity at time of pouring, which would minimize settling of the glass microspheres. Characterization phantom samples were first produced, including 5 mm thick, 38 mm diameter disks for speed of sound, acoustic attenuation and optical property measurements. A 20-mm-thick, 38-mm-diameter disk was produced for backscatter coefficient measurements.

Acoustic Characterization

The characterization of PVCP-based TMM speed of sound values was performed using 5 mm thick, 38 mm diameter disks as discussed in Example 1. Briefly, a through-transmission technique was performed using a pair of identical broadband transducers (V320, Panametrics, Waltham, Mass.) with focal lengths of 3.81 cm, diameters of 1.27 cm, center frequencies of 7.5 MHz. One transducer was used as a transmitter while the other served as a receiver, facing each other in a water bath. The PVCP disk was positioned at both transducers' focus. Both transducers were connected to a pulser/receiver (Model 5800PR, Panametrics). The received ultrasound signals were then digitized (8 bit, 50 MHz) using a 400 MHz oscilloscope (9310C, Teledyne LeCroy, Chestnut Ridge, N.Y.). Speed of sound in the sample disk, $c_s$, was calculated as $$c_s = \frac{c_w}{1 + \frac{\Delta t}{\Delta x}c_w}$$

where $c_w$ is the speed of sound in water, $\Delta x$ is the sample thickness, and $\Delta t$ is the time delay between pulses travelling through water path with a sample and a water-only path. Four spatial locations in the sample were used for through-transmission measurement. At each location, sixty measurements were averaged for the time delay calculation and sample sound speed estimation. Mean and standard deviation were calculated for the four estimates per sample.

Frequency dependent acoustic attenuation coefficient was measured using the same experimental layout and calculated as $$\alpha_{dB}(f) = \frac{10}{\Delta x}\log\left(\frac{P_w(f)}{P_s(f)}\right)$$

where $P_w(f)$ is the acoustic power spectrum measured through a water-only path, and $P_s(f)$ is the power spectrum measured through the sample. Using the same data acquisition procedure as above, sample power spectra at each of the four sample locations were calculated over 4-9 MHz, averaged for sixty measurements, and then used to calculate the attenuation coefficient in dB $\alpha_{dB}$ as a function of frequency f. The coefficient was then fitted to the power-law relationship $\alpha_{dB}(f)=\alpha f^\eta$, where $\alpha$ and $\eta$ are fitting parameters. Mean and standard deviation were calculated for the set of four fitted attenuation spectra for each sample.

Backscatter coefficients were measured using the same setup except in reflection mode using one broadband transducer. Briefly, the central plane of a 20-mm-thick TMM disk was positioned at the focus of the transducer, parallel to the surface of the transducer. Pulse-echo signal was recorded at 30 spatial positions across the face of the disk by translating the TMM disk with a spacing of 0.5 mm parallel to the transducer surface and averaged 20 measurements at each position. The signal was gated to isolate a region of 1.5 mm thick in the interior of the disk centered about the focal distance of the transducer. The power spectrum of this gated signal was denoted as $P_s(f)$. The spatial average was denoted by $\overline{P_s(f)}$. Reference signal was measured using the same approach but replacing the TMM disk with a planar reflector made of low-density polyethylene at the transducer focus. This type of material was chose to avoid signal saturation during the measurements. The normalized power spectrum $\overline{P_o(f)}$ was calculated as $$\overline{P_o(f)} = \frac{\overline{P_s(f)}}{P_r(f)}H(f)$$

where $P_r(f)$ is the acoustic power spectrum of the gated signal from the planar reflector; $H(f)$ is a function used to compensates for attenuation effects and is calculated as $$H(f) = \frac{4\alpha^2(f)L^2}{(1 - e^{-2\alpha(f)L})^2}e^{4\alpha(f)x_0}$$

Here $$\alpha(f)\left(= \frac{\alpha_{dB}(f)}{8.69}\right)$$

is the frequency-dependent attenuation coefficient in Np/cm for the sample over the gated volume, the gated length L is 1.5 mm, $x_0$ is the distance from the TMM surface close to the transducer to the center of the gated signal. The backscatter coefficients were then calculated after properly compensating for the transducer geometry from the normalized power spectrum as $$\eta(f) = 2.17D(G_p)\frac{\gamma^2 F^2}{A_0 L}\overline{P_o(f)}$$

$$D(G_p) = |e^{-iG_p}(J_0(G_p) + iJ_1(G_p)) - 1|^2$$

where $A_0=\pi R^2$ is the aperture area of the transducer with radius R; $\gamma$ is the pressure reflection coefficient of the planar reflector (in this case, $\gamma=0.715$); F is the transducer focal length $$G_P = \frac{kR^2}{2F}$$

is the pressure focusing gain of the transducer; k is the wave number; $J_0(\cdot)$ and $J_1(\cdot)$ are $0^{th}$ and $1^{st}$ order Bessel functions. The coefficient was then fitted to the power-law relationship $\eta(f)=bf^m$, where b and m are fitting parameters. Mean and standard deviation were calculated for the set of 30 fitted backscatter spectra for each sample.

Optical Characterization

TMM optical properties were characterized using spectrophotometry as described in Example 1. Briefly, PVCP disks were placed between 1-mm-thick, 75 mm×50 mm glass slides (refractive index=1.51) and diffuse transmittance and reflectance measurements were made over 400-1100 nm using an integrating sphere spectrophotometer (Lambda 1050, PerkinElmer, Waltham, Mass.). NIST-traceable Spectralon standards were used to normalize measurements. Optical absorption coefficients ($\mu_a$) and reduced scattering coefficients ($\mu_s'$) were calculated using the inverse adding-doubling (IAD) method, which requires a priori knowledge of the anisotropy factor and refractive index of the sample. The refractive indices of BBP and DEHA are 1.540 and 1.447, respectively; using the Lorentz-Lorenz mixture rule for refractive index, α-fat and c-fibrogland.+fat TMMs are expected to have a refractive index of 1.485 and 1.528, respectively. Scattering anisotropy factor was assumed to equal 0.7 based on Mie scattering theory of $TiO_2$ (using an open-source MATLAB software) for both TMMs.

Homogeneous and Heterogeneous Phantoms

A homogeneous phantom (86×60×35 mm, 180.6 mL) was constructed by pouring PVCP (c-fibrogland.+fat formulation) into a mold containing six 0.5 mm diameter steel wires spaced 5 mm apart vertically and horizontally, as shown in FIG. 13A. Metallic wires were chosen because they are visible in both ultrasound and PAT images and easily aligned due to their high tensile strength. The diameter of the wire is similar to the size of a brachytherapy seed and in the diameter range of blood vessel. Since the phantom was larger than the 100 mL batch volume, the phantom was produced by sequential layer pouring. Prior to pouring the second layer, a heat gun was applied to the surface of the first layer to produce a thin layer of remelted PVCP. As the second layer was poured, this remelting prevented formation of air gaps and poor PVCP bonding, which would cause photoacoustic artifacts at the boundary. Both layers use the c-fibrogland.+fat formulation to mimic dense breast. A heterogeneous phantom of the same size was created using the same mold shown in FIGS. 13A and 13C, but pouring the a-fat PVCP formulation for the first layer, and the c-fibrogland.+fat formulation for the second layer. This phantom also has an undulating boundary between its two layers to mimic the boundary between superficial fatty tissue and deeper fibroglandular tissue in breast. An in vivo ultrasound B-mode image is shown in FIG. 13D as an illustration of this tissue structure. To create this feature, an aluminum block with machined concave surfaces (FIG. 13C) was inserted into the mold. PVCP solution for the first (fatty) layer was poured onto the plate and after cooling, the plate was removed resulting in convexities at the surface of the layer onto which the deep (fibroglandular) layer of TMM was poured. Four different radii of curvature were used at the boundary layer. The radii of curvature were designed to reflect average curvatures found by analysis of the fat-glandular tissue boundary in the ultrasound B-mode images of 10 patients acquired for a different research study (an IRB-approved ultrasound elasticity study conducted at George Washington University). The analysis demonstrated that the boundary between superficial and deep breast layers was composed of convexities that could be grouped into several categories with different mean radii. Thus, the boundary convexities (from left to right in FIGS. 13A and 13B have radii of curvature of 30 mm, 24 mm, 16 mm, and 16 mm, and boundary angles of 58°, 66°, 81° and 41°, respectively.

Imaging was performed using a the PAT system described in the above Examples, composed of a cart-based tunable near-infrared (NIR) pulsed laser (Phocus Mobile, Opotek, Inc., Carlsbad, Calif.) and a research-grade ultrasound system (Vantage 128, Verasonics, Inc., Kirkland, Wash.). Phantoms were imaged at 750 nm and a radiant exposure of 20 mJ/cm$^2$. Acoustic sensing was performed using a 128-channel ultrasound linear array transducer with a 7.5 MHz center frequency, 7.0 MHz bandwidth, and 38.1 mm length (L11-4v, Verasonics). A significant clutter artifact encountered using this approach was caused by photoacoustic generation at the transducer face resulting from high fluence at the phantom surface. To reduce this effect, the transducer surface was covered with aluminum foil and coupled to the transducer surface with a thin layer of acoustic coupling gel. While the foil can still cause clutter artifacts, the overall image quality is significantly improved. The transducer was then brought into contact with the phantom top surface using a thin layer of water as the couplant. One-way delay-sum beamforming was applied to the received radio-frequency ultrasound signals to create photoacoustic images with dynamic receiving focusing. Data were apodized using Hanning windows, and F number was set at 0.9. The reconstruction speed of sound was varied between 1437 m/s and 1500 m/s in the heterogeneous phantom and between 1440 m/s and 1560 m/s in the homogeneous phantom. The spatial size of the metal wires with the same physical dimension at different depth across the phantom are estimated and compared in the reconstructed PAT imaging domain. The axial and lateral spatial size of these imaged targets were defined as the full width half maximum (FWHM). All PAT images generated in this study were normalized using the same maximum intensity value. B-mode ultrasound images were also acquired using the same PAT system, applying two-wave delay-sum beamforming to received data from plane wave transmission. Gray levels for all ultrasound images were normalized to a single maximum intensity value.

Undulation Effects in Heterogeneous Phantoms

To evaluate the effects of the boundary undulation between superficial (fatty) and deeper (fibroglandular) layers on PAT image quality, a second complex phantom was constructed using the same process as the heterogeneous phantom described above. Instead of wire inclusions at different depths, a horizontal array of six polytetrafluoroethylene (PTFE) tubes (Component Supply Co., Fort Meade, Fla.) were positioned at a depth of 20 mm as shown in FIG. 13B. These tubes have an inner diameter of 0.559 mm and a wall thickness of 0.150 mm and were filled with an India ink solution. A 1% aqueous solution of India Ink was used (Speedball, Statesville, N.C.) with an optical absorption of 4.6 cm$^{-1}$ at 750 nm. This value was chosen to simulate venous blood with hemoglobin concentration of 15 g/dL and oxygen saturation of 70%. Similarly as with the target size measurements, the spatial extent of these photoacoustic signals are also estimated using their FWHM in the corresponding direction. There are signals close to the top and bottom of the tubes. Those close to the top wall were used for spatial size and intensity estimation. Axial size was calculated by doubling the half width at half maximum of the rising part of the bell-shaped signal closest to the surface of the phantom since the falling portion of the bell-shaped signal was affected by the signal close to the bottom wall of the tubing.

Results and Discussion

Acoustic Properties

Figure 14:
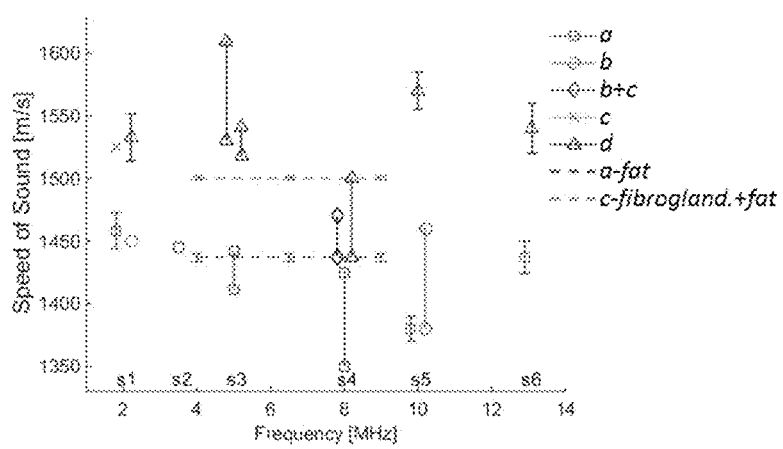
FIG. 14 shows a graph illustrating the speed of sound measured for four types of breast tissue based on calculations from references s1-s6 and that of two formulated PVCP phantoms (a-fat and c-fibrogland.+fat, as described in Example 4)). The prior art references are as follows: s1: Kossoff et al., J Acoustical Society America 53(6), 1730-1736, 1973); s2: Carson et al. (Science 214(4525), 1141-1143, 1981); s3: Glover (Ultrasonic Tissue Characterization II 3(1), 117-127, 1977); s4: Greenleaf and Bahn (*IEEE Trans. Biomed. Eng.* 28(2), 177-185, 1981); s5: Bamber, "Ultrasonic propagation properties of the breast," in Ultrasonic Examination of the Breast J. Jellins, and T. Kobayashi, Eds., John Wiley & Sons Ltd. (1983); s6: Foster et al. (Ultrasonic Imaging 6(3), 243-261, 1984).

Speed of sound values reported in the literature are categorized into four BI-RADS tissue types (a, b, c and d) according to the description of tissue types in the literature (fat, fatty fibroglandular, less fatty fibroglandular and fibroglandular tissue in order), as shown in FIG. 14. Fatty breast tissue is labeled as b+c. These values are reported as either mean and standard deviation or as the range of values. There are large variations in speed of sound for each tissue type. The general trend of increasing speed of sound is reported with increasing amounts of fibroglandular tissue. The formulations provided herein are designed to achieve a speed of sound of 1437 m/s for a-fat and 1500 m/s for c-fibrogland.+fat. These values fall in the sound speed range of tissue types of a and c and are consistent with the references.

Figure 15:
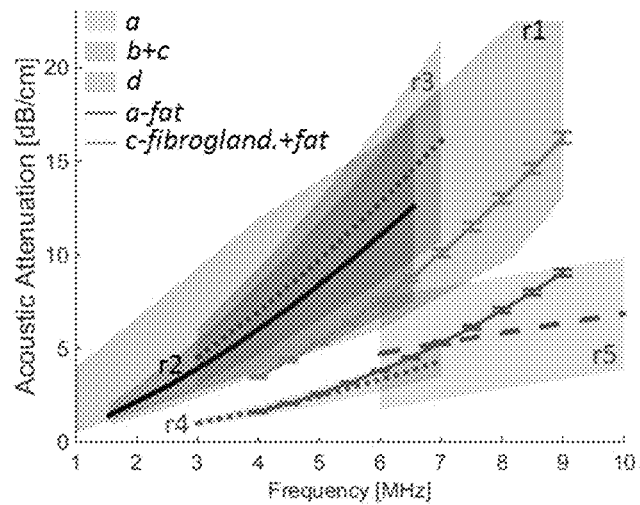
FIG. 15 shows a graph illustrating acoustic attenuation coefficient measured for 4 types of breast tissue from references r1-r5 and of two formulated PVCP phantoms (a-fat and c-fibrogland. +fat). The references are as follows: r1: Bamber, "Ultrasonic propagation properties of the breast," in Ultrasonic Examination of the Breast, Jellins, and Kobayashi, Eds., John Wiley & Sons Ltd. (1983); r2: Foster and Hunt (*Ultrasound in medicine & biology* 5(3), 257-268, 1979); r3: D'Astous and Foster (Ultrasound Med. Biol. 12(10), 795-808, 1986); r4: D'Astous and Foster (Ultrasound Med. Biol. 12(10), 795-808, 1986) (37); r5: Nasief et al., *J. Ultrasound Med.* 34(11), 2007-2016, 2015)

Acoustic attenuation values reported in the literature are shown in FIG. 15. Shaded areas represent either the range of values or standard deviation around the plotted mean values. The trend of increasing sound speed with increasing glandular tissue content is also observed in acoustic attenuation values with lower values in fat and higher ones in fatty-fibroglandular tissue. The acoustic attenuation of the phantom formulations are consistent with those in the references and are representative of tissue types a and c.

Figure 16:
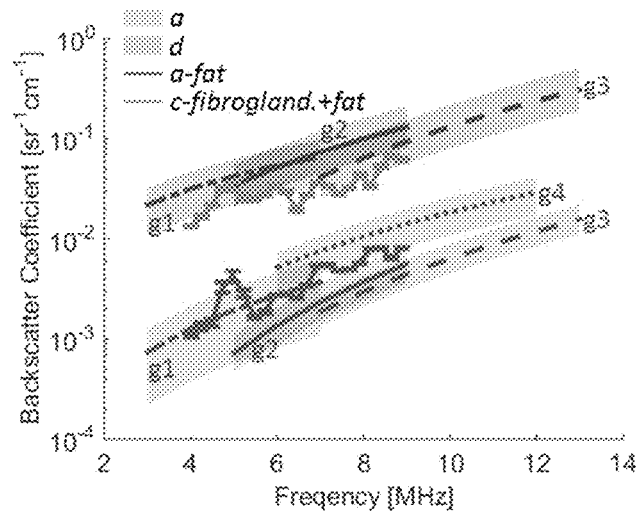
FIG. 16 shows a graph illustrating backscatter coefficients for 2 types of breast tissue from references g1-g4 and that of two formulated phantoms (a-fat and c-fibrogland.+fat). The references are as follows: g1: D'Astous and Foster (Ultrasound Med. Biol. 12(10), 795-808, 1986); g2: Anderson et al. (*Ultrasound Med. Biol.* 27(1), 75-81, 2001) using 7.5 MHz transducer; g3: Anderson et al. (*Ultrasound Med. Biol.* 27(1), 75-81, 2001) using 10 MHz transducer; g4: Nasief et al., *J. Ultrasound Med.* 34(11), 2007-2016, 2015).

Acoustic backscatter coefficients reported in the literature are shown in FIG. 16 for tissue types a and d. Tissue type d has significantly higher backscatter coefficients than type a. The a-fat formulation gives backscatter coefficient with that of type a reported. The c-fibrogland+fat formulation gives backscatter coefficients slightly lower than the reported values for d, which is consistent with the dependence of acoustic properties on the proportion of fibroglandular tissue present.

Optical Properties

Sandell et al. (*Journal of Biophotonics* 4(11-12), 773-787, 2011) summarized the optical properties of fatty breast tissue measured with four in vivo experimental methods. The resulting 95% confidence intervals are shown in FIG. 17. Jacques (*Phys. Med. Biol.* 58(11), R37-R61, 2013) focuses on the optical properties of fatty breast which can be represented by the fitted curves. The mean and standard deviation of these curves are also shown in FIG. 17 as shaded areas with the mean at the center. The range of values in Jacques's review paper overlapped with the lower values in Sandell et al. The large variation might be due to the variation in a range of biological factors such as breast density across subjects and the measurement variation among experimental methods. Optical properties for four tissue types are reported by Taroni et al. (*PLoS One* 10(6), 2015). The values shown in FIG. 17 are calculated from the supplementary material of Taroni et al. The standard deviations were only shown for tissue type c for clarity. The optical properties of the two phantom formulations were designed to be similar to isolate the effect of distinct acoustic properties in heterogeneous phantom on image quality. As shown in FIG. 17A, the optical absorptions of two formulas are similar to each other except for the wavelength range 900-940 nm. These values are slightly higher than results reported by Taroni et al. over 670-920 nm wavelengths, but still in the range of values reported by Sandell et al. The reduced scattering coefficients of both phantom materials are similar and consistent with the values of c reported by Taroni et al. over the wavelength range of 600-1000 nm.

Homogeneous and Heterogeneous Phantoms

Figure 18A:
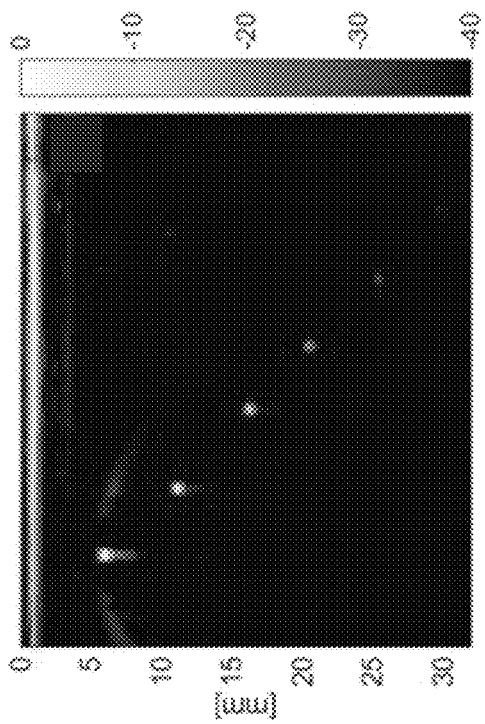
FIGS. 18A-18D show ultrasound (18A and 18C) and PAT (18B and 18D) images of heterogeneous (18A and 18B) and homogeneous (18C and 18D) phantoms containing six 0.5-mm-diameter wires.
Figure 18B:
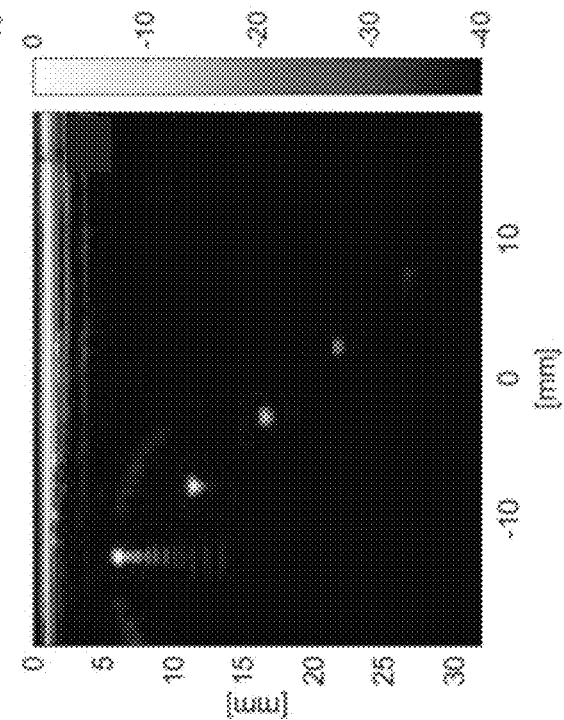
Figure 18C:
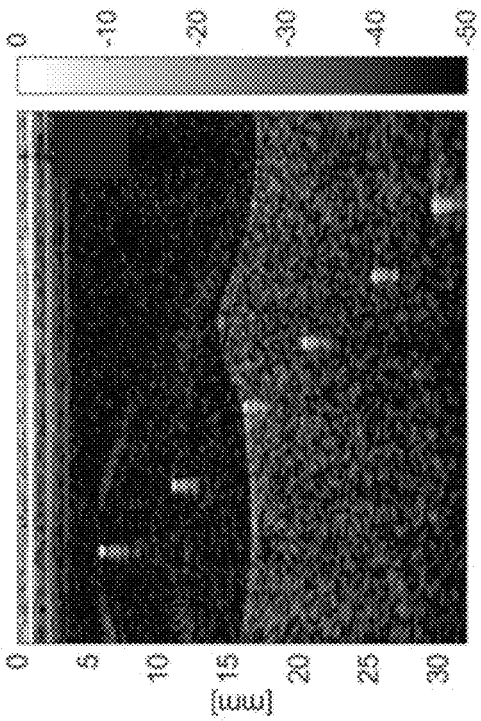
Figure 18D:
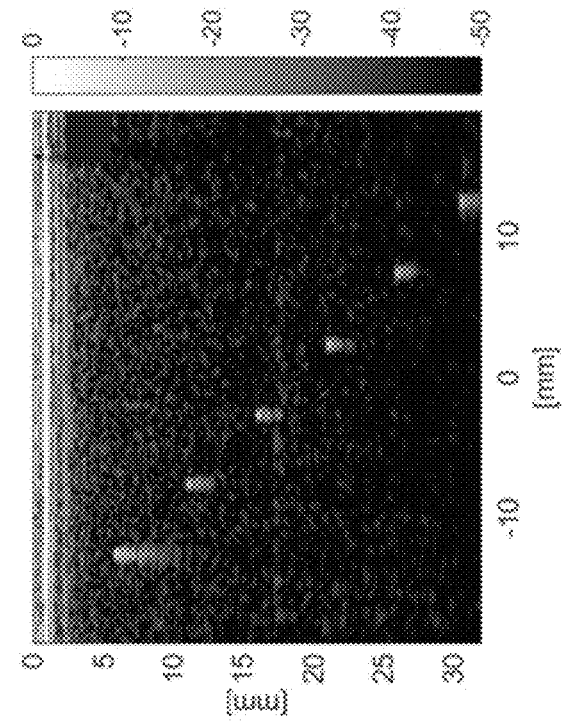

The TMM formulations described herein enable the construction of homogenous and heterogeneous phantoms. FIGS. 18A and 18B are the reconstructed ultrasound and PAT images of a heterogeneous phantom with six wires using the speed of sound of the top layer, 1437 m/s. FIGS. 18C and 18D are the reconstructed ultrasound and PAT images of homogeneous phantom with six wires using a speed of sound of 1500 m/s. The heterogeneous phantom can be used to evaluate the image quality of the dual-modality photoacoustic/ultrasound system. The ultrasound images shown in FIG. 18A provide valuable anatomical information mimicking the clinical imaging environment. This is due to a realistic difference in backscatter coefficient for the two layers.

Effects of Reconstruction Speed of Sound on PAT Image Quality

Figure 19A:
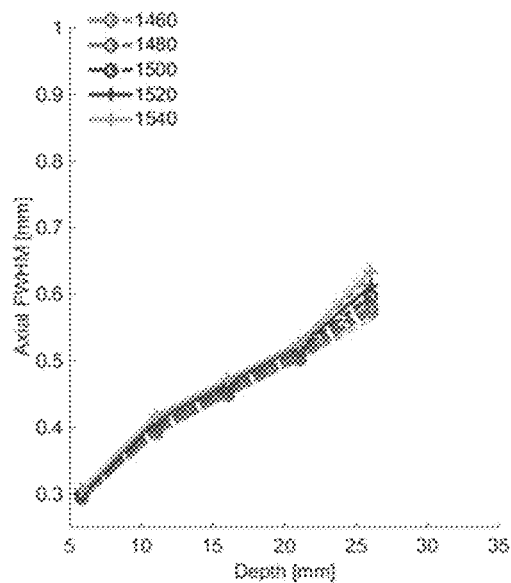
FIGS. 19A-19D are a set of graphs showing axial target signal full width half maximum (FWHM) (19A), lateral FWHM (19B) estimated using reconstruction sound speed from 1460 m/s to 1540 m/s in a homogeneous phantom, spectrum FWHM (19C), and central frequency (19D) estimated using true sound speed of 1500 m/s in the delay-and-sum PAT reconstruction.
Figure 19B:
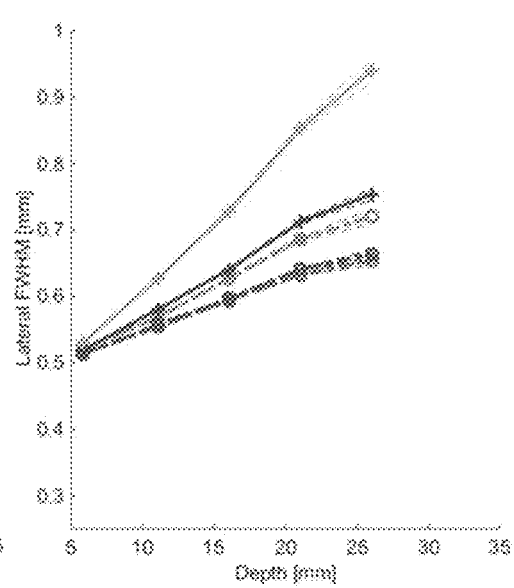
Figure 19C:
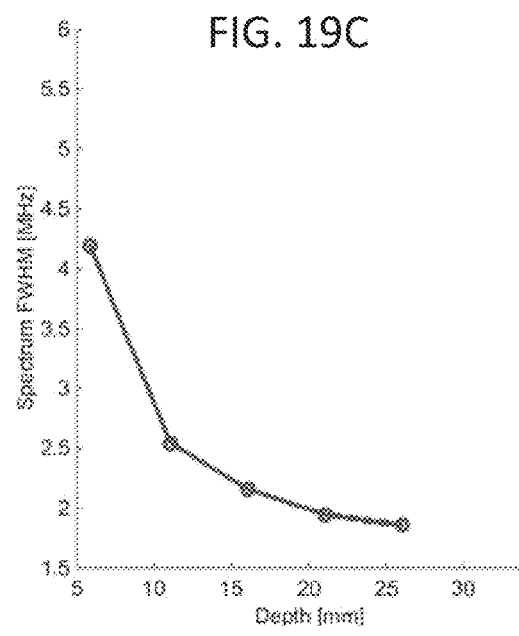
Figure 19D:
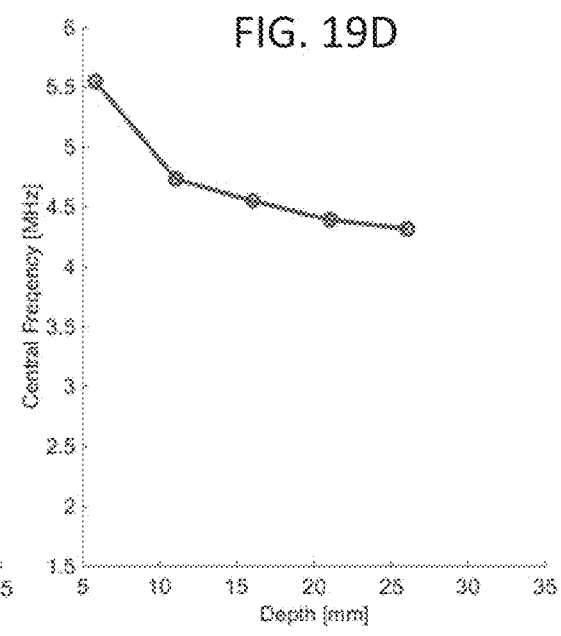

The heterogeneous phantom described above provides a realistic imaging environment to evaluate the effects of boundary undulation and reconstruction speed of sound on PAT target size. The conventional delay-and-sum reconstruction algorithm assumed a homogeneous speed of sound; the mismatch between this assumed speed of sound value and tissue's true sound speed will lead to overestimation in PAT target size due to incorrect signal alignment. Using a homogeneous phantom, FIG. 19A demonstrates that axial FWHM of targets with the same dimension at different depths is not sensitive to the reconstruction speed of sound. The axial FWHM of the first three targets are smaller than the wire diameter; because of the high optical absorption coefficient of the metal target, target light penetration is shallow and thus photoacoustic signals are generated only near the target surface. FIG. 19B shows that lateral FWHM is sensitive to reconstruction sound speed and that reconstruction sound speeds higher than the true values result in greater degradation than do sound speeds lower than the true value. For example, underestimating sound speed by 40 m/s (1460 m/s, green curve) results in approximately one third the lateral resolution degradation compared with overestimating sound speed by 40 m/s (1540 m/s, gold curve) for depths between 10 and 25 mm. At all speed of sound values, both axial and lateral FWHMs increase as the depth increases. This is mainly due to the TMM's nonlinear acoustic attenuation frequency spectrum, which causes a decrease in the spectral bandwidth shown in FIG. 19C and a reduction of central frequency shown in FIG. 19D.

Figure 20B:
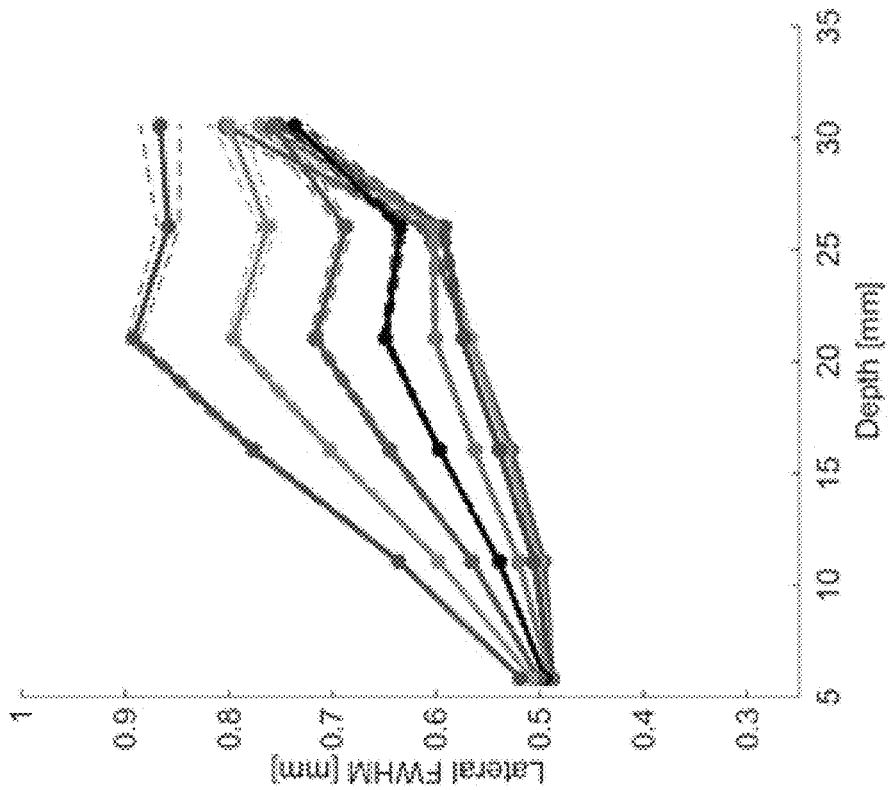
FIGS. 20A and 20B are a set of graphs showing axial FWHM (20A) and lateral FWHM (20B) estimated using reconstruction sound speed from 1437 m/s to 1500 m/s in a heterogeneous phantom.
Figure 20A:
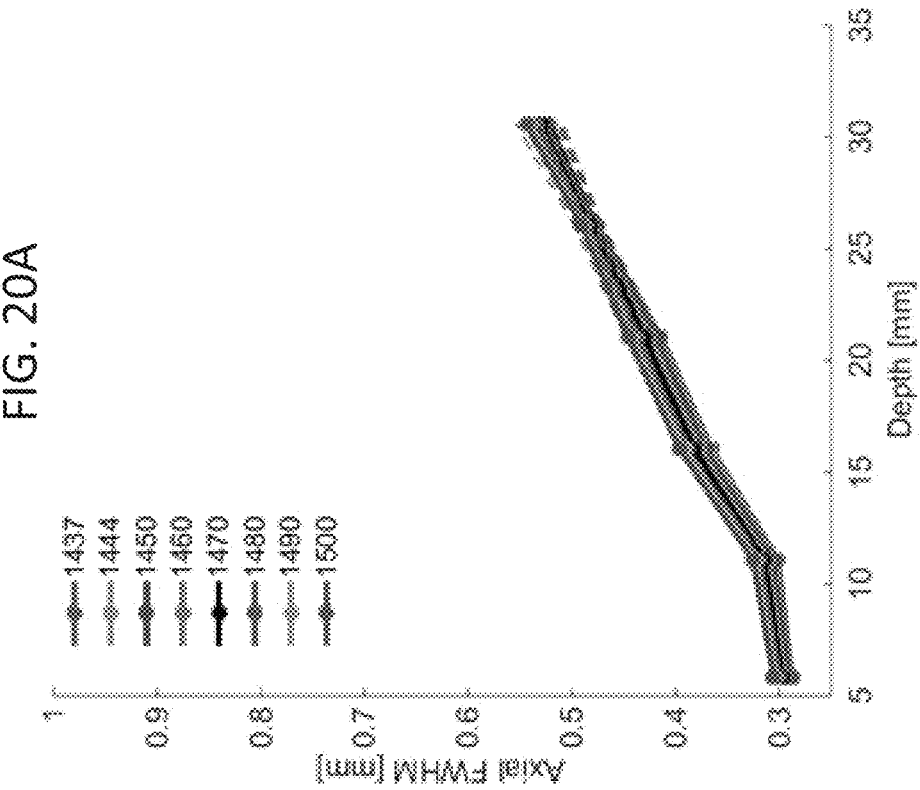

The heterogeneous phantom contains a top layer with a sound speed of 1437 m/s and a bottom layer with a speed of 1500 m/s. The choice of reconstruction speed of sound affects the estimation of spatial size of the imaging targets in the two layers differently. As in the homogeneous phantom, axial resolution is similar across all reconstruction speeds in the heterogeneous phantom (FIG. 20A). Lateral resolution is more severely degraded along the depth for the first three targets (located in the top layer) than in the fifth and sixth targets (in the bottom layer) (FIG. 20B). The following two observations have contributed for this phenomenon. First, applying overestimated reconstruction sound speed in the top layer can cause more degradation in lateral FWHM calculation of imaging targets than applying underestimated reconstruction sound speed in the bottom layer. Second, the underestimated sound path length in the deeper layer can be partially compensated by the overestimated path length in the superficial layer when the reconstruction speed falls between the true speeds of the two layers. The lateral FWHM of the fourth target located in the deeper layer shows deviation from an expected monotonic trend, and is typically larger than the deeper fifth and sixth targets; this may be due to undulating boundary effects, which will be discussed in the next section.

Mismatch between reconstruction sound speed and true speed of sound also causes incorrect estimation of target depth. FIG. 21A shows that reconstruction sound speeds higher than the true sound speed cause overestimation of target depth as expected (because reconstruction depth is the product of reconstruction sound speed and time delay), whereas values lower than the true sound speed cause underestimation of target depth in a homogenous phantom. The error in reconstruction depth is directly proportional to depth. In this analysis, target depths reconstructed using the true speed of sound value as ground truth were considered, and the depth of the first target was considered as a reference point. Similar depth overestimation can also be seen for the first three targets in the top layer of the heterogeneous phantom as shown in FIG. 21B. Underestimated depths for the second target may be due to slight misalignment during the construction process. The estimation error might be partially offset by the accumulative error from the top layer. The estimation errors for the deepest targets (fourth and fifth) are due to a combination of three factors: reconstruction speed mismatch, compensation from the overestimated path length in the superficial layer, and undulating boundary effects.

Boundary Undulation Effects on PAT Image Quality

Figure 22A:
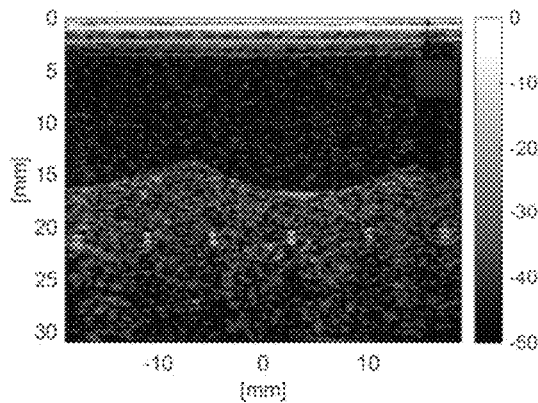
FIGS. 22A and 22B show ultrasound (22A) and PAT (22B) images of a heterogeneous phantom containing six tubes filled with an India ink solution possessing an optical absorption coefficient of 4.6 /cm at a wavelength of 750 nm. Target 1 is the signal farthest to the left and target 6 is on the far right.
Figure 22B:
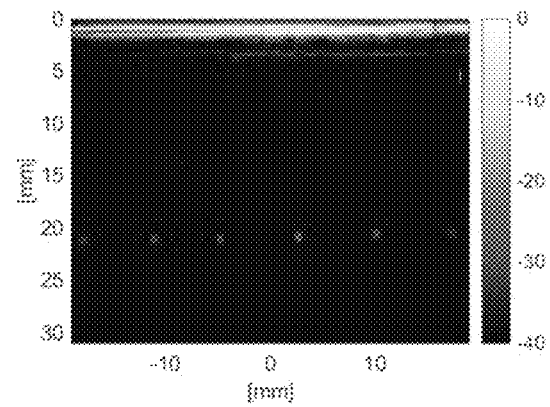
Figure 23A:
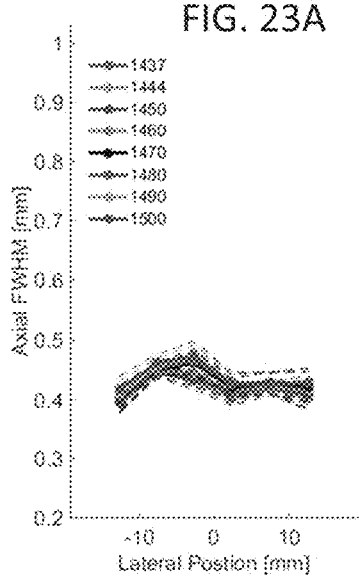
FIGS. 23A-23C are a set of graphs showing axial FWHM (23A), lateral FWHM (23B) and peak amplitude (23C) of the photoacoustic signal close to the tube top wall reconstructed using sound speed from 1437 m/s to 1500 m/s in a heterogeneous phantom containing six tubes at the same depth.
Figure 23B:
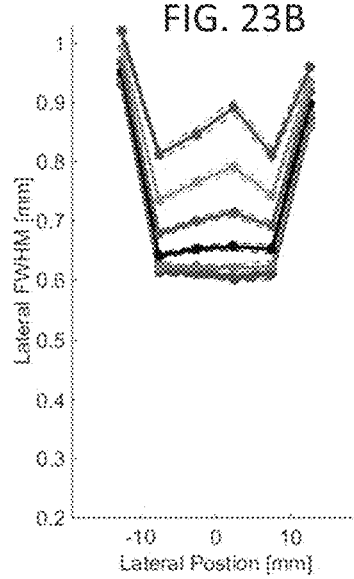

FIG. 22 shows ultrasound (20A) and PAT (20B) images of a heterogeneous phantom containing six PTFE tubes at the same depth as the fourth wire in the above heterogeneous phantom. Assuming that a two-layer phantom with a flat boundary will result in equal size and intensity of each tube, a phantom containing an undulating boundary can affect the dimensions and intensity of imaged targets as a function of lateral position relative to the undulation pattern. This undulation causes nonuniform variation in the sound propagation pattern across the transducer surface due to acoustic refraction of sound waves and can degrade image quality when a single homogeneous speed of sound value is assumed in image reconstruction. FIG. 23A indicates that, as expected, axial FWHM values are not significantly different from each other for all reconstruction sound speed values. FIG. 23B shows that lateral FWHM values of the targets at the same depth are related to the locations of the targets relative to the boundary undulation pattern. The first target and sixth target from left to right have the worst lateral FWHM. This is mainly because 1) reconstruction is performed with dynamic sub-aperture and 2) only half of the normal sub-aperture can be used for the targets close to the edge, and 3) lateral FWHM near the focal plane is inversely proportional to sub-aperture width. The sub-aperture length is 23 mm for a focal ratio (F number) of 0.9 at the imaging depth of about 21 mm. The second and fifth targets show similar dependences of lateral FWHM values on reconstruction sound speed. This might be due to the similar positions of the two targets relative to the boundary undulations. The fourth target FWHM is more sensitive to the reconstruction sound speed. This might be due to this target being directly under one of the undulation valleys, which has a focusing effect and caused the worst signal alignment in image reconstruction due to the refraction of sound across this valley. Therefore, the undulation also contributes the large variation in lateral FWHM estimation for the fourth wire at the same depth in the first heterogeneous phantom discussed above.

Figure 23C:
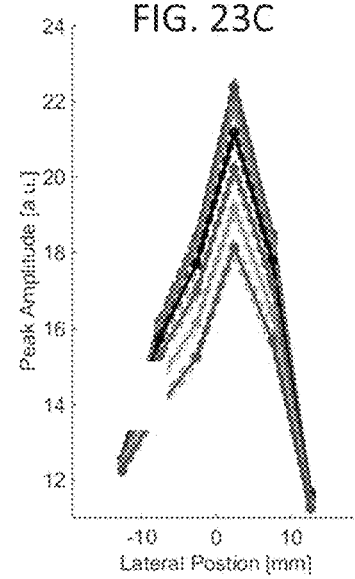

The photoacoustic amplitude is also sensitive to both the choice of reconstruction sound speed and acoustic attenuation distribution across the undulating boundary. Both dependences can be observed from the peak amplitudes of the six target signals shown in FIG. 23C. The first dependence can be observed by varying the reconstruction sound speed at one fixed target location. For example, the change in peak amplitudes of the fourth target vs. reconstruction sound is the opposite that of the lateral FWHM values. The decrease in the peak amplitude of this target with increasing reconstruction sound speed may be due to averaging effects in PAT imaging resulting from the corresponding increased target's lateral size estimate due to mismatched reconstruction sound speed in PAT image. The second dependence can be observed crossing the middle four targets at one fixed reconstruction sound speed. For example at reconstruction sound speed of 1460 m/s, even though the lateral FWHM of the fourth and fifth targets are similar to each other, the photoacoustic signal amplitude of the fifth target reduced to about 83% of that of the fourth target. This amplitude decrease may be explained by the relatively larger portion of highly attenuating fibroglandular TMM in the propagation path of the signal from the fifth target. For example, averaging 1 mm extra fibroglandular TMM thickness can cause about 6% amplitude decrease using the acoustic attenuation difference 5.5 dB/cm between two PVCP formulations at the central frequency of 7.5 MHz. The actual variation of PAT amplitude due to acoustic attenuation can be more complex because of the distribution of tissue types caused by the undulating boundary. This complexity might also explain the different PAT amplitudes between the second and fifth targets even though they have similar geometries.

Example 5

Tissue Simulating Phantoms for Photoacoustic and Ultrasound Imaging

This example illustrates formulations and configurations of PVCP tissue phantoms for objectively quantifying image quality characteristics for photoacoustic and ultrasound imaging. Specifically, the following performance characteristics were assayed: spatial resolution (axial, lateral), uniformity, spatial measurement accuracy, penetration depth, linearity, and sensitivity. The PVCP formulation used in this example was 75/25% v/v BBP/DEHA, 9% m/m PVC, 2 mg/mL TiO2, 30 mg/mL glass beads, which has a speed of sound of 1480 m/s and optical properties as discussed below.

Spatial resolution, uniformity, and spatial measurement accuracy were tested using a PVCP phantom containing a 5×9 grid of 0.002" (51 μm) diameter steel wires arranged with 5 mm lateral spacing and 7.5 mm lateral spacing. These wire targets are sufficiently small that they produce point spread functions when imaged by PAT or ultrasound. By having a relatively dense target grid through the field of view, image quality metrics can be calculated as a function of position within the image. The results using this PVCP phantom were compared with liquid phantoms comprised of 1% Intralipid in water, a common but limited phantom approach in biomedical optics and photo acoustics.

Methods

Modular PAT System

The PAT system used for this example was generally as discussed above for Example 1. Briefly, this system is comprised of a tunable near-infrared optical parametric oscillator (OPO) laser source (Phocus Mobile, Opotek, Inc., Carlsbad, Calif.) and a 128 channel, research-grade ultrasound system (Vantage 128, Verasonics, Inc., Kirkland, Wash.). The laser emits pulses with duration of 5 ns at a 10 Hz repetition rate, with tunable output from 690-950 nm. In this example, imaging was performed at 800 nm with a radiant exposure of 20 mJ/cm$^2$. An engineered diffuser was used to convert the laser fiber bundle output to an approximately rectangular beam measuring 5 mm×35 mm. To reduce near-field photoacoustic signal generation near the transducer surface, the beam was positioned approximately 5 mm from each transducer. Timing was controlled using the OPO output trigger, and image reconstruction was performed using a proprietary pixel-based method available from Verasonics. For imaging in Intralipid baths and in phantoms, the speed of sound input to the reconstruction algorithm was set to 1480 m/s, which is known a priori from phantom acoustic characterization data.

An important feature of this modular system is the ability to readily substitute difference ultrasound transducer arrays, each with different operating parameters (see the following table). Four transducers were used for B-mode ultrasound and PAT imaging of test phantoms, including a 128-element linear array (L11-4v, Verasonics), a 256-element multiplexed array (ATL L12-5-50 mm, Priority Medical, Inc., Greenbrier, Tenn.), a high-frequency intraoperative array (ATL CL15-7, Priority Medical), and a low-frequency phased array (ATL P4-1, Priority Medical). For all transducers except the L12-5, full images were acquired per laser pulse. Because the L12-5 spans 256 elements, but the ultrasound acquisition system only has 128 channels, three 128-element sub-aperture scans were acquired to generate full images (this requires 3 laser pulses per image). All transducers were shielded with aluminum foil to reduce surface-generated photoacoustic artifacts and improve image contrast. Background images were measured by averaging 30 frames acquired with zero laser output, then subtracted from target images in post-processing. Images are displayed as 8-bit intensity maps. To compare performance between images acquired with different transducers, no further post-processing was performed.

Operating Parameters of Four Clinical Ultrasound Transducer Arrays Used for PAT Imaging.

| Transducer | Center Frequency [MHz] | −20 dB Bandwidth [MHz] | Number of elements | Pitch [mm] | Length [mm] |
|---|---|---|---|---|---|
| L11-4v | 8.0 | 8.7 | 128 | 0.300 | 38.4 |
| L12-5 | 8.7 | 7.6 | 256 | 0.200 | 51.2 |
| CL15-7 | 12.4 | 7.9 | 128 | 0.178 | 22.8 |
| P4-1 | 2.5 | 2.2 | 96 | 0.295 | 28.3 |

Tissue-Mimicking Material

Solid tissue phantoms were constructed using a breast-mimicking PVC plastisol (PVCP) formulation as described above. Briefly, this formulation consisted of 10% m/m PVC (Geon 121A, Mexichem Specialty Resins, Inc., Avon Lake, Ohio) suspended in a 3:1 mixture of benzyl butyl phthalate and di(2-ethylhexyl) adipate, to which 1% v/v calcium-zinc heat stabilizer was added to prevent thermal discoloration (M-F Manufacturing Co, Fort Worth, Tex.). 2 mg/mL anatase titanium dioxide was added to impart tissue-relevant optical scattering (Sigma Aldrich, Inc.), and 30 mg/mL soda lime glass microbeads (diameter=38 to 63 µm, Spheriglass A, Potter Industries LLC, Malvern, Pa.) was added to provide acoustic scattering, enabling use of the phantoms for ultrasound imaging as well as photoacoustic imaging. Optical properties were determined for each PVCP phantom by performing spectrophotometry measurements in disk samples poured from the final layer batch used to produce each PVCP phantom (38 mm diameter, 5 mm thickness). The inverse adding-doubling method was used to calculate intrinsic absorption and reduced scattering coefficients, as described above.

To produce PVCP phantoms, PVCP was heated in 75 mL batches in an evacuated 250 mL round bottom flask suspended in an oil bath at 200° C. A rare-earth stir bar was driven at 350 rpm, and the PVCP was heated for 13 minutes. After heating, the flask was removed and suspended over a magnetic stir plate, and was stirred and allowed to cool to ~130° C. before pouring into a phantom mold. This has the effect of increasing the PVCP viscosity during pouring, but the higher viscosity at pour also substantially reduces glass bead settling during the final solidification phase.

Dual-Modality Spatial Resolution Phantoms

In order to develop a suitable phantom for testing spatial resolution, a phantom was constructed comprised of a triangular array of black monofilament suture wires, arranged in columns of 1 to 4 overlying filaments. This array was suspended in a 1% Intralipid solution to produce tissue-relevant optical scattering, but minimal acoustic attenuation (Sigma-Aldrich, St. Louis, Mo.). The purpose of this phantom was to determine if filaments would cause shadowing effects in either photoacoustic or ultrasound images, where the intensity of a deep high-contrast target depended on the number of filaments above it. Photoacoustic target intensity did not show a significant trend with number of overlying targets, but ultrasound target intensity did decrease with number of overlying targets. It was concluded from this phantom that a rectangular grid of targets is suitable for determining photoacoustic and ultrasound image quality characteristics with the exception of ultrasound intensity uniformity.

Tissue phantoms for photoacoustic image quality testing should have biologically relevant optical and acoustic properties. While Intralipid is a commonly used phantom material, these liquid solutions have similar acoustic absorption and scattering to water, thus presenting unrealistically minimal acoustic attenuation. To evaluate the potential differences in performance characteristics quantified, spatial resolution phantoms were constructed with similar geometries, but using either Intralipid or PVCP as the background medium. The Intralipid spatial resolution test phantom consists of a 5×9 grid of black monofilament suture wires with a 50µ diameter suspended in 1% Intralipid solution, prepared immediately before imaging was performed. Pouring PVCP over a grid of taut wires can potentially cause high enough loads to distort or break targets; to improve phantom fabrication quality for resolution targets in PVCP, 50.8 µm (0.002") diameter steel wire was used, which has higher mechanical strength and better resistant to heat than suture filaments. The PVCP phantom contained a target grid of the same number and dimensions as the Intralipid phantom.

Spatial resolution was quantified in both phantoms by selecting a rectangular region of interest (ROI) each target in the image, then locating the maximum intensity pixel. The vertical and horizontal intensity profiles of the target through this maximum were used to determine resolution based on the full width at half maximum (FWHM), or the −6 dB threshold distance for log-compressed images.

Sensitivity/Linearity Phantom

A PVCP phantom was constructed that contained a horizontal array of seven polytetrafluoroethylene (PTFE) tubes with nominal inner diameter of 1.07 mm (Zeus Light-wall PTFE tubing, Component Supply Company, Fort Meade, Fla.). To provide target contrast, six tubes were filled with a different concentration of India ink from 0 to 10 cm$^{-1}$, while the seventh tube was filled with deionized water as a control. This phantom was used to characterize signal linearity, dynamic range, and contrast resolution (expressed here as contrast vs. absorption coefficient).

Penetration Depth Phantom

While the linearity phantom provides a convenient method for multiplexing targets with varying absorption coefficients, sensitivity test results are limited because they do not account for signal attenuation with depth. A similar PVCP phantom containing a diagonal array of 0.5 mm diameter PTFE tubes at various depths was used to characterize signal attenuation with depth, as well as the maximum penetration/visualization depth. Tubes were filled with a carbon ink solution with $\mu_a$=4.0 cm$^{-1}$ at 800 nm, which corresponds to a hemoglobin concentration of 13.6 g/dL [refwho OMLC hemoglobin data or Zijlstra]. Hemoglobin concentration in female adults typically varies from 12 to 16 g/dL [refwho from clinical reference ranges for blood tests].

Contrast-Detail Phantom

Contrast-detail analysis is a common approach to characterizing visual detection of low-contrast features with varying intensity and size against a noisy background. A PVCP phantom was constructed containing multiple arrays of PTFE tubes at depths of 5, 10, and 15 mm. Each array contained PTFE tubes with nominal inner diameters of 0.3 mm, 0.5 mm, 1.0 mm, 1.5 mm, and 2.0 mm.

Results and Discussion

Spatial Resolution

Figure 24:
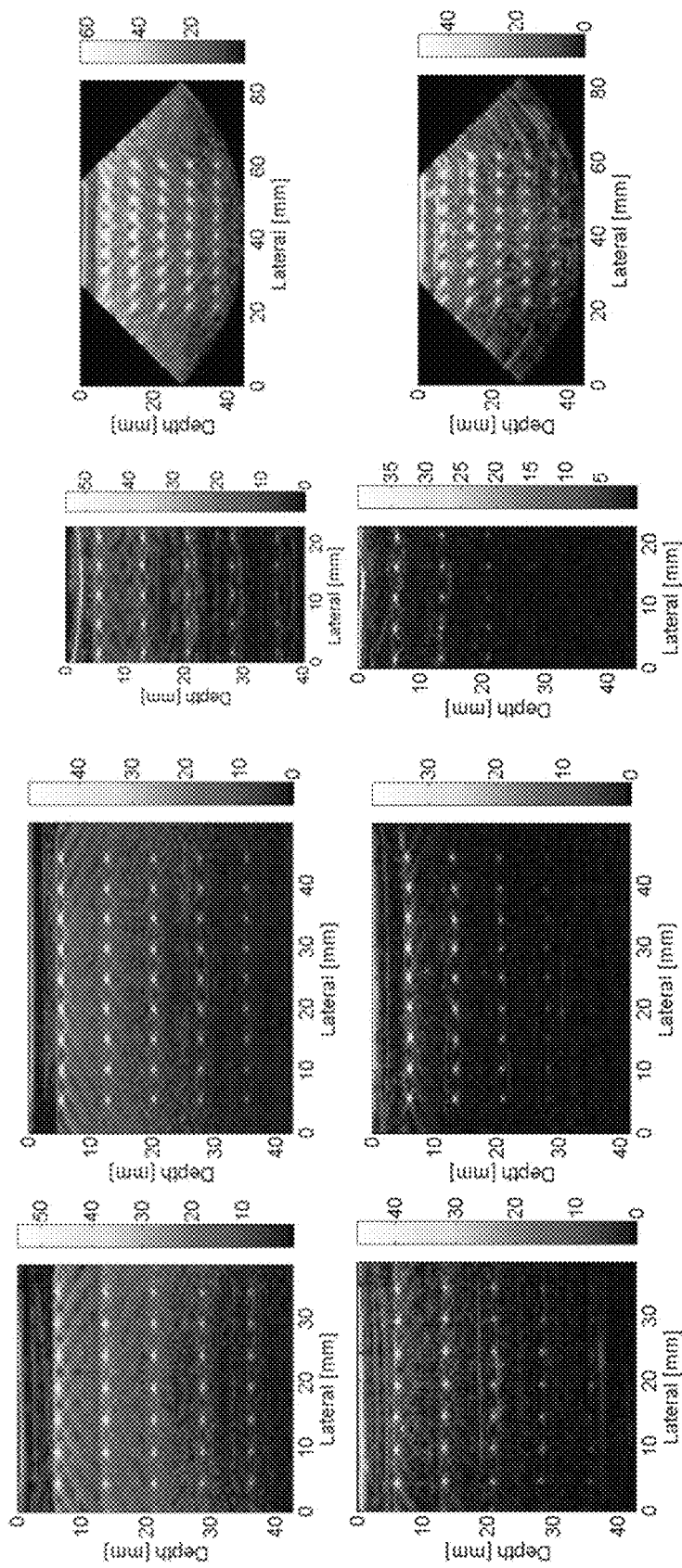
FIG. 24 shows representative PAT images of the Intralipid (upper row) and PVCP (lower row) resolution phantoms, acquired using, from left to right columns, L11-4v, L12-5, CL15-7, and P4-1 transducers.
Figure 25:
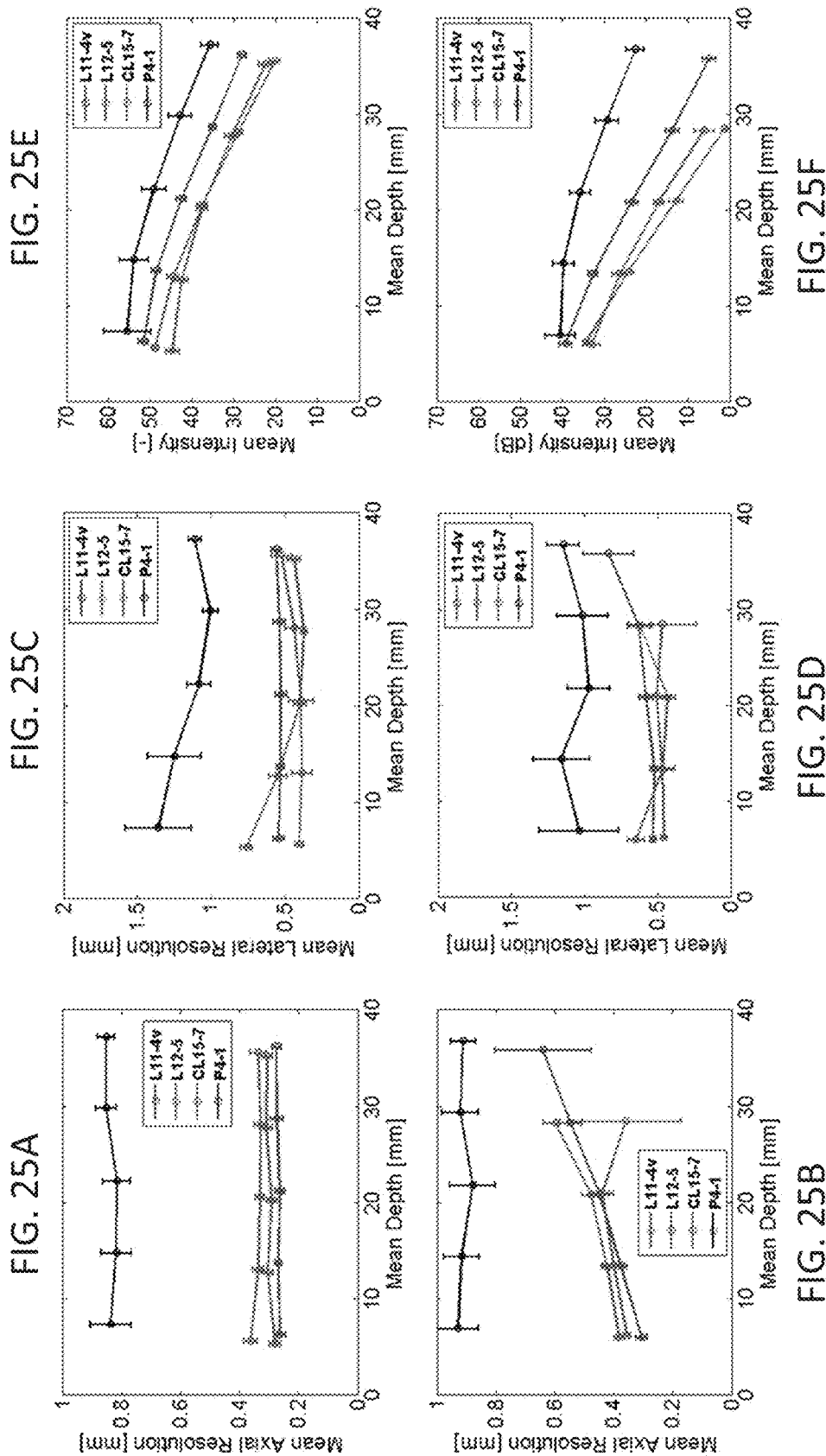
FIGS. 25A-25F are a set of graphs showing PAT image quality results for (25A-25B) axial resolution, (25C-25D) lateral resolution, and (25E-25F) intensity uniformity with depth. Top row: Intralipid phantom, bottom row: PVCP phantom. Error bars denote 1 standard deviation.
Figure 26:
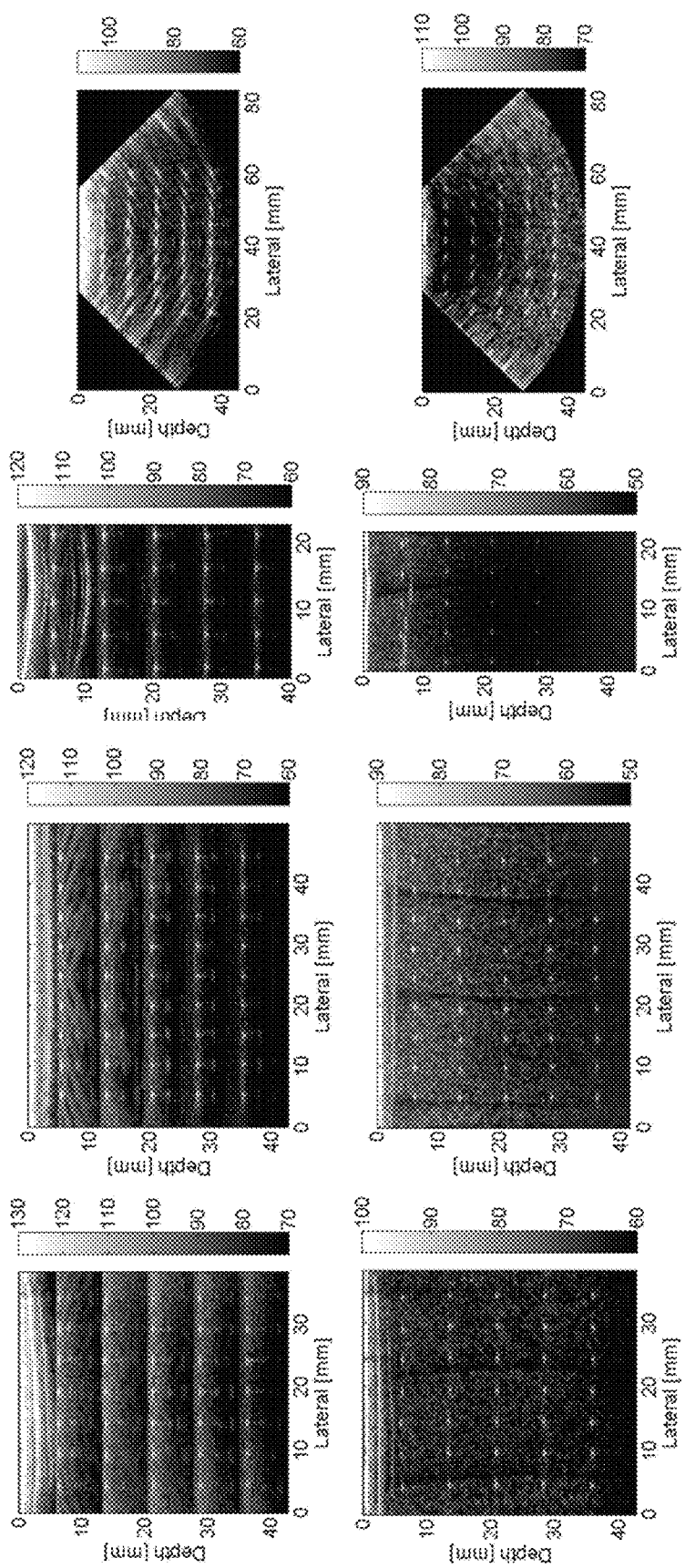
FIG. 26 shows representative ultrasound images of the Intralipid (upper row) and PVCP (lower row) resolution phantoms, acquired using, from left to right columns, L11-4v, L12-5, CL15-7, and P4-1 transducers.
Figure 27A:
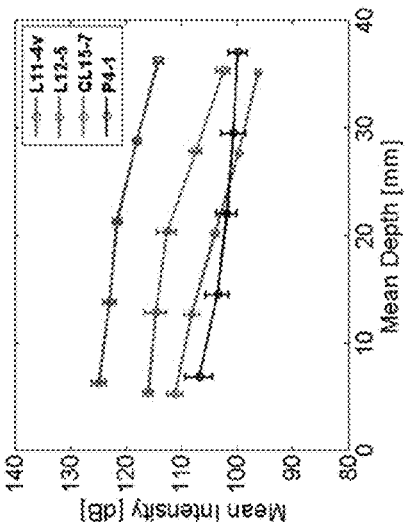
FIGS. 27A-27F are a set of graphs showing ultrasound image quality results for (27A-27B) axial resolution, (27C-27D) lateral resolution, and (27E-27F) intensity uniformity with depth. Top row: Intralipid phantom, bottom row: PVCP phantom. Error bars denote 1 standard deviation.
Figure 27C:
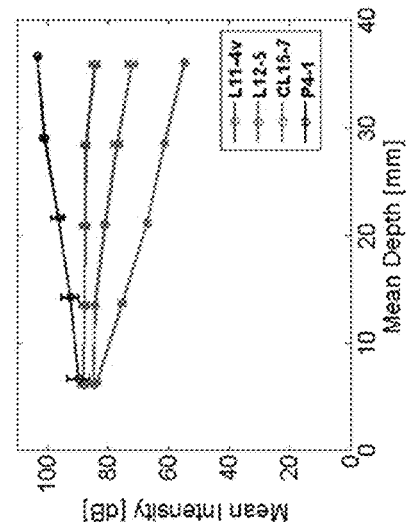
Figure 27E:
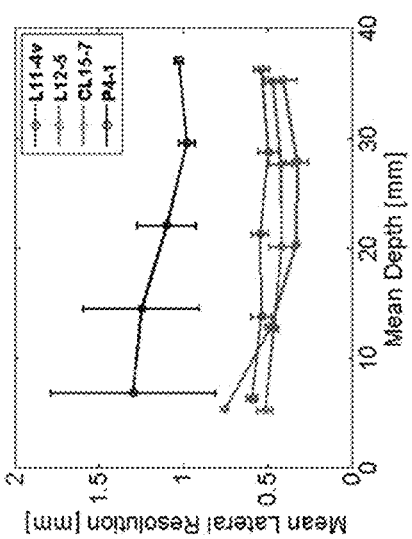
Figure 27B:
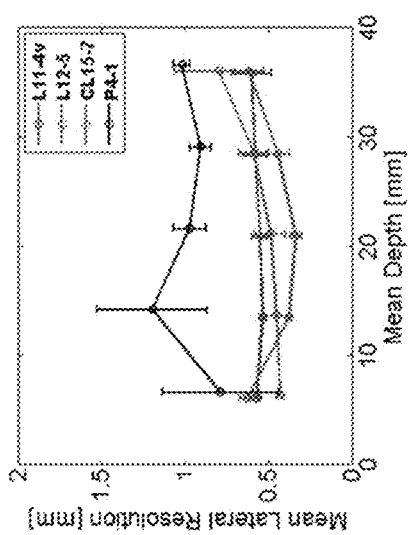
Figure 27D:
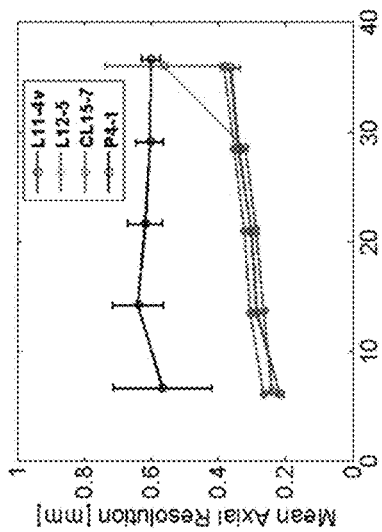
Figure 27F:
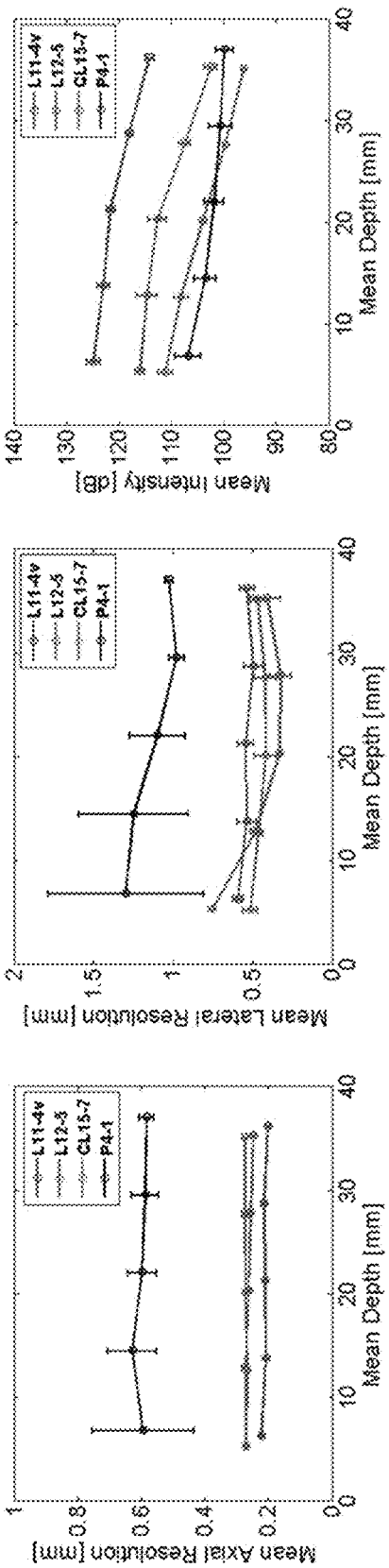

Representative PAT and ultrasound images of the Intralipid and PVCP resolution phantoms, acquired with each transducer, are shown in FIG. 24 and FIG. 26, respectively. In all images, significant lateral streak artifacts are observed, a product of the employed reconstruction algorithm. Some near-field clutter and horizontal bands are also caused by the presence of the protective aluminum foil. Additionally, because the P4-1 images are reconstructed over a sector with greater lateral span than the length of the transducer, significant limited-view artifacts are seen in the outermost target columns (apparent inward rotation of the targets). Another observation was that with the Intralipid phantom, where a manual motorized stage was used to adjust transducer height relative to the targets, target depths between transducer datasets vary due to limited positioning precision (this is reflected in depth shifts between traces in the plots of resolution vs. depth shown in FIG. 25 and FIG. 26). However, the PVCP phantom mitigates this effect, since the targets are fixed relative to the phantom surface where the transducer is placed. This demonstrates an advantage of using a solid, stable phantom medium over a liquid medium.

As shown in FIG. 25, axial resolution was found to not significantly depend on target depth in the Intralipid phantom. Additionally, three of the transducers (L11-4v, L12-5, CL15-7) show similar resolution values due to their similar acoustic bandwidths, while the P4-1 array has lower bandwidth and thus worse axial resolution. However, the axial resolution increased with depth in the PVCP phantom for all transducers. This effect is caused by phantom acoustic attenuation; because the attenuation spectrum of PVCP is nonlinear with frequency, the photoacoustic signal bandwidth will be reduced, causing an increase in axial resolution. This effect becomes more pronounced for deeper targets, although for some transducers the penetration depth in PVCP phantoms limits detection of deeper targets.

In Intralipid, the L11-4v and CL15-7 transducers had relatively constant lateral resolution while the L12-5 and P4-1 transducers showed strong lateral focusing effects. For the L12-5, this was due to the wide lateral transducer aperture, and fine element spacing, while the P4-1 focusing may have been caused by acoustic element design considerations (this array is optimized for deep tissue imaging). Ultrasound resolution data generally followed similar trends with depth as PAT data, although axial resolution values were lower in US images than in PAT images. Higher PAT resolution values may be due to out-of-plane photoacoustic signal contributions from the filament targets, or targets may have been blurred by a combination of frame averaging and trigger jitter observed in PAT mode (1-2 vertical pixels).

Uniformity

FIG. 25 shows mean intensity depth profiles for each transducer in both Intralipid and PVCP phantoms. Because images were log compressed, the data show relatively linear reductions in intensity with depth. Notably, intensities were generally lower in the PVCP phantom. This may be due to higher phantom acoustic attenuation compared with Intralipid. By plotting target intensity as a function of target grid position, 2D uniformity maps may be generated to evaluate uniformity within the entire target array. While the expected depth-dependent non-uniformity is observed in these maps, there is also significant lateral non-uniformity due to beam illumination geometry. This lateral non-uniformity is highest for longer transducer arrays, where the rectangular laser spot does not span the entire image plane. For example, the L12-5 uniformity map suggests that the laser spot was slightly misaligned relative to the transducer center element.

Spatial Measurement and Co-Registration Accuracy

Figure 28A:
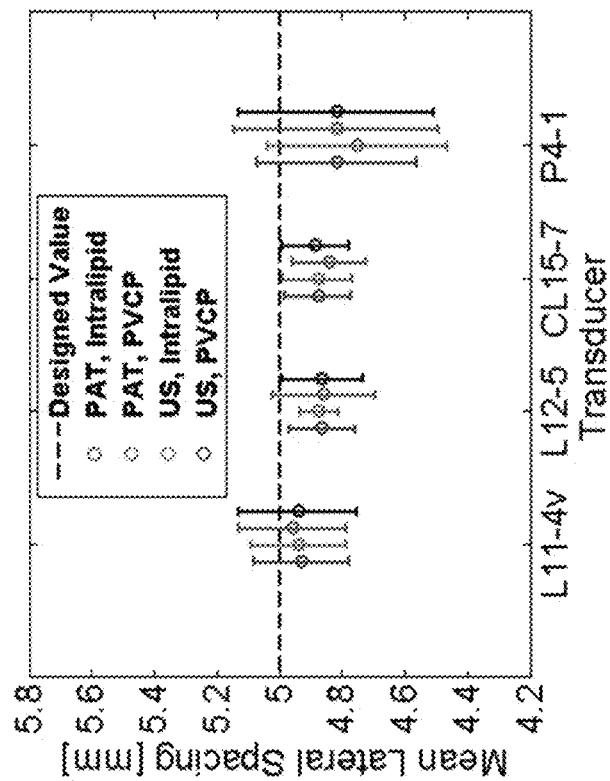
FIGS. 28A-28B are a set of graphs showing results from spatial measurement accuracy/precision for (28A) axial and (28B) lateral spacing between target filaments. The dashed line denotes the designed spacing value of the array. Error bars denote 1 standard deviation.
Figure 28B:
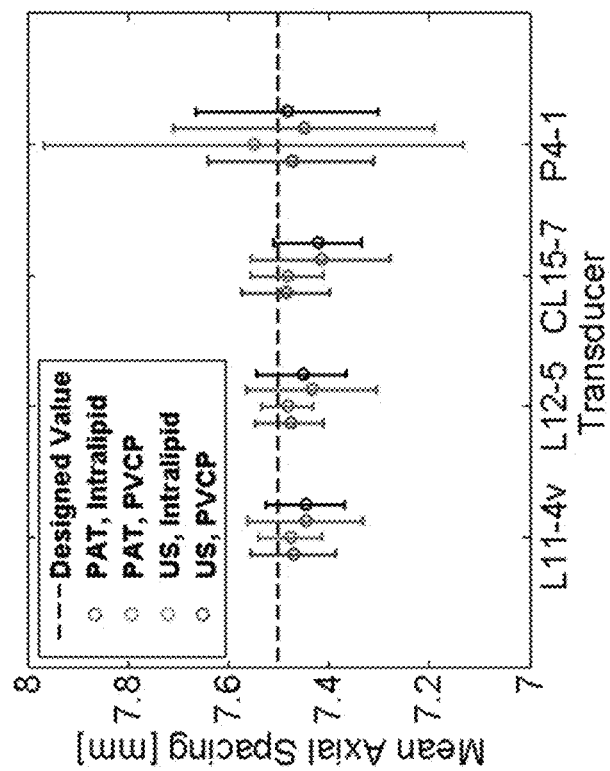
Figure 29A:
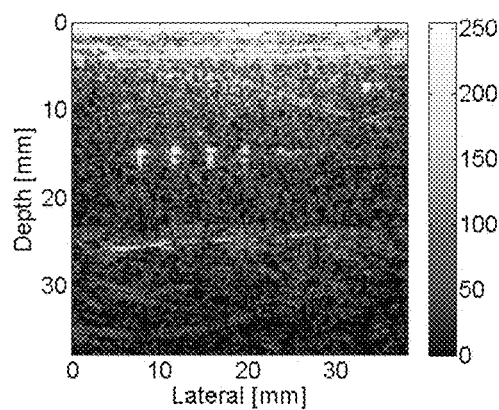
FIGS. 29A-29D show PAT images of sensitivity phantom for (29A) L11-4v, (29B) L12-5, (29C) CL15-7, and (29D) P4-1 transducer arrays.
Figure 29B:
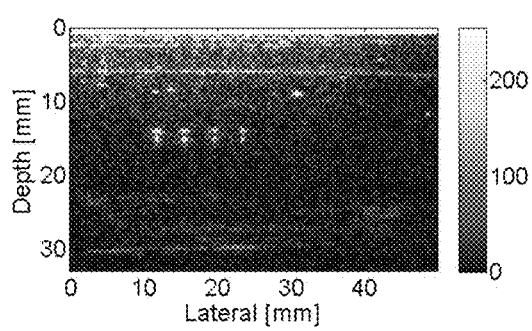
Figure 29C:
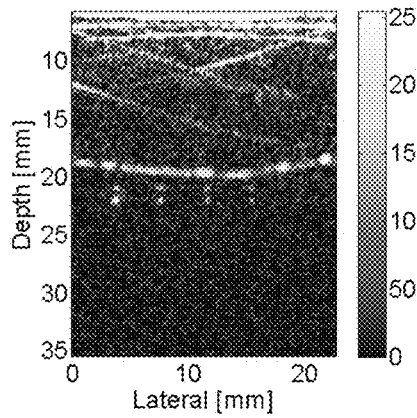
Figure 29D:
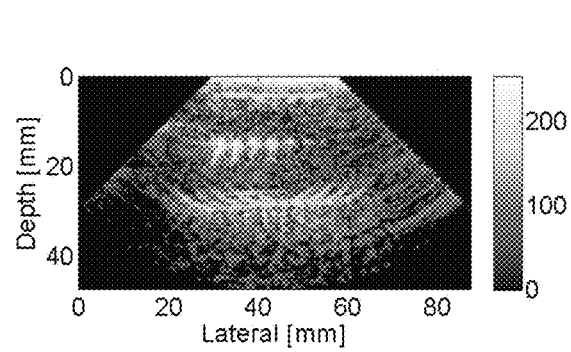

Spatial measurement accuracy results are shown in FIG. 28. PAT and US distance measurements were found to be in good agreement with each other and the reference value (the designed grid spacing of the array targets). Axial measurement precision was found to correlate with transducer bandwidth, while lateral measurement precision was higher for transducers for finer element pitch (L12-5 and CL15-7). The P4-1 array exhibited the worst performance due to its low bandwidth and coarse element spacing. Image compression did not significantly affect spatial measurement accuracy. Results were consistent between the Intralipid and PVCP phantoms for all transducers.

PAT and US images showed good co-registration, with average registration errors less than or equal to 1 pixel. However, maximum registration errors of 1-2 pixels were observed, depending on the selected transducer and spatial direction (see the following table). Lateral registration error is determined by ultrasound array element spacing, while axial registration error may be caused by system timing jitter, resulting in temporal shifts in received pressure wave signals.

Maximum US/PAT Registration Error Over All Targets For Each Transducer

|  | L11-4v | L12-5 | CL15-7 | P4-1 |
|---|---|---|---|---|
| Max Lateral Error | 0.300 mm (1 pixel) | 0.195 mm (1 pixel) | 0.178 mm (1 pixel) | 0.888 mm (2 pixels) |
| Max Axial Error | 0.095 mm (1 pixel) | 0.189 mm (2 pixels) | 0.142 mm (2 pixels) | 0.592 mm (2 pixels) |

Sensitivity and Penetration Depth

Figure 30:
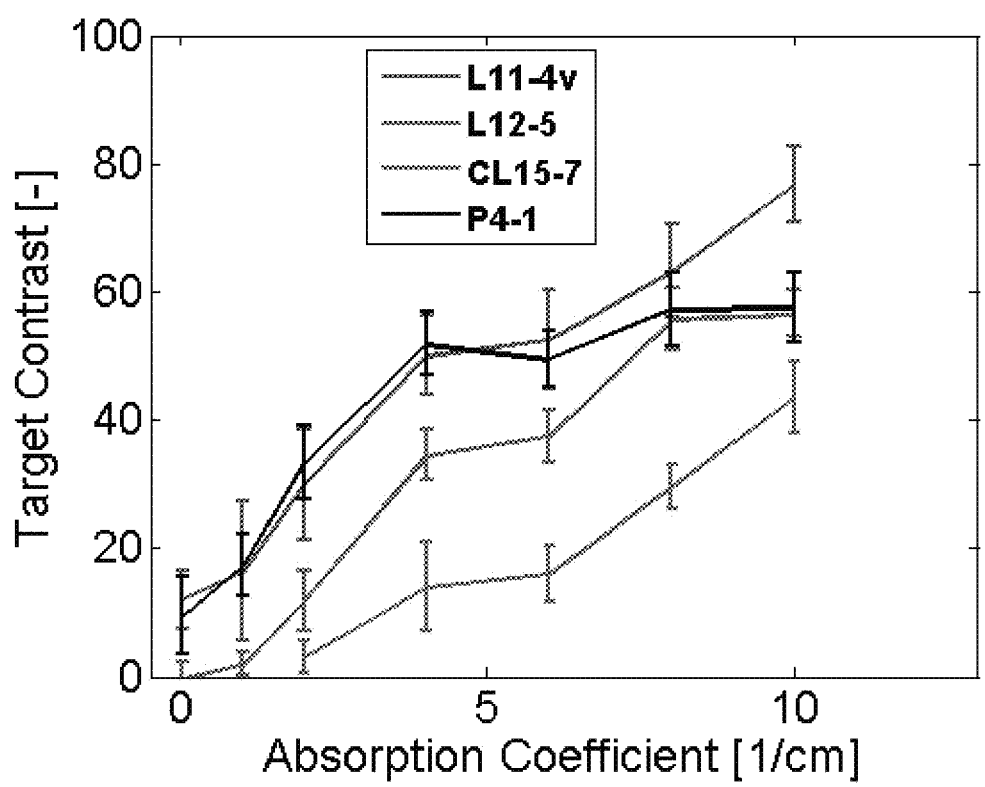
FIG. 30 is a graph showing results of target contrast vs. absorption coefficient for the L11-4v, L12-5, CL15-7, and P4-1 transducer arrays.
Figure 31A:
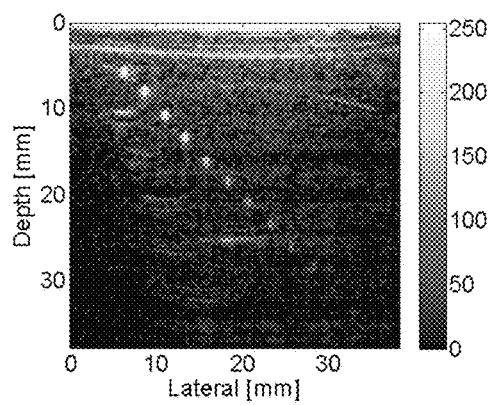
FIGS. 31A-31D show PAT images of penetration depth phantom for (31A) L11-4v, (31B) L12-5, (31C) CL15-7, and (31D) P4-1 transducer arrays.
Figure 31B:
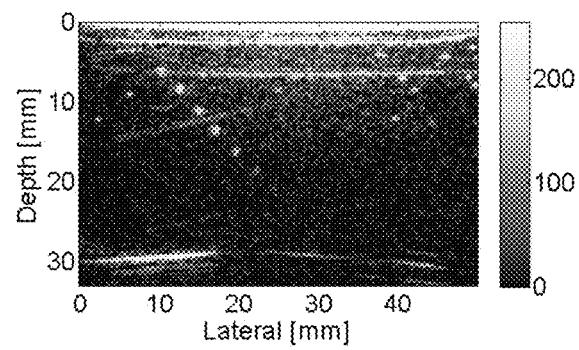
Figure 31C:
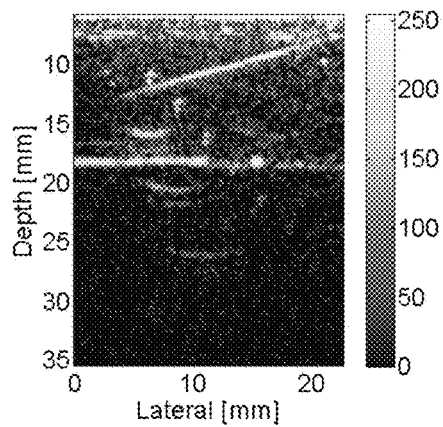
Figure 31D:
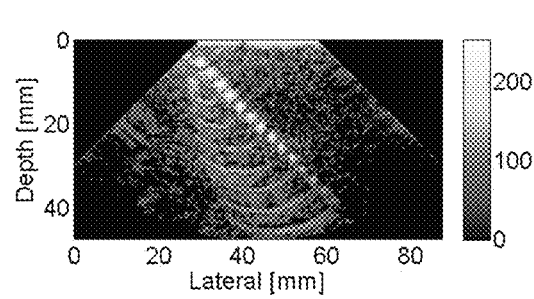
Figure 32:
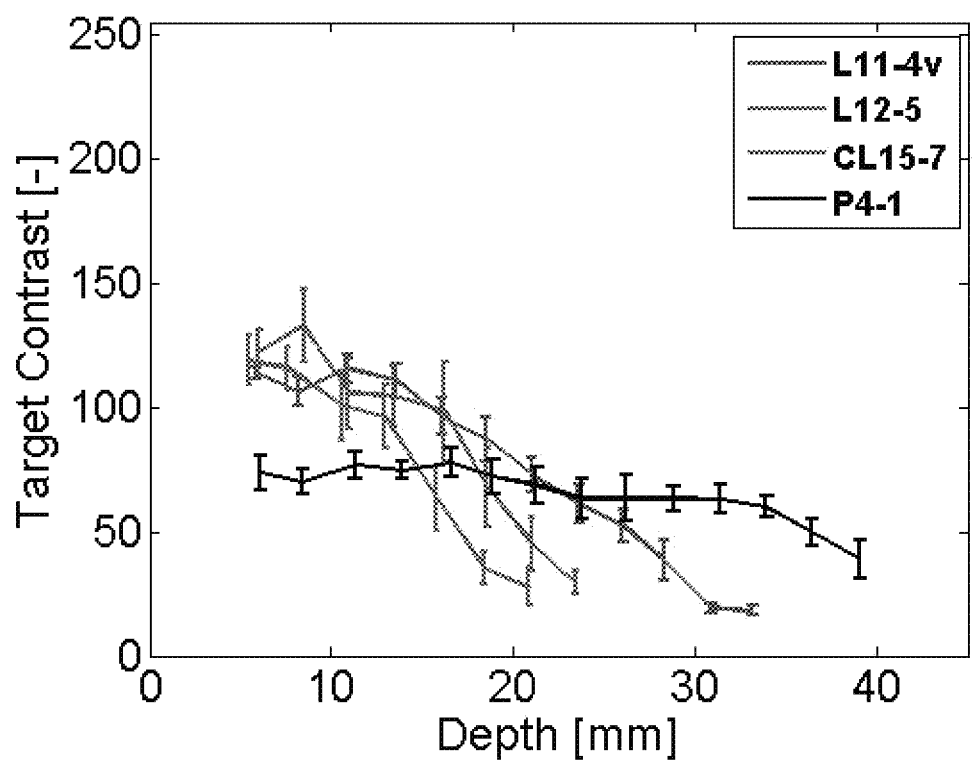
FIG. 32 is a graph showing target contrast vs. depth in the penetration depth phantom for the L11-4v, L12-5, CL15-7, and P4-1 transducer arrays.

Spatial sensitivity accuracy results are summarized in FIGS. 29-30, and penetration depth results are summarized in FIGS. 31-32. Based on qualitative visual detection of the targets, a detection threshold contrast of ~10 appears reasonable. While a linear relationship between target contrast and absorption coefficient was expected, there are several effects that cause deviation from a linear profile. These include the effect of background intensity, which is particularly high for the P4-1 transducer, resulting in a contrast plateau for the strongest targets. Additionally, the tube filled with a solution with an absorption coefficient of 4 cm$^{-1}$ generally showed slightly higher contrast than expected for a linear trend. This may be the result of variation in tube alignment relative to delivered light or the acoustic transducer. Penetration phantom data indicate that penetration performance was determined in large part by the frequency-dependent acoustic attenuation of the phantom, with higher frequency transducers resulting in lower penetration depths. Also, the P4-1 array recovered deeper targets with higher contrast than other transducers, but also experienced worse contrast for shallow targets due to high background intensity.

It will be apparent that the precise details of the methods or compositions described may be varied or modified without departing from the spirit of the described embodiments. We claim all such modifications and variations that fall within the scope and spirit of the claims below.

The invention claimed is:

1. A phantom, comprising:
a poly(vinyl chloride) plastisol (PVCP) comprising poly(vinyl chloride)(PVC) and a binary plasticizer comprising or consisting of benzyl butyl phthalate (BBP) and di (2-ethylhexyl) adipate (DEHA), wherein the phantom is configured to simulate the optical and acoustic properties of a living tissue.

2. The phantom of claim 1, wherein the phantom is further configured to simulates the morphological properties of the living tissue.

3. The phantom of claim 1, wherein the phantom is for use with detection and imaging systems based on optics and/or acoustics.

4. The phantom of claim 3, wherein the phantom is for use with photoacoustic and/or ultrasound imaging systems.

5. The phantom of claim 1, wherein the PVCP gel comprises from 2% to 20% m/m PVC/binary plasticizer.

6. The phantom of claim 5, wherein the PVCP gel comprises from 10% to 20%, from 5% to 15%, from 7% to 15%, from 7% to 12%, or from 8% to 10%, m/m PVC/binary plasticizer.

7. The phantom of claim 5, wherein the PVCP gel comprises about 5%, about 8%, about 9%, about 10%, about 11%, about 15%, or about 20%, m/m PVC/binary plasticizer.

8. The phantom of claim 1, wherein the binary plasticizer comprises or consists of BBP and DEHA at a volume ratio of from 1000:1 to 1:1000.

9. The phantom of claim 8, wherein the binary plasticizer comprises or consists of BBP and DEHA at a volume ratio of from 100:1 to 1:100.

10. The phantom of claim 8, wherein the binary plasticizer comprises or consists of BBP and DEHA at a volume ratio of about 99:1, about 95:5, about 90:10, about 85:15, about 80:20, about 75:25, about 70:30, about 60:40, about 50:50, about 40:60, about 30:70, about 25:75, about 10:90, or about 1:99.

11. The phantom of claim 8, wherein the binary plasticizer comprises or consists of BBP and DEHA at a volume ratio of 99:1, 95:5, 90:10, 85:15, 80:20, 75:25, 70:30, 60:40, 50:50, 40:60, 30:70, 25:75, 10:90, or 1:99.

12. The phantom of claim 1, wherein the PVCP gel further comprises one or more additives comprising an optical absorber, an optical scatterer, an acoustic absorber, and/or an acoustic scatterer.

13. The phantom of claim 12, wherein:
the optical absorber comprises black plastic colorant (BPC);
the optical scatterer comprises titanium dioxide, such as anatase $TiO_2$ with mean particle/agglomerate diameter of from 500 to 600 nm;
the acoustic absorber comprises glass microparticles comprising a mean diameter of from 10 to 100 µm; and/or
the acoustic scatterer comprises glass microparticles comprising a mean diameter of less than 10 µm.

14. The phantom of claim 1, wherein the PVCP gel comprises:
7-12% m/m PVC/binary plasticizer wherein the binary plasticizer comprises or consists of BBP and DEHA at a volume ratio of from 25/75 to 90/10 BBP/DEHA;
0-100 mg/mL glass microparticles;
0-3 mg/mL titanium dioxide; and
0-0.5% v/v black plastic colorant (BPC).

15. The phantom of claim 1, wherein the PVCP gel simulates:
fatty breast tissue, wherein the PVCP gel comprises about 10% m/m PVC/binary plasticizer, binary plasticizer comprising BBP and DEHA at a volume ratio of about 30 to about 70, about 25 mg/mL silica microparticles, about 1.5 mg/mL titanium dioxide, and no BPC;
breast tissue with moderate relative fat/parenchyma content, wherein the PVCP gel comprises about 10% m/m PVC/binary plasticizer, binary plasticizer comprising BBP and DEHA at a volume ratio of about 75 to about 25, about 50 mg/mL silica microparticles, about 1.75 mg/mL titanium dioxide, and about 0.002% v/v BPC;
breast tissue with moderate relative fat/parenchyma content, wherein the PVCP gel comprises about 10% m/m PVC/binary plasticizer, binary plasticizer comprising BBP and DEHA at a volume ratio of about 75 to about 25, about 30 mg/mL silica microparticles, about 2.0 mg/mL titanium dioxide, and about 0.002% v/v BPC;
breast tissue with moderate relative fat/parenchyma content, wherein the PVCP gel comprises about 8.4% m/m PVC/binary plasticizer, binary plasticizer comprising BBP and DEHA at a volume ratio of about 40 to about 60, about 10 mg/mL silica microparticles, and about 2.29 mg/mL titanium dioxide;
parenchymal breast tissue, wherein the PVCP gel comprises about 10% m/m PVC/binary plasticizer, binary plasticizer comprising BBP and DEHA at a volume ratio of about 90 to about 10, about 100 mg/mL silica microparticles, about 2.5 mg/mL titanium dioxide, and about 0.002% v/v BPC;
parenchymal breast tissue, wherein the PVCP gel comprises about 8.6% m/m PVC/binary plasticizer, binary plasticizer comprising BBP and DEHA at a volume ratio of about 87 to about 13, about 30 mg/mL silica microparticles, about 2.95 mg/mL titanium dioxide;
skin, wherein the PVCP gel comprises about 10% m/m PVC/binary plasticizer, binary plasticizer comprising BBP and DEHA at a volume ratio of about 99 to about 1, about 200 mg/mL silica microparticles, about 2.5 mg/mL titanium dioxide, and about 0.008% v/v BPC;
abdominal fat, wherein the PVCP gel comprises about 10% m/m PVC/binary plasticizer, binary plasticizer comprising BBP and DEHA at a volume ratio of about 40 to about 60, no silica microparticles, about 1.5 mg/mL titanium dioxide, and no BPC;

brain, wherein the PVCP gel comprises about 8% m/m PVC/binary plasticizer, binary plasticizer comprising BBP and DEHA at a volume ratio of about 90 to about 10, about 25 mg/mL silica microparticles, about 2.5 mg/mL titanium dioxide, and no BPC;

liver, wherein the PVCP gel comprises about 8% m/m PVC/binary plasticizer, binary plasticizer comprising BBP and DEHA at a volume ratio of about 75 to about 25, about 50 mg/mL silica microparticles, about 1.5 mg/mL titanium dioxide, and about 0.004% v/v BPC; or skeletal muscle, wherein the PVCP gel comprises about 8% m/m PVC/binary plasticizer, binary plasticizer comprising BBP and DEHA at a volume ratio of about 75 to about 25, about 100 mg/mL silica microparticles, about 2.0 mg/mL titanium dioxide, and about 0.012% v/v BPC.

16. The phantom of claim 1, wherein the PVCP gel further comprises about 1% v/v heat stabilizer/binary plasticizer.

17. The phantom of claim 1, wherein the PVCP gel comprises:
an acoustic attenuation value of from 0.5 to 6 dB/cm at 4 MHz to from 5 to 30 dB/cm at 9 MHz;
an optical absorption coefficient of from 0.05 to 10 $cm^{-1}$ at 400 nm and from 0.05 to 10 $cm^{-1}$ at 1100 nm,
an optical scattering coefficient of from 0.05 to 40 $cm^{-1}$ at 400 nm and from 0.05 to 20 $cm^{-1}$ at 1100 nm; and/or
wherein the speed of sound through the PVCP gel is from 1400 to 1520 m/s.

18. The phantom of claim 1, wherein the phantom simulates the morphology, optical properties, and acoustic properties of a living organ or tissue, of body parts, or of whole animals.

19. The phantom of claim 18, wherein the phantom comprises a shape simulating the morphology of a living organ or tissue, of body parts, or of whole animals.

20. The phantom of claim 19, wherein the phantom comprises a shape of a small mammal, such as a mouse.

21. The phantom of claim 1, further comprising a plurality of the PVCP gels, each PVCP gel simulating the optical and acoustic properties of a different living organ or tissue so as to simulate an organ and its environment.

22. The phantom of claim 21, wherein the phantom simulates the morphology, optical properties, and acoustic properties of breast tissue.

23. The phantom of claim 22, wherein the phantom comprises a first PVCP gel that simulates the morphology, optical properties, and acoustic properties of breast tissue with moderate relative fat/parenchyma content and a second PVCP gel that simulates the morphology, optical properties, and acoustic properties of parenchymal breast tissue.

24. The phantom of claim 1, further comprising one or more filaments embedded in the PVCP gel to provide a series of targets for calibrating or testing the performance characteristics of a photoacoustic and/or ultrasound detection system.

25. The phantom of claim 1, further comprising one or more solid inclusions embedded in the PVCP gel to provide a series of targets for calibrating or testing the performance characteristics of a photoacoustic and/or ultrasound detection system, wherein the solid inclusions have optical and/or acoustic properties that are detectably different from those of the PVCP gel.

26. The phantom of claim 1, further comprising:
one or more fluid channels in the PVCP gel;
wherein the one or more fluid channels are filled with a liquid solution comprising one or more of an optical absorber, an optical scatterer, an acoustic absorber, and an acoustic scatterer, to provide a series of targets for calibrating or testing the performance characteristics of a photoacoustic and/or ultrasound detection system; and
particularly wherein the one or more fluid channels are filled with a solution comprising natural or synthetic hemoglobin.

27. A composition, comprising: poly(vinyl chloride) (PVC) and a binary plasticizer comprising or consisting of benzyl butyl phthalate (BBP) and di(2-ethylhexyl) adipate (DEHA), wherein said composition is configured to simulate both optical and acoustic properties of a living tissue.

28. A method of producing a phantom, comprising:
providing a composition according to claim 24; and
forming the composition into the shape of the phantom.

29. A method of using an optical and/or acoustic detection system, comprising:
providing the phantom of claim 1;
directing optical pulses of light at ultraviolet, visible, near-infrared and/or infrared wavelengths to the phantom; and/or
directing acoustic waves at frequencies between 10 kHz and 20 GHz to the phantom; and
detecting optical and/or acoustic signals produced at the phantom responsive to the optical pulses and/or acoustic waves.

30. The method of claim 29, wherein the detection system is a photoacoustic detection system or an ultrasound detection system.

31. A detection system, comprising: a photoacoustic detection system, comprising: an optical pulse source configured to direct optical pulses at ultraviolet, visible, near-infrared and/or infrared wavelengths to a target; the target, wherein the target comprises the phantom of claim 1; one or more acoustic transducers configured to detect acoustic signals produced in response to the optical pulses directed to the target; and a signal processor configured to receive the detected acoustic signals and process the acoustic signals to generate spectroscopic data or imaging data and/or other diagnostic data.

32. A detection system comprising:
an ultrasound detection system, comprising: an ultrasound source configured to direct ultrasound pulses of frequencies between 10 kHz and 20 GHz to the target;
the target wherein the target comprises the phantom of claim 1;
one or more acoustic transducers configured to detect acoustic signals produced in response to the ultrasound pulses directed to the target; and
a signal processor configured to receive the detected acoustic signals and process the acoustic signals to generate spectroscopic data or imaging data and/or other diagnostic data.

* * * * *